US 7,750,007 B2

(12) United States Patent
Bearss et al.

(10) Patent No.: US 7,750,007 B2
(45) Date of Patent: Jul. 6, 2010

(54) IMIDAZO[1,2-BETA]PYRIDAZINE AND PYRAZOLO[1,5-ALPHA]PYRIMIDINE DERIVATIVES AND THEIR USE AS PROTEIN KINASE INHIBITORS

(75) Inventors: David J. Bearss, Cedar Hills, UT (US); Xiao-Hui Liu, Sandy, UT (US); Hariprasad Vankayalapati, Draper, UT (US); Yong Xu, Midvale, UT (US)

(73) Assignee: SuperGen, Inc., Dublin, CA (US)

( * ) Notice: Subject to any disclaimer, the term of this patent is extended or adjusted under 35 U.S.C. 154(b) by 36 days.

(21) Appl. No.: 11/935,959

(22) Filed: Nov. 6, 2007

(65) Prior Publication Data
US 2008/0261988 A1 Oct. 23, 2008

Related U.S. Application Data

(60) Provisional application No. 60/864,566, filed on Nov. 6, 2006, provisional application No. 60/892,523, filed on Mar. 1, 2007, provisional application No. 60/957,988, filed on Aug. 24, 2007.

(51) Int. Cl.
*A61K 31/5025* (2006.01)
*A61K 31/519* (2006.01)
*C07D 413/12* (2006.01)
*C07D 487/04* (2006.01)
*A61K 31/5375* (2006.01)
*A61P 35/00* (2006.01)

(52) U.S. Cl. .................... 514/248; 544/236; 544/281; 544/117; 544/224

(58) Field of Classification Search ................ 544/236; 514/247, 248
See application file for complete search history.

(56) References Cited

U.S. PATENT DOCUMENTS

2007/0093490 A1  4/2007  Prien et al.

FOREIGN PATENT DOCUMENTS

| DE | 10 2006 029 447 A1 | 12/2007 |
| WO | WO 96/31509 A1 | 10/1996 |
| WO | WO 2004/024895 A2 | 3/2004 |
| WO | WO 2004/058769 A2 | 7/2004 |
| WO | WO 2007/013673 A1 | 2/2007 |
| WO | WO 2007/025540 A2 | 3/2007 |
| WO | WO 2007/041712 A1 | 4/2007 |
| WO | WO 2008/025822 A1 | 3/2008 |
| WO | WO 2008/030579 A2 | 3/2008 |

OTHER PUBLICATIONS

Xia, et al., J. Med. Chem., 2009, 52 (1), pp. 74-86.*
Bullock et al., "Structural Basis of Inhibitor Specificity of the Human Protooncogene Proviral Insertion Site in Moloney Murine Leukemia Virus (PIM-1) Kinase," J Med Chem 48(24):7604-7614, 2005.
Chezal et al., "Efficient synthesis of novel dipyridoimidazoles and pyrido[1',2';1,2]imidazo[4,5-d]pyridazine derivatives," Tetrahedron 59:5869-5878, 2003.
Jacobs et al., "Pim-1 Ligand-bound Structures Reveal the Mechanism of Serine/Threonine Kinase Inhibition by LY294002," J Biol Chem 280(14):13728-13734, Apr. 8, 2005.
Kumar et al., "Crystal Structures of Proto-oncogene Kinase Pim1: A Target of Aberrant somatic Hypermutations in Diffuse Large Cell Lymphoma," J Mol Biol 348:183-193, 2005.
Qian et al., "Structural Basis of Constitutive Activity and a Unique Nucleotide Binding Mode of Human Pim-1 Kinase," J Biol Chem 280(7):6130-6137, Feb. 18, 2005.
Raboisson et al., "Efficient preparation of imidazo[1,2-β]pyridazines under Swern oxidative conditions," Tetrahedron Letters 44(14):2919-2921, Mar. 31, 2003.
Williamson et al., "Structure-guided design of pyrazolo[1,5-60 ] pyrimidines as inhibitors of human cyclin-dependent kinase 2," Bioorg Med Chem Lett 15:863-867, 2005.

* cited by examiner

Primary Examiner—Mark L Berch
Assistant Examiner—Cecilia M Jaisle
(74) Attorney, Agent, or Firm—Seed IP Law Group PLLC

(57) ABSTRACT

The present invention provides protein kinase inhibitors comprising imidazo[1,2-b]pyridazine and pyrazolo[1,5-a]pyrimidine compounds of the following structure (I) and (II):

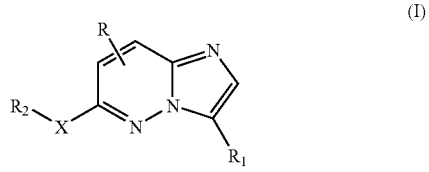

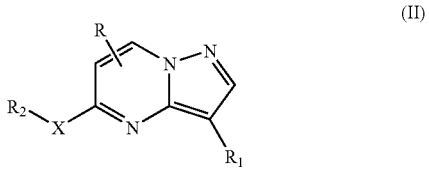

or a stereoisomer, prodrug or pharmaceutically acceptable salt thereof, wherein R, $R_1$, $R_2$ and X are as defined herein. Compositions and methods for using the same in the treatment of cancer and other Pim kinase-associated conditions are also disclosed.

9 Claims, 5 Drawing Sheets

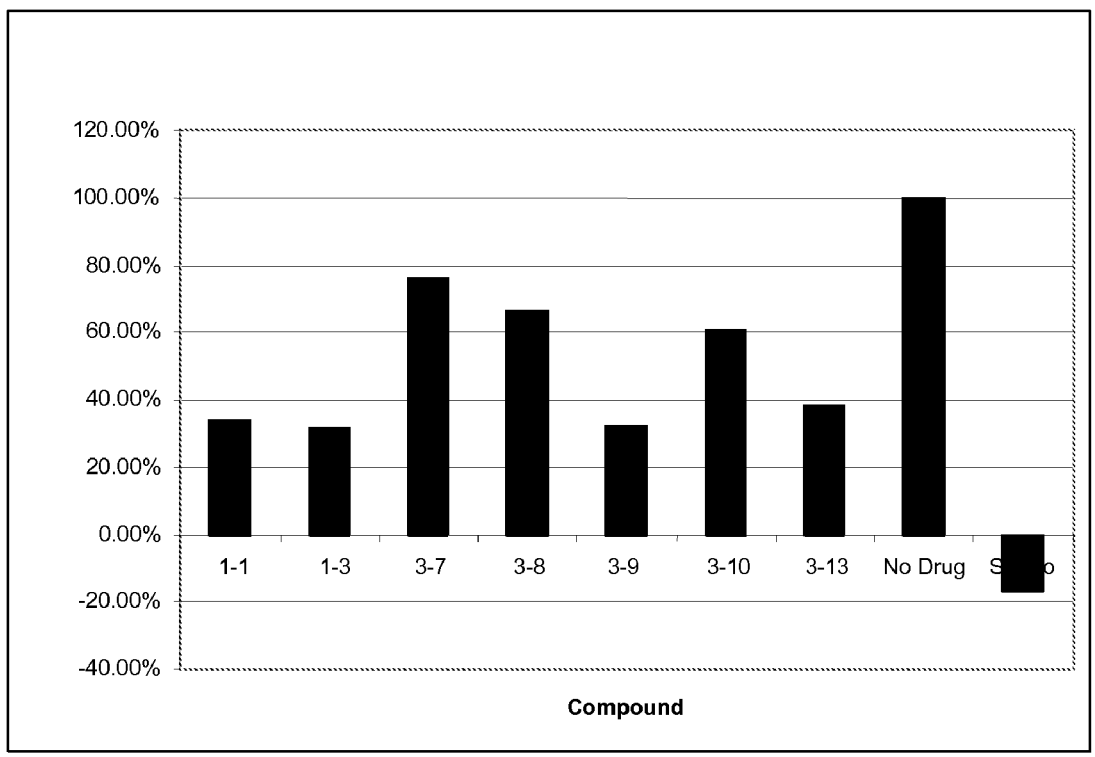
Figure 1. Percent activity of Illustrative Compounds..

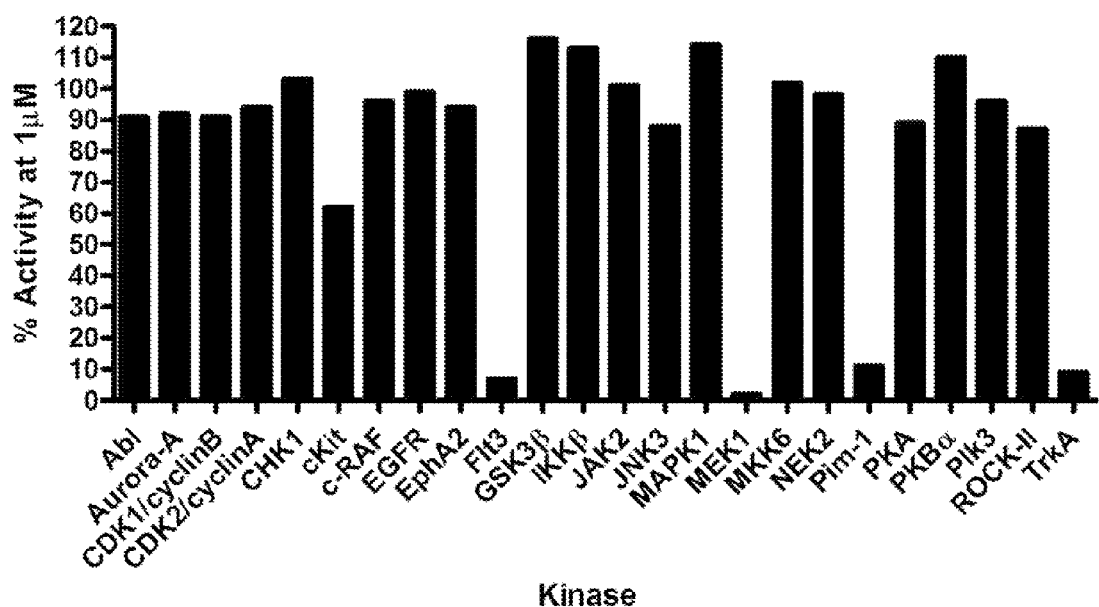
Figure 2. Selectivity of Pim1 illustrative inhibitor 7-29 against a panel of protein kinases (% inhibition at 1 μM).

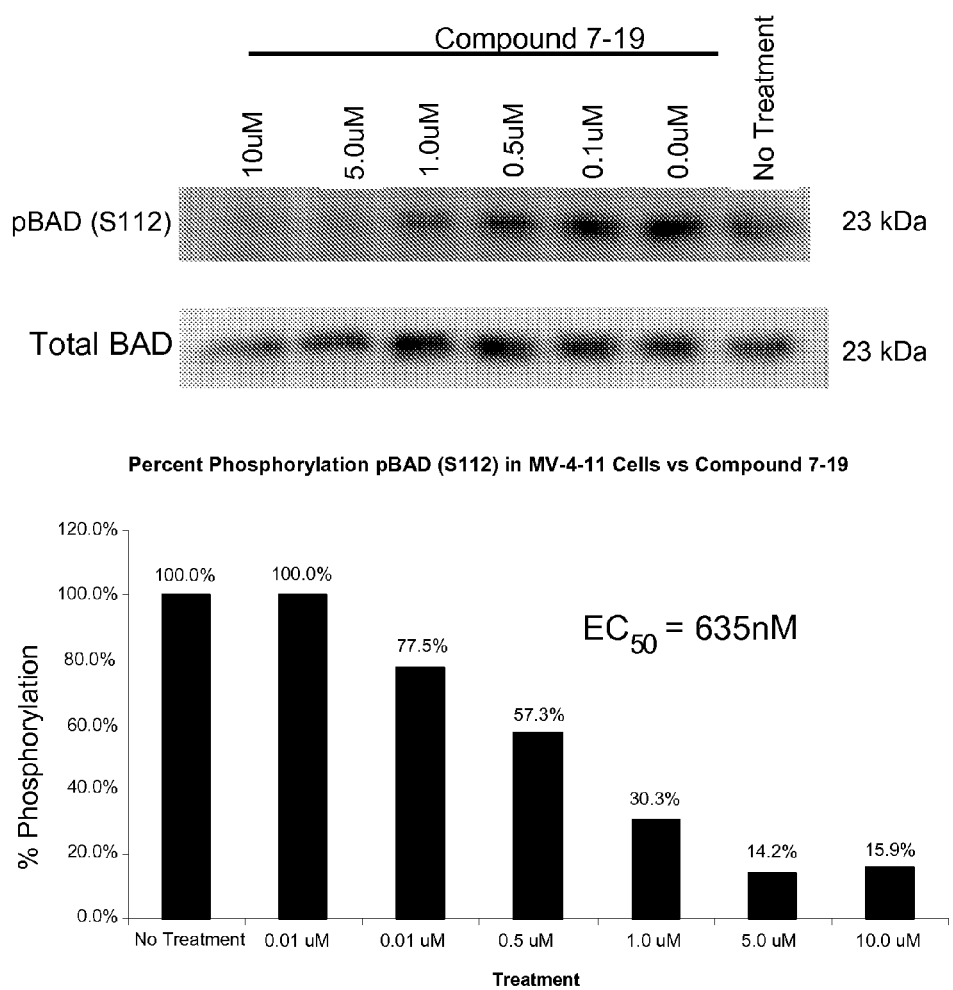
Figure 3. Levels of pBAD and Bad were determined by densitometry analysis of western blots and used to determine the EC50 of Compound 7-19 against MV-4-11 cells.

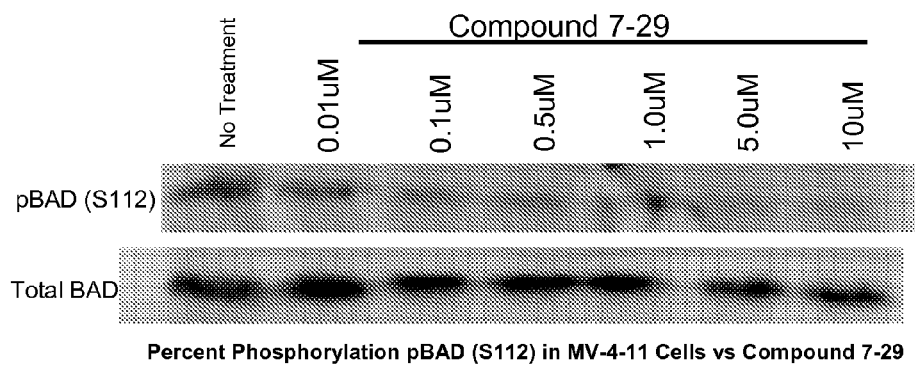
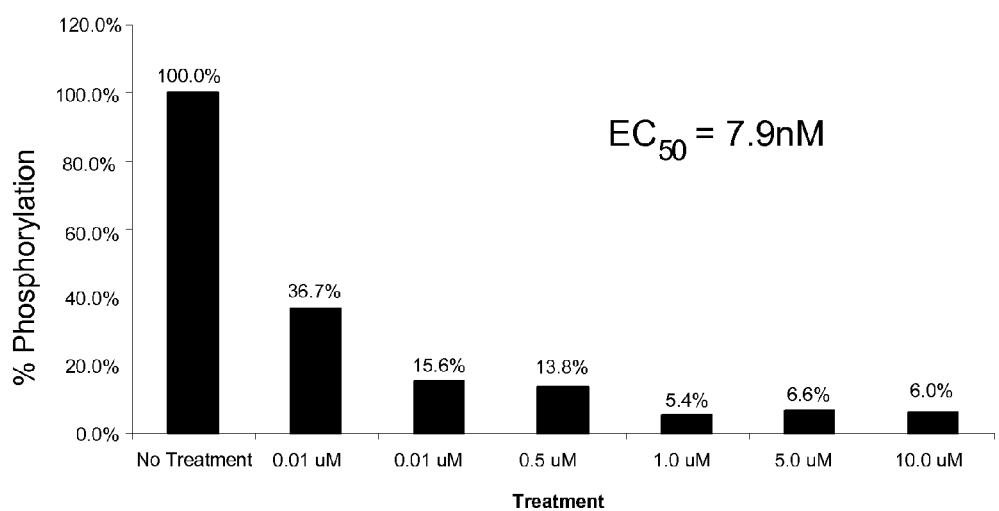
Figure 4. Levels of pBAD and Bad were determined by densitometry analysis of western blots and used to determine the EC50 of Compound 7-29 against MV-4-11 cells.

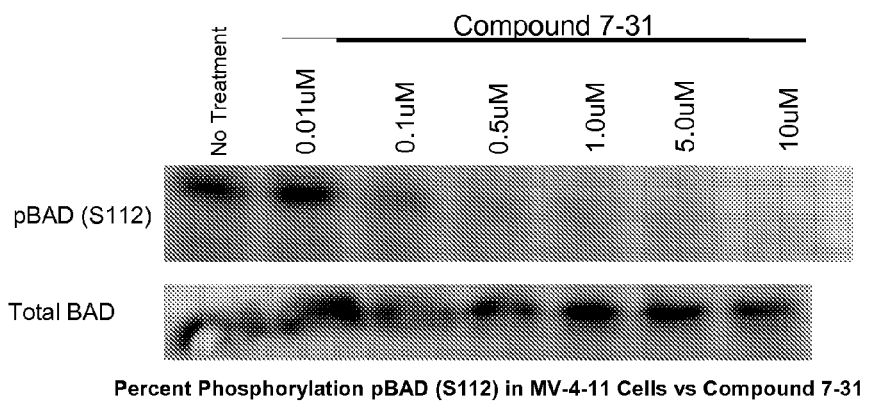
Figure 5. Levels of pBAD and Bad were determined by densitometry analysis of western blots and used to determine the EC50 of Compound 7-31 against MV-4-11 cells.

IMIDAZO[1,2-BETA]PYRIDAZINE AND PYRAZOLO[1,5-ALPHA]PYRIMIDINE DERIVATIVES AND THEIR USE AS PROTEIN KINASE INHIBITORS

CROSS-REFERENCE TO RELATED APPLICATIONS

This application claims the benefit under 35 U.S.C. §119 (e) of U.S. Provisional Patent Application No. 60/864,566, filed Nov. 6, 2006; U.S. Provisional Patent Application No. 60/892,523, filed Mar. 1, 2007; and U.S. Provisional Patent Application No. 60/957,988, filed Aug. 24, 2007, where these three provisional applications are incorporated herein by reference in their entireties.

BACKGROUND OF THE INVENTION

1. Technical Field

The present invention relates, in general, to compounds that inhibit protein kinase activity, and to compositions and methods related thereto.

2. Description of the Related Art

Cancer (and other hyperproliferative diseases) is characterized by uncontrolled cell proliferation. This loss of the normal control of cell proliferation often appears to occur as the result of genetic damage to cell pathways that control progress through the cell cycle. The cell cycle consists of DNA synthesis (S phase), cell division or mitosis (M phase), and non-synthetic periods referred to as gap 1 (G1) and gap 2 (G2). The M-phase is composed of mitosis and cytokinesis (separation into two cells). All steps in the cell cycle are controlled by an orderly cascade of protein phosphorylation and several families of protein kinases are involved in carrying out these phosphorylation steps. In addition, the activity of many protein kinases increases in human tumors compared to normal tissue and this increased activity can be due to many factors, including increased levels of a kinase or changes in expression of co-activators or inhibitory proteins.

Cells have proteins that govern the transition from one phase of the cell cycle to another. For example, the cyclins are a family of proteins whose concentrations increase and decrease throughout the cell cycle. The cyclins turn on, at the appropriate time, different cyclin-dependent protein kinases (CDKs) that phosphorylate substrates essential for progression through the cell cycle. Activity of specific CDKs at specific times is essential for both initiation and coordinated progress through the cell cycle. For example, CDK1 is the most prominent cell cycle regulator that orchestrates M-phase activities. However, a number of other mitotic protein kinases that participate in M-phase have been identified, which include members of the polo, aurora, and NIMA (Never-In-Mitosis-A) families and kinases implicated in mitotic checkpoints, mitotic exit, and cytokinesis.

Pim kinases (e.g., Pim-1 kinase, Pim-2 kinase, Pim-3 kinase) are a family of oncogenic serine/threonine kinases. Pim-1 kinase is known to be involved in a number of cytokine signaling pathways as a downstream effector. Once activated, Pim-1 kinase causes progression of the cell cycle, inhibition of apoptosis and modulation of other signal transduction pathways, including its own. Pim-1 kinase is also known to effect activation of transcription factors such as NFAT, p100, c-Myb and Pap-1, and inhibition of others such as HP1. Normal expression of Pim-1 kinase is seen in cells of hematopoietic origin, such as fetal liver, thymus, spleen and bone marrow. Additionally, expression is seen in prostate and oral epithelial cells Pim-1 kinase is believed to be involved in the initiation or progression of malignant transformation leading to malignancies including Burkitt's lymphoma, prostate cancer, oral cancer and diffuse large cell lymphomas, among others.

Based on their involvement in a number of human malignancies, there is a need for the rational design of specific and selective inhibitors for the treatment of cancer and other conditions that are mediated and/or associated with Pim kinase proteins. The present invention fulfills these needs and offers other related advantages.

BRIEF SUMMARY

The present invention is generally directed to compounds, and pharmaceutical compositions comprising said compounds, where the compounds have the following general structures (I) and (II) below:

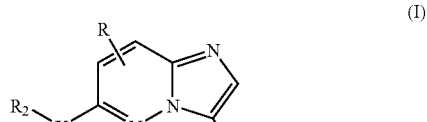

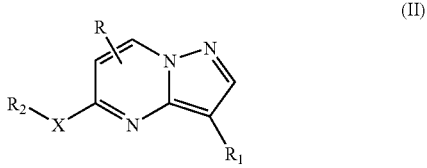

including stereoisomers, prodrugs and pharmaceutically acceptable salts thereof, wherein R, $R_1$, $R_2$ and X are as defined herein.

These compounds of the present invention have utility over a broad range of therapeutic applications, and may be used to treat diseases, such as cancer, that are mediated at least in part by protein kinase activity. Accordingly, in one aspect of the invention, the compounds described herein are formulated as pharmaceutically acceptable compositions for administration to a subject in need thereof.

In another aspect, the invention provides methods for treating or preventing a protein kinase-mediated disease, such as cancer, which method comprises administering to a patient in need of such a treatment a therapeutically effective amount of a compound described herein or a pharmaceutically acceptable composition comprising said compound. In certain embodiments, the protein kinase-mediated disease is a Pim kinase-mediated disease, such as a Pim-1 kinase-expressing cancer.

Another aspect of the invention relates to inhibiting protein kinase activity in a biological sample, which method comprises contacting the biological sample with a compound described herein, or a pharmaceutically acceptable composition comprising said compound. In certain embodiments, the protein kinase is Pim kinase.

Another aspect of this invention relates to a method of inhibiting protein kinase activity in a patient, which method comprises administering to the patient a compound described herein or a pharmaceutically acceptable composition comprising said compound. In certain embodiments, the protein kinase is a Pim kinase.

These and other aspects of the invention will be apparent upon reference to the following detailed description and attached figures. To that end, certain patent and other documents are cited herein to more specifically set forth various aspects of this invention. Each of these documents is hereby incorporated by reference in its entirety.

BRIEF DESCRIPTION OF THE DRAWINGS

FIG. 1 shows Pim-1 kinase inhibitory activity of illustrative compounds.

FIG. 2 shows the results of screening compound 7-29 (Table VII) for selectivity against a panel of Serine/Threonine and Tyrosine kinases in a radiometric assay.

FIGS. 3-5 show the results for the phospho-Bad staining on MV-4-11 cells treated with Compounds 7-19, 7-29, and 7-31, respectively.

DETAILED DESCRIPTION OF THE INVENTION

According to a general aspect of the present invention, there are provided compounds useful as protein kinase inhibitors and compositions and methods relating thereto. Compounds of the invention have structures set forth in (I) or (II) below:

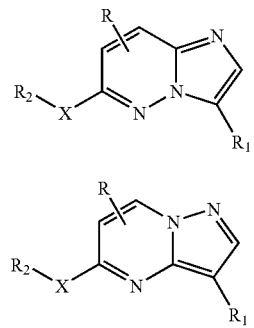

(I)

(II)

including stereoisomers, prodrugs and pharmaceutically acceptable salts thereof, where:

X is NH, S, O, SO or $SO_2$;

R is H, —OH, halo, alkyl, haloalkyl, alkoxy or haloalkoxy;

$R_1$ is carbocycle, substituted carbocycle, heterocycle, or substituted heterocycle; or a structure selected from:

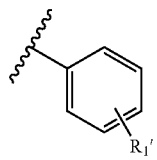

where $R_1'$ is a p, o or m substitution with one or more occurrences of halo, —$OCF_3$, —$OCHF_2$, —$CF_3$, —$OCH_3$, —$NH_2$, —$NO_2$, —OH, —$COCH_3$, —$NHSO_2CH_3$ or —$N(CH_3)_2$.

$R_2$ is —$(CH_2)_n$-cyclopropyl, —$(CH_2)_n$-cyclopentyl, —$(CH_2)_n$-cyclohexyl, —$SO_2$—$CH_3$, —$SO_2$—$(CH_2)_n CH_3$, —$(CH_2)_n$-piperonyl, —$(CH_2)_n$-piperidyl, —$(CH_2)_n$-piperazinyl, —$(CH_2)_n$-furyl, —$(CH_2)_n$-thiophene, —$(CH_2)_n$-pyridyl, —$(CH_2)_n$-pyrimidyl, —$(CH_2)_n OCH_3$, —$(CH_2)_n OH$, or —$(CH_2)_n N(CH_3)_2$, where n is 0, 1, 2, 3 or 4 and each of the above moieties are optionally substituted with one or more substituents; or a structure selected from:

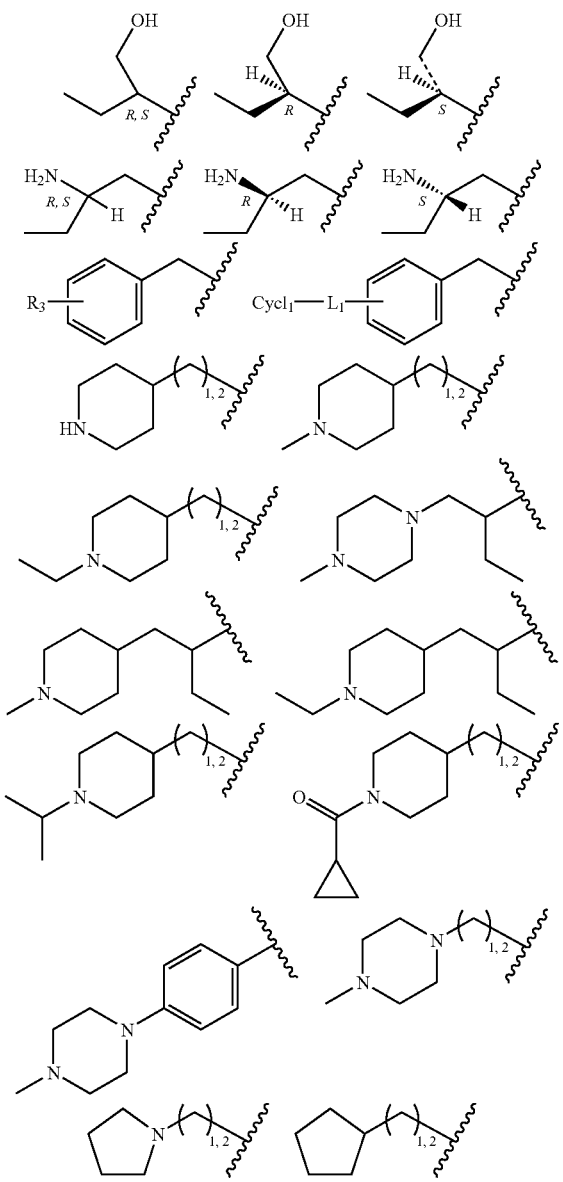

where L is optional and, if present, NH, S, O, SO or $SO_2$; $R_3$ is one or more optional substituents; and $Cycl_1$ is a carbocycle, substituted carbocycle, heterocycle or substituted heterocycle.

Unless otherwise stated the following terms used in the specification and claims have the meanings discussed below:

"Alkyl" refers to a saturated straight or branched hydrocarbon radical of one to six carbon atoms, preferably one to four carbon atoms, e.g., methyl, ethyl, propyl, 2-propyl, n-butyl, iso-butyl, tert-butyl, pentyl, hexyl, and the like, preferably methyl, ethyl, propyl, or 2-propyl. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —$CH_2$-cyclohexyl, and the like; while unsaturated cyclic alkyls include cyclopentenyl, cyclohexenyl, —$CH_2$-cyclohexenyl, and the like. Cyclic alkyls are also referred to herein as a "cycloalkyl." Unsaturated alkyls contain at least one double or triple bond between adjacent carbon atoms (referred to as an "alkenyl" or "alkynyl", respectively.) Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like, preferably methylene, ethylene, or propylene.

"Cycloalkyl" refers to a saturated cyclic hydrocarbon radical of three to eight carbon atoms, e.g., cyclopropyl, cyclobutyl, cyclopentyl or cyclohexyl.

"Alkoxy" means a radical —OR$_a$ where R$_a$ is an alkyl as defined above, e.g., methoxy, ethoxy, propoxy, butoxy and the like.

"Halo" means fluoro, chloro, bromo, or iodo, preferably fluoro and chloro.

"Haloalkyl" means alkyl substituted with one or more, preferably one, two or three, same or different halo atoms, e.g., —CH$_2$Cl, —CF$_3$, —CH$_2$CF$_3$, —CH$_2$CCl$_3$, and the like.

"Haloalkoxy" means a radical —OR$_b$ where R$_b$ is an haloalkyl as defined above, e.g., trifluoromethoxy, trichloroethoxy, 2,2-dichloropropoxy, and the like.

"Acyl" means a radical —C(O)R$_c$, where R$_c$ is hydrogen, alkyl, or haloalkyl as defined herein, e.g., formyl, acetyl, trifluoroacetyl, butanoyl, and the like.

"Aryl" refers to an all-carbon monocyclic or fused-ring polycyclic (i.e., rings which share adjacent pairs of carbon atoms) groups of 6 to 12 carbon atoms having a completely conjugated pi-electron system. Examples, without limitation, of aryl groups are phenyl, naphthyl and anthracenyl. The aryl group may be substituted or unsubstituted. When substituted, the aryl group is substituted with one or more substituents as this term is defined below, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, phenoxy, heteroaryl, heteroaryloxy, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, triazole, tetrazole, triazine, and carbazole. The heteroaryl group may be substituted or unsubstituted. When substituted, the heteroaryl group is substituted with one or more substituents as this term is defined below, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Carbocycle" refers to a saturated, unsaturated or aromatic ring system having 3 to 14 ring carbon atoms. The term "carbocycle", whether saturated or partially unsaturated, also refers to rings that are optionally substituted. The term "carbocycle" includes aryl. The term "carbocycle" also includes aliphatic rings that are fused to one or more aromatic or nonaromatic rings, such as in a decahydronaphthyl or tetrahydronaphthyl, where the radical or point of attachment is on the aliphatic ring. The carbocycle group may be substituted or unsubstituted. When substituted, the carbocycle group is substituted with one or more substituents as this term is defined below, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Heterocycle" refers to a saturated, unsaturated or aromatic cyclic ring system having 3 to 14 ring atoms in which one, two or three ring atoms are heteroatoms selected from N, O, or S(O)$_m$ (where m is an integer from 0 to 2), the remaining ring atoms being C, where one or two C atoms may optionally be replaced by a carbonyl group. The term "heterocycle" includes heteroaryl. The heterocyclyl ring may be optionally substituted independently with one or more substituents as this term is defined below, preferably one, two, or three substituents selected from alkyl (wherein the alkyl may be optionally substituted with one or two substituents), haloalkyl, cycloalkylamino, cycloalkylalkyl, cycloalkylaminoalkyl, cycloalkylalkylaminoalkyl, cyanoalkyl, halo, nitro, cyano, hydroxy, alkoxy, amino, alkylamino, dialkylamino, hydroxyalkyl, carboxyalkyl, aminoalkyl, alkylaminoalkyl, dialkylaminoalkyl, aralkyl, heteroaralkyl, aryl, heteroaryl, carbocycle, heterocycle (wherein the aryl, heteroaryl, carbocycle or heterocycle may be optionally substituted), aralkyl, heteroaralkyl, saturated or unsaturated heterocycloamino, saturated or unsaturated heterocycloaminoalkyl, and —COR$_d$ (where R$_d$ is alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, pyrrolidino, morpholino, 4-cyclopropylmethylpiperazino, thiomorpholino, thiomorpholino-1-oxide, thiomorpholino-1,1-dioxide, 4-ethyloxycarbonylpiperazino, 3-oxopiperazino, 2-imidazolidone, 2-pyrrolidinone, 2-oxohomopiperazino, tetrahydropyrimidin-2-one, and the derivatives thereof. In certain embodiments, the heterocycle group is optionally substituted with one or two substituents independently selected from halo, alkyl, alkyl substituted with carboxy, ester, hydroxy, alkylamino, saturated or unsaturated heterocycloamino, saturated or unsaturated heterocycloaminoalkyl, or dialkylamino.

"Optional" or "optionally" means that the subsequently described event or circumstance may but need not occur, and that the description includes instances where the event or circumstance occurs and instances in which it does not. For example, "heterocyclic group optionally substituted with an alkyl group" means that the alkyl may but need not be present, and the description includes situations where the heterocycle group is substituted with an alkyl group and situations where the heterocycle group is not substituted with the alkyl group.

Lastly, the term "substituted" as used herein means any of the above groups (e.g., alkyl, aryl, heteroaryl, carbocycle, heterocycle, etc.) wherein at least one hydrogen atom is replaced with a substituent. In the case of an oxo substituent ("=O") two hydrogen atoms are replaced. "Substituents" within the context of this invention include halogen, hydroxy, oxo, cyano, nitro, amino, alkylamino, dialkylamino, alkyl, alkoxy, thioalkyl, haloalkyl, hydroxyalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —$NR_eR_f$, —$NR_eC(=O)R_f$, —$NR_eC(=O)NR_eR_f$, —$NR_eC(=O)OR_f$, —$NR_eSO_2R_f$, —$OR_e$, —$C(=O)R_e$, —$C(=O)OR_e$, —$C(=O)NR_eR_f$, —$OC(=O)NR_eR_f$, —SH, —$SR_e$, —$SOR_e$, —$S(=O)NH_2$, —$S(=O)_2R_e$, —$OS(=O)_2R_e$, —$S(=O)_2OR_e$, wherein $R_e$ and $R_f$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

Certain illustrative compounds according to structures (I) and (II), for use as described herein, are set forth below.

In a more specific aspect of structures (I) and (II) above, $R_1$ is a 5-6 membered saturated, partially unsaturated, or fully unsaturated monocyclic ring having 0-3 heteroatoms, where the heteroatoms are selected from nitrogen, oxygen and sulfur.

In a more specific aspect of structures (I) and (II) above, $R_1$ is p, or m substituted phenyl with one or more occurrences of —F, —Cl, —$CF_3$, —$OCF_3$, —$OCH_3$, —$CH_3$, $NO_2$, —$N(CH_3)_2$, —$NH_2$, —$NHSO_2CH_3$, —$NHSO_2CH_2CH_3$, —$COCH_3$, —COOH, —$CH_2NH_2$, —OH, —$SO_2NH_2$, —$SCH_3$, piperazine or morpholine.

In a more specific aspect of structures (I) and (II) above, $R_1$ is an optionally substituted pyrazolyl, furyl, thiophene, pyridyl, pyrimidyl, or indolyl group.

In a more specific aspect of structures (I) and (II) above, $R_1$ has the structure:

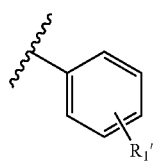

where $R_1'$ represents one or more optional substituents or, in a more specific embodiment, is a p, o or m substitution with one or more occurrences of halo. —$OCF_3$, —$CF_3$, —$OCH_3$, —$OCHF_2$, $NH_2$, $NO_2$, OH, —$COCH_3$, —$NHSO_2CH_3$, or —$N(CH_3)_2$.

In a more specific aspect of structures (I) and (II) above, $R_2$ is 2-butane-1-ol, —$SO_2CH_3$, —$SO_2CH_2CH_3$, —$CH_2CH_2OCH_3$, —$CH_2CH_2CH_2OH$, or —$CH_2CH_2N(CH_3)_2$.

In a more specific aspect of structures (I) and (II) above, $R_2$ is optionally substituted —$(CH_2)_n$-cyclopropyl, —$(CH_2)_n$-cyclopentyl, —$(CH_2)_n$-cyclohexyl, —$(CH_2)_n$-piperonyl, —$(CH_2)_n$-piperidyl, —$(CH_2)_n$-piperazinyl, —$(CH_2)_n$-furyl, —$(CH_2)_n$-thiophene, —$(CH_2)_n$-pyridyl, or —$(CH_2)_n$-pyrimidyl.

In a more specific aspect of structures (I) and (II) above, $R_2$ has a structure selected from:

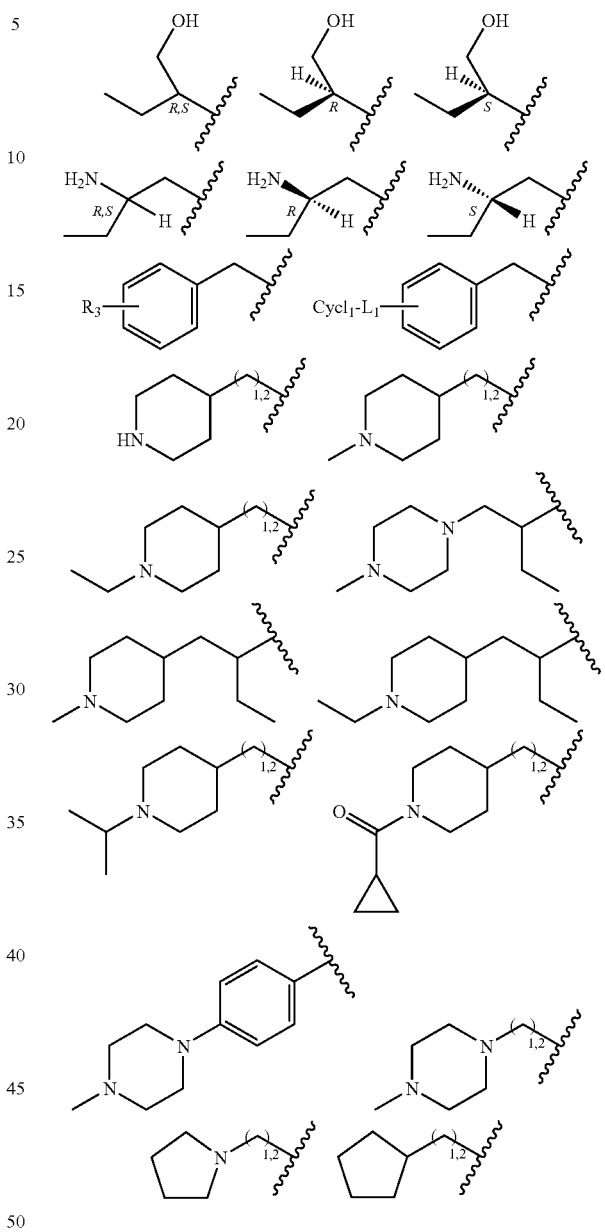

where L is optional and, if present, NH, S, O, SO or $SO_2$; $R_3$ is one or more optional substituents; and $Cycl_1$ is a carbocycle, substituted carbocycle, heterocycle or substituted heterocycle.

In a more specific aspect of structures (I) and (II) above, $R_2$ has the following structure:

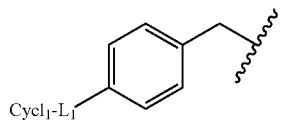

where L is optional and, if present, NH, S, O, SO or $SO_2$; and $Cycl_1$ is a carbocycle, substituted carbocycle, heterocycle or substituted heterocycle, and in a more specific embodiment Cyc1₁ is a 5-6 membered saturated, partially unsaturated, or fully unsaturated monocyclic ring having 0-3 heteroatoms, where the heteroatoms are selected from nitrogen, oxygen and sulfur.

In a more specific aspect of structures (I) and (II) above, $R_2$ has a structure selected from:

In further specific embodiments of structures (I) and (II), X is NH and $R_1$ is a substituted or unsubstituted phenyl (where R is as defined above and $R_1'$ is absent or represents one or more substituents), and the compounds have the following structures (I-A) and (II-A), respectively:

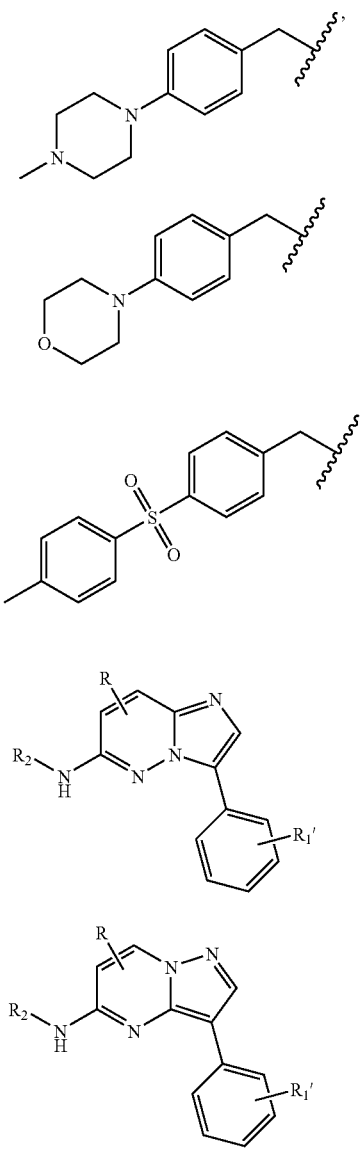

(I-A)

(II-A)

or a stereoisomer, prodrug or pharmaceutically acceptable salt thereof.

In more specific embodiments of (I-A) and (II-A), R is alky, such as methyl, and the compounds have the following structures (I-Aa) and (II-Aa):

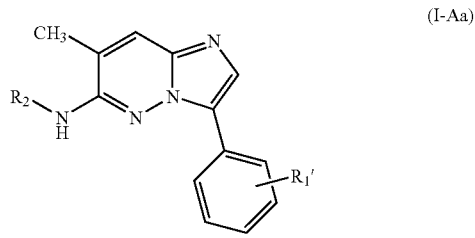

(I-Aa)

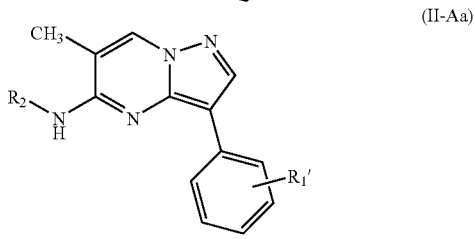

(II-Aa)

or a stereoisomer, prodrug or pharmaceutically acceptable salt thereof.

In more specific embodiments of (I-A), (II-A), (I-Aa) and (II-Aa), $R_1$ is substituted phenyl having at least one p, o or m substituent selected from halo. —OCF₃, —OCHF₂, —CF₃, —OCH₃, —NH₂, —NO₂, —OH, —COCH₃, —NHSO₂CH₃ and —N(CH₃)₂, and in an more specific embodiment $R_1$ is substituted phenyl having at least one p, o or m substituent selected from —OCF₃, —OCHF₂, —CF₃, —OCH₃ and —OH, and in a more specific embodiment $R_1$ is selected from:

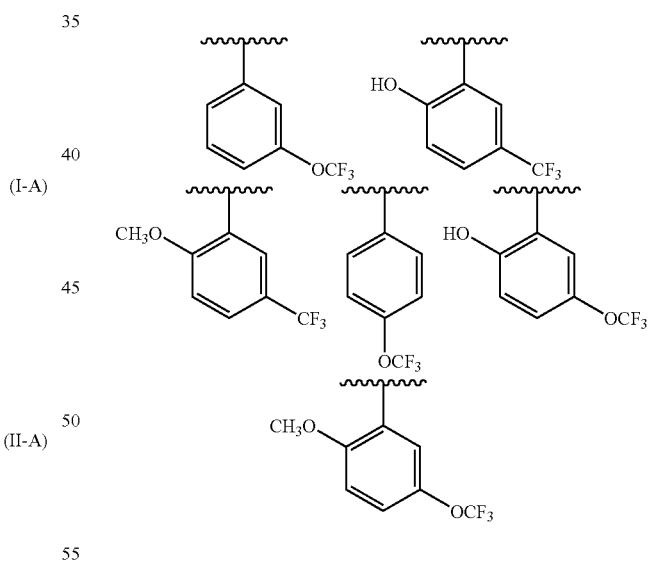

In more specific embodiments of (I-A), (II-A), (I-Aa) and (II-Aa), $R_2$ is —(CH₂)₁,₂-piperid-4-yl, substituted —(CH₂)₁,₂-piperid-4-yl, —(CH₂)₁,₂-piperazin-1-yl, or substituted —(CH₂)₁,₂-piperazin-1-yl, such as moiety selected from:

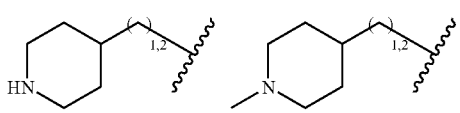

-continued

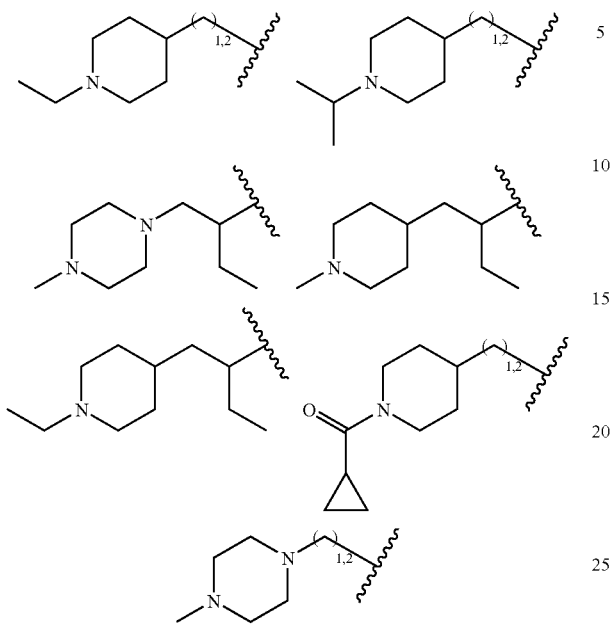

More specifically R$_2$ is selected from:

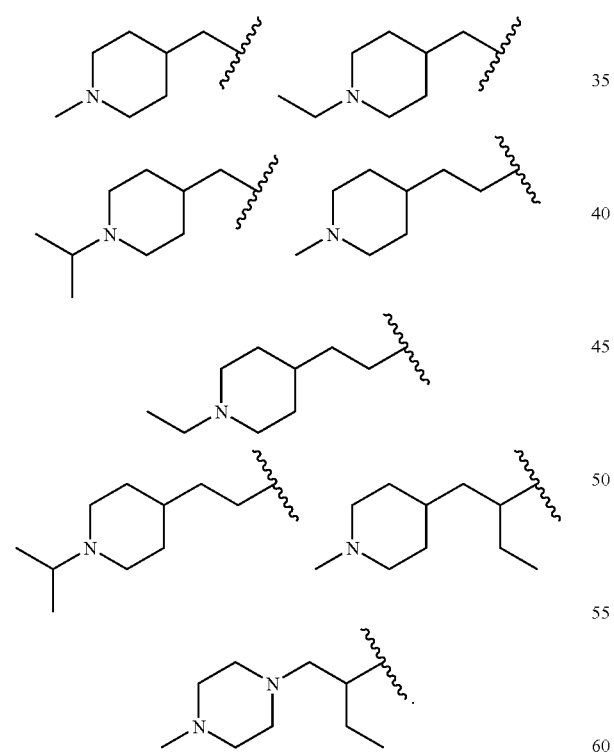

In still further specific embodiments of structures (I) and (II), X is O and R$_1$ is a substituted or unsubstituted phenyl (where R is as defined above and R$_1$' is absent or represents one or more substituents), and the compounds have the following structures (I-B) and (II-B), respectively:

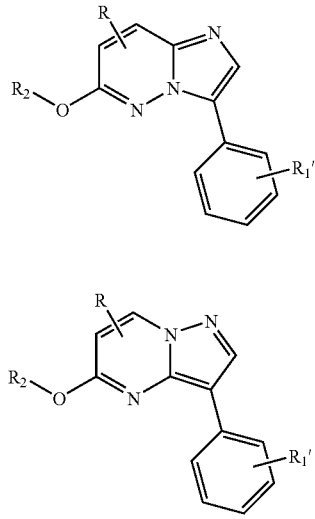

or a stereoisomer, prodrug or pharmaceutically acceptable salt thereof.

In more specific embodiments of (I-B) and (II-B), R is alky, such as methyl, and the compounds have the following structures (I-Bb) and (II-Bb):

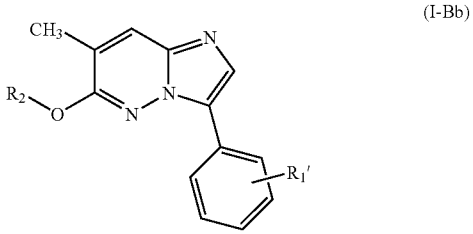

or a stereoisomer, prodrug or pharmaceutically acceptable salt thereof.

In more specific embodiments of (I-B), (II-B), (I-Bb) and (IIB-b), R$_1$ is substituted phenyl having at least one p, o or m substituent selected from halo. —OCF$_3$, —OCHF$_2$, —CF$_3$, —OCH$_3$, —NH$_2$, —NO$_2$, —OH, —COCH$_3$, —NHSO$_2$CH$_3$ and —N(CH$_3$)$_2$, and in an more specific embodiment R$_1$ is substituted phenyl having at least one p, o or m substituent selected from —OCF$_3$, —OCHF$_2$, —CF$_3$, —OCH$_3$ and —OH, and in a more specific embodiment R$_1$ is selected from:

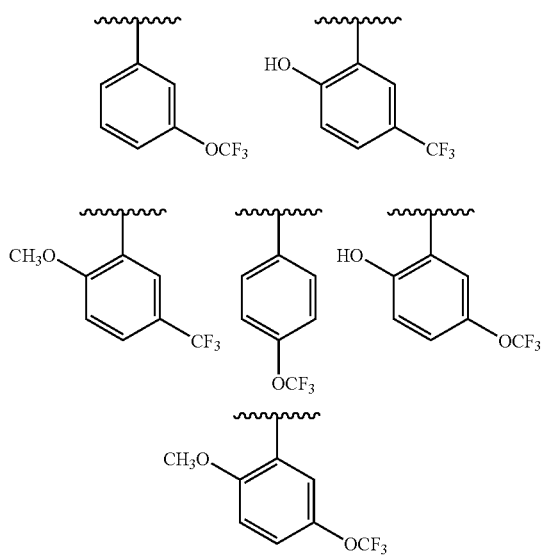

In more specific embodiments of structures (I-B), (II-B), (I-Bb) and (II-Bb), $R_2$ is —$(CH_2)_n$-cyclopropyl, —$(CH_2)_n$-cyclopentyl, —$(CH_2)_n$-cyclohexyl, —$SO_2$—$CH_3$, —$SO_2$—$(CH_2)_nCH_3$, —$(CH_2)_n$-piperonyl, —$(CH_2)_n$-piperidyl, —$(CH_2)_n$-piperazinyl, —$(CH_2)_n$-furyl, —$(CH_2)_n$-thiophene, —$(CH_2)_n$-pyridyl, —$(CH_2)_n$-pyrimidyl, —$(CH_2)_nOCH_3$, —$(CH_2)_nOH$, or —$(CH_2)_nN(CH_3)_2$, where n is 0, 1, 2, 3 or 4 and each of the above moieties are optionally substituted with one or more substituents; or a structure selected from:

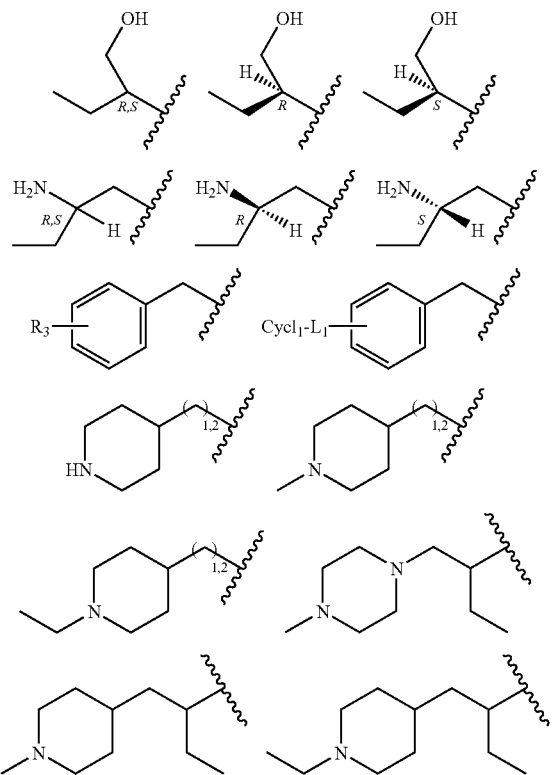

In more specific embodiments of (I-B), (II-B), (I-Bb) and (II-Bb), $R_2$ is —$(CH_2)_{1,2}$-piperid-4-yl, substituted —$(CH_2)_{1,2}$-piperid-4-yl, —$(CH_2)_{1,2}$-piperazin-1-yl, or substituted —$(CH_2)_{1,2}$-piperazin-1-yl, such as moiety selected from:

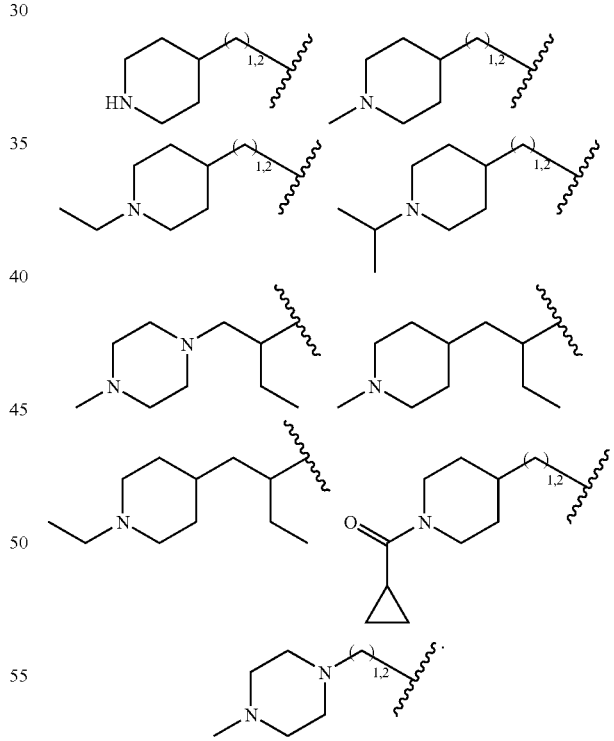

More specifically $R_2$ is selected from:

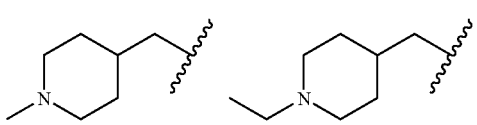

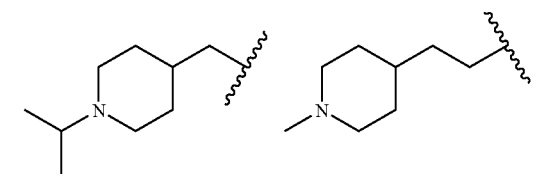
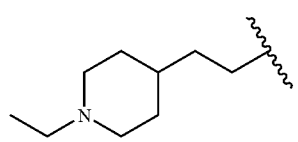
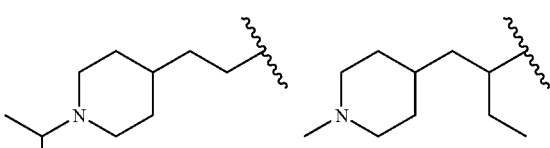
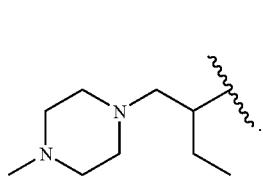

In yet further specific embodiments of structures (I) and (II), X is S, SO or SO$_2$ and R$_1$ is a substituted or unsubstituted phenyl (where R$_1$' below is absent or represents one or more substituents), and the compounds have the following structures (I-C) and (II-C), respectively:

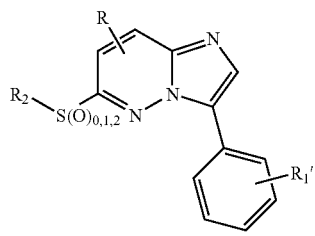

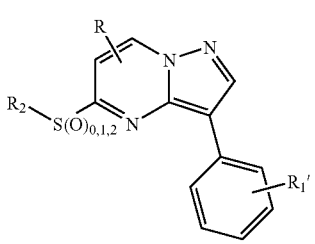

or a stereoisomer, prodrug or pharmaceutically acceptable salt thereof.

In more specific embodiments of (I-C) and (II-C), R is alky, such as methyl, and the compounds have the following structures (I-Cc) and (II-Cc):

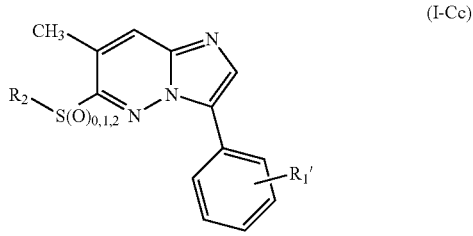

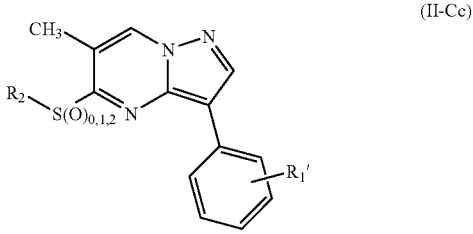

or a stereoisomer, prodrug or pharmaceutically acceptable salt thereof.

In more specific embodiments of (I-C), (II-C), (I-Cc) and (II-Cc), R$_1$ is substituted phenyl having at least one p, o or m substituent selected from halo. —OCF$_3$, —OCHF$_2$, —CF$_3$, —OCH$_3$, —NH$_2$, —NO$_2$, —OH, —COCH$_3$, —NHSO$_2$CH$_3$ and —N(CH$_3$)$_2$, and in an more specific embodiment R$_1$ is substituted phenyl having at least one p, o or m substituent selected from —OCF$_3$, —OCHF$_2$, —CF$_3$, —OCH$_3$ and —OH, and in a more specific embodiment R$_1$ is selected from:

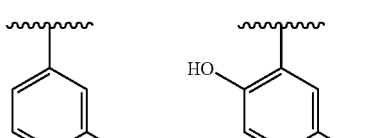
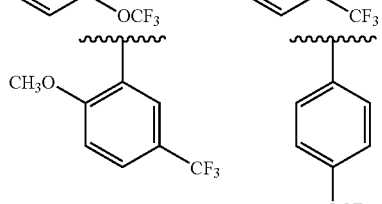
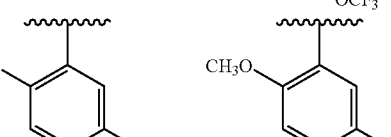

In more specific embodiments of structures (I-C), (II-C), (I-Cc) and (II-Cc), R$_2$ is —(CH$_2$)$_n$-cyclopropyl, —(CH$_2$)$_n$-cyclopentyl, —(CH$_2$)$_n$-cyclohexyl, —SO$_2$—CH$_3$, —SO$_2$—(CH$_2$)$_n$CH$_3$, —(CH$_2$)$_n$-piperonyl, —(CH$_2$)$_n$-piperidyl, —(CH$_2$)$_n$-piperazinyl, —(CH$_2$)$_n$-furyl, —(CH$_2$)$_n$-thiophene, —(CH$_2$)$_n$-pyridyl, —(CH$_2$)$_n$-pyrimidyl, —(CH$_2$)$_n$OCH$_3$, —(CH$_2$)$_n$OH, or —(CH$_2$)$_n$N(CH$_3$)$_2$, where n is 0, 1, 2, 3 or 4 and each of the above moieties are optionally substituted with one or more substituents; or a structure selected from:

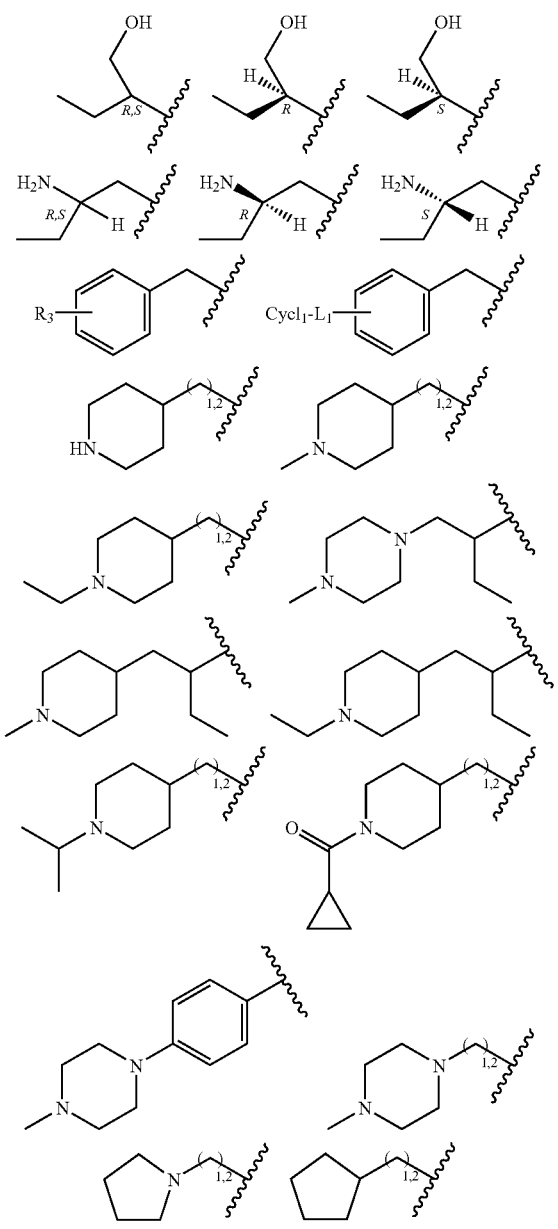

In more specific embodiments of (I-C), (II-C), (I-Cc) and (II-Cc), $R_2$ is —$(CH_2)_{1,2}$-piperid-4-yl, substituted —$(CH_2)_{1,2}$-piperid-4-yl, —$(CH_2)_{1,2}$-piperazin-1-yl, or substituted —$(CH_2)_{1,2}$-piperazin-1-yl, such as moiety selected from:

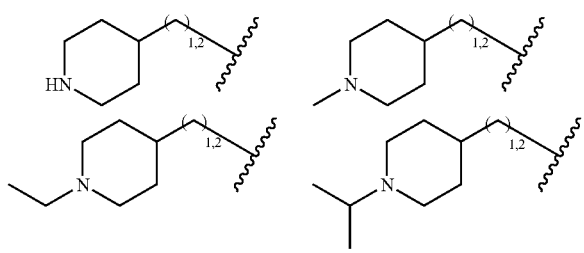

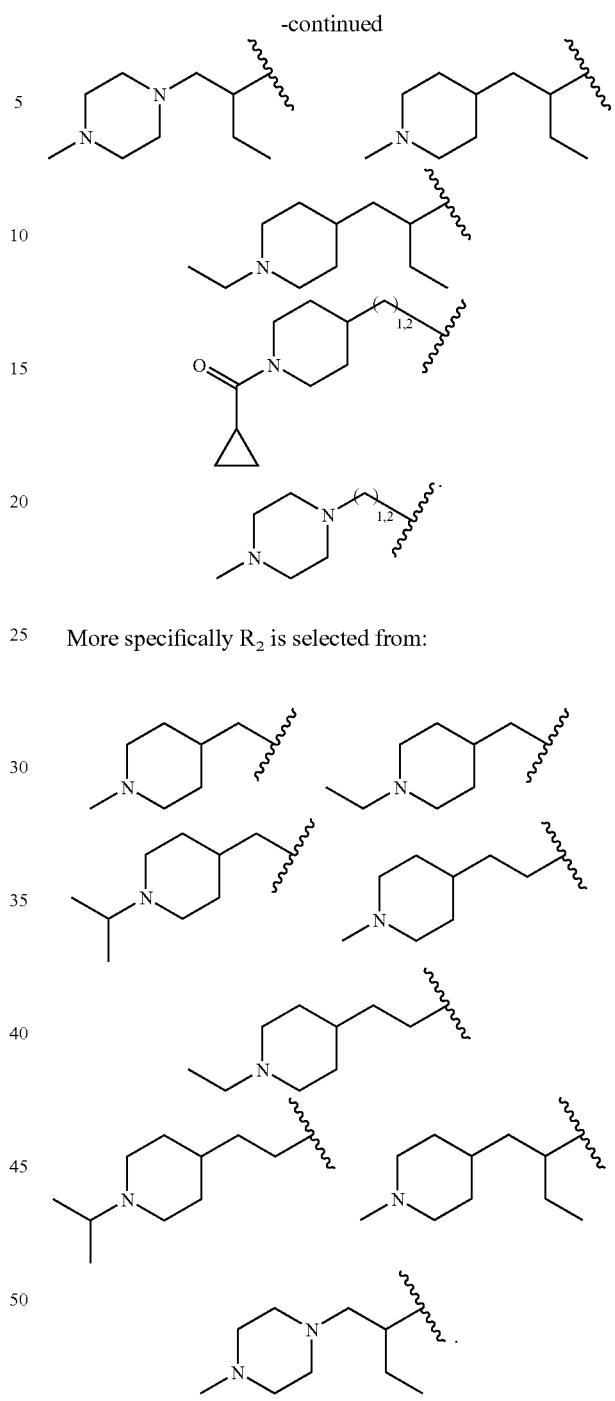

More specifically $R_2$ is selected from:

In more specific aspects of structure (I) above, the compound has a structure set forth in Table II (Compounds 2-1 to 2-22).

In more specific aspects of structure (II) above, the compound has a structure set forth in Table III (Compounds 3-1 to 3-13).

In more specific aspects of structure (II) above, compounds are provided having structures set forth in Table IV (Compounds 4-1 to 4-22).

In more specific aspects of structure (I) above, compounds are provided having structures set forth in Table VII (Compounds 7-1 to 7-51).

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog (Cahn, R., Ingold, C., and Prelog, V. Angew. Chem. 78:413-47, 1966; Angew. Chem. Internat. Ed. Eng. 5:385-415, 511, 1966), or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Ch. 4 of ADVANCED ORGANIC CHEMISTRY, 4$^{th}$ edition, March, J., John Wiley and Sons, New York City, 1992).

The compounds of the present invention may exhibit the phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof which possess the ability to modulate aurora-2 kinase activity and is not limited to, any one tautomeric or structural isomeric form.

It is contemplated that a compound of the present invention would be metabolized by enzymes in the body of the organism such as human being to generate a metabolite that can modulate the activity of the protein kinases. Such metabolites are within the scope of the present invention.

A compound of the present invention or a pharmaceutically acceptable salt thereof, can be administered as such to a human patient or can be administered in pharmaceutical compositions in which the foregoing materials are mixed with suitable carriers or excipient(s). Techniques for formulation and administration of drugs may be found, for example, in REMINGTON'S PHARMACOLOGICAL SCIENCES, Mack Publishing Co., Easton, Pa., latest edition.

A "pharmaceutical composition" refers to a mixture of one or more of the compounds described herein, or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts which retain the biological effectiveness and properties of the parent compound. Such salts may include: (1) acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D)- or (L)-malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compound of the present invention may also act, or be designed to act, as a prodrug. A "prodrug" refers to an agent, which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention, which is, administered as an ester (the "prodrug"), phosphate, amide, carbamate or urea.

"Therapeutically effective amount" refers to that amount of the compound being administered which will relieve to some extent one or more of the symptoms of the disorder being treated. In reference to the treatment of cancer, a therapeutically effective amount refers to that amount which has the effect of: (1) reducing the size of the tumor; (2) inhibiting tumor metastasis; (3) inhibiting tumor growth; and/or (4) relieving one or more symptoms associated with the cancer.

The term "protein kinase-mediated condition" or "disease", as used herein, means any disease or other deleterious condition in which a protein kinase is known to play a role. The term "protein kinase-mediated condition" or "disease" also means those diseases or conditions that are alleviated by treatment with a protein kinase inhibitor. Such conditions include, without limitation, cancers which express Pim kinases, particularly Pim-1 kinase, and other hyperproliferative disorders associated with Pim kinase expression. In certain embodiments, the cancer is a cancer of colon, breast, stomach, prostate, pancreas, or ovarian tissue.

The term "Pim kinase-mediated condition" or "disease", as used herein, means any disease or other deleterious condition in which Pim 1 kinase, Pim 2 Kinase and/or Pim 3 kinase is known to be expressed and/or play a role. The term "Pim kinase-mediated condition" or "disease" also means those diseases or conditions that are alleviated by treatment with an Pim kinase inhibitor.

As used herein, "administer" or "administration" refers to the delivery of an inventive compound or of a pharmaceutically acceptable salt thereof or of a pharmaceutical composition containing an inventive compound or a pharmaceutically acceptable salt thereof of this invention to an organism for the purpose of prevention or treatment of a protein kinase-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. In certain embodiments, the preferred routes of administration are oral and intravenous.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. In this way, the liposomes may be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in any conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also. Pharmaceutical compositions which may also be used include hard gelatin capsules. The capsules or pills may be packaged into brown glass or plastic bottles to protect the active compound from light. The containers containing the active compound capsule formulation are preferably stored at controlled room temperature (15-30° C.).

For administration by inhalation, the compounds for use according to the present invention may be conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD cosolvent system. VPD is a solution of 3% w/v benzyl alcohol, 8% w/v of the nonpolar surfactant polysorbate 80, and 65% w/v polyethylene glycol 300, made up to volume in absolute ethanol. The VPD cosolvent system (VPD:D5W) consists of VPD diluted 1:1 with a 5% dextrose in water solution. This cosolvent system dissolves hydrophobic compounds well, and itself produces low toxicity upon systemic administration. Naturally, the proportions of such a cosolvent system may be varied considerably without destroying its solubility and toxicity characteristics. Furthermore, the identity of the cosolvent components may be varied: for example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the protein kinase-modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, malate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), calcium hydroxide ($Ca(OH)_2$), etc.).

Pharmaceutical compositions suitable for use in the present invention include compositions wherein the active ingredients are contained in an amount sufficient to achieve the intended purpose, e.g., the modulation of protein kinase activity and/or the treatment or prevention of a protein kinase-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the protein kinase activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See, e.g., GOODMAN & GILMAN'S THE PHARMACOLOGICAL BASIS OF THERAPEUTICS, Ch. 3, $9^{th}$ ed., Ed. by Hardman, J., and Limbard, L., McGraw-Hill, New York City, 1996, p. 46.)

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50-90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%.

At present, the therapeutically effective amounts of compounds of the present invention may range from approximately 2.5 $mg/m^2$ to 1500 $mg/m^2$ per day. Additional illustrative amounts range from 0.2-1000 mg/qid, 2-500 mg/qid, and 20-250 mg/qid.

In cases of local administration or selective uptake, the effective local concentration of the drug may not be related to plasma concentration, and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

As mentioned above, the compounds and compositions of the invention will find utility in a broad range of diseases and conditions mediated by protein kinases, including diseases and conditions mediated by aurora-2 kinase. Such diseases may include by way of example and not limitation, cancers such as lung cancer, NSCLC (non small cell lung cancer), oat-cell cancer, bone cancer, pancreatic cancer, skin cancer, dermatofibrosarcoma protuberans, cancer of the head and neck, cutaneous or intraocular melanoma, uterine cancer, ovarian cancer, colo-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, solid tumors of childhood, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (pre-malignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, angiogenesis, cardiovascular disease such as atherosclerosis, immunological disease such as autoimmune disease and renal disease.

The inventive compound can be used in combination with one or more other chemotherapeutic agents. The dosage of the inventive compounds may be adjusted for any drug-drug reaction. In one embodiment, the chemotherapeutic agent is selected from the group consisting of mitotic inhibitors, alkylating agents, anti-metabolites, cell cycle inhibitors, enzymes, topoisomerase inhibitors such as CAMPTOSAR (irinotecan), biological response modifiers, anti-hormones, antiangiogenic agents such as MMP-2, MMP-9 and COX-2 inhibitors, anti-androgens, platinum coordination complexes (cisplatin, etc.), substituted ureas such as hydroxyurea; methylhydrazine derivatives, e.g., procarbazine; adrenocortical suppressants, e.g., mitotane, aminoglutethimide, hormone and hormone antagonists such as the adrenocorticosteriods (e.g., prednisone), progestins (e.g., hydroxyprogesterone caproate), estrogens (e.g., diethylstilbesterol), antiestrogens such as tamoxifen, androgens, e.g., testosterone propionate, and aromatase inhibitors, such as anastrozole, and AROMASIN (exemestane).

Examples of alkylating agents that the above method can be carried out in combination with include, without limitation, fluorouracil (5-FU) alone or in further combination with leukovorin; other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite chemotherapeutic agents that the above method can be carried out in combination with include, without limitation, folic acid analogs, e.g., methotrexate (used in the treatment of acute lymphocytic leukemia, choriocarcinoma, mycosis fungiodes, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

Examples of natural product-based chemotherapeutic agents that the above method can be carried out in combination with include, without limitation, the vinca alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

Examples of useful COX-II inhibitors include Vioxx, CELEBREX (celecoxib), valdecoxib, paracoxib, rofecoxib, and Cox 189.

Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and compounds selected from: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3- carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methylbenzyloxy)-benzenesulfonyl]-3-hydroxy-3-methyl-piperidine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of these compounds.

Other anti-angiogenesis agents, other COX-II inhibitors and other MMP inhibitors, can also be used in the present invention.

An inventive compound can also be used with other signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, such as HERCEPTIN (Genentech, Inc., South San Francisco, Calif.). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein.

EGFR-inhibiting agents include, but are not limited to, the monoclonal antibodies C225 and anti-EGFR 22Mab (ImClone Systems, Inc., New York, N.Y.), the compounds ZD-1839 (AstraZeneca), BIBX-1382 (Boehringer Ingelheim), MDX-447 (Medarex Inc., Annandale, N.J.), and OLX-103 (Merck & Co., Whitehouse Station, N.J.), and EGF fusion toxin (Seragen Inc., Hopkinton, Mass.).

These and other EGFR-inhibiting agents can be used in the present invention. VEGF inhibitors, for example SU-5416 and SU-6668 (Sugen Inc., South San Francisco, Calif.), can also be combined with an inventive compound. VEGF inhibitors are described in, for example, WO 01/60814 A3 (published Aug. 23, 2001), WO 99/24440 (published May 20, 1999), PCT International Application PCT/IB99/00797 (filed May 3, 1999), WO 95/21613 (published Aug. 17, 1995), WO 99/61422 (published Dec. 2, 1999), U.S. Pat. No. 5,834,504 (issued Nov. 10, 1998), WO 01/60814, WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc., Kirkland, Wash.); anti-VEGF monoclonal antibody of Genentech, Inc.; and angiozyme, a synthetic ribozyme from Ribozyme (Boulder, Colo.) and Chiron (Emeryville, Calif.). These and other VEGF inhibitors can be used in the present invention as described herein. pErbB2 receptor inhibitors, such as GW-282974 (Glaxo Wellcome pic), and the monoclonal antibodies AR-209 (Aronex Pharmaceuticals Inc., The Woodlands, Tex.) and 2B-1 (Chiron), can furthermore be combined with an inventive compound, for example, those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Pat. No. 6,284,764 (issued Sep. 4, 2001), incorporated in its entirety herein by reference. The erbB2 receptor inhibitor compounds and substance described in the aforementioned PCT applications, U.S. patents, and U.S. provisional applications, as well as other compounds and substances that inhibit the erbB2 receptor, can be used with an inventive compound, in accordance with the present invention.

An inventive compound can also be used with other agents useful in treating cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, of U.S. Pat. No. 6,258,824 B1.

The above method can also be carried out in combination with radiation therapy, wherein the amount of an inventive compound in combination with the radiation therapy is effective in treating the above diseases.

Techniques for administering radiation therapy are known in the art, and these techniques can be used in the combination therapy described herein. The administration of the compound of the invention in this combination therapy can be determined as described herein.

The invention will be further understood upon consideration of the following non-limiting Examples.

EXAMPLES

Example 1

Computational-Based Lead Identification

Virtual screening calculations (Friesner et al. *J. Med. Chem.* 47, 1739-1749, 2004; Schrodinger. L. L. C., New York (http://www.schrodinger.com); Schrodinger LLC. *First Discovery Technical Notes*; Schrodinger Press: Portland, 2003) were performed based on the crystal structure of PIM-1 kinase in complex with AMP-PNP as a template (Qian et al., *J. Biol. Chem.* 280, 6130-6137, 2005; Jacobs et al., *J. Biol. Chem.* 280, 13728, 2005; Kumar et al., *J. Mol. Biol.* 348, 183, 2005; Bullock et al., *J. Med. Chem.* 48, 7604-7614, 2005; Ryan et al., PCT Publication WO 2004/024895; Jeremy et al., PCT Publication WO 2004/058769). The computational screening of ~1.5 million focused and or diverse drug like compounds from libraries of Life Chemicals, Maybridge, TimTec, BioFocus ComGenex and Ambinter led to the selection of 63 candidate compounds exclusively from BioFocus library (BioFocus, 2464, Massachusetts Avenue, Cambridge, Mass. 02140, USA, www.biofocus.com). Nine compounds were found to be active in the low-micromolar range (8-10 μM) and 2 of them were found to exhibit <8 μM activity in direct PIM-1 kinase binding assay. The most active compounds for the identification of molecular regions important for specific Pim-1 kinase activity belong to the class of both imidazo[1,2-b]pyridazines (Beswick et al., PCT Publication WO1996/9631509; Raboisson et al., *Tetrahedron* 59, 5869-5878, 2003) and pyrazolo[1,5-a]pyrimidine (Williamson et al., *Bioorganic & Med. Chem. Letters* 15, 863-867, 2005). As described below, the compounds selected from virtual screening were filtered based on binding mode, QikProp (Schrodinger. L. L. C., New York (http://www.schrodinger.com); Schrodinger LLC. *QikProp Technical Notes*; Schrodinger Press: Portland, 2003.) (solubility, permeability) Lipinski-like criteria (CA Lipinski, *Adv. Drug Del. Rev.* 23, 3, 1997). and the presence of desired pharmacophore groups. These classes of compounds served as template structures for lead optimization, synthesis and PIM-1 kinase screening.

1. Preprocessing of Three-Dimensional Ligand Database

The external source database in the form of sdf format files from Life Chemicals (16173), Maybridge (Hitfinder and screening collection; 16000, 58855) TimTec (Actimol Collection; 82000), BioFocus (45842), ComGenex (4573) and Ambinter (5534), and their three-dimensional coordinates in mae format, was generated for each of sdf files using the LigPrep module within the Schrodinger software package. The final coordinates were stored in a multi mae file. LigPrep uses special caution regarding the protonation state of ionizable groups (e.g., amines, amidines, carboylic acids) of all the ligands selected are assumed to be ionized at a physiological pH of 7.4. Separate multi mae format files suitable for Qik-Prop and Glide virtual screen were generated. Each of the databases together with a final library of 1,54122 molecules were considered for virtual screening.

2. Preparation of Protein Coordinates and Definition of Active Sites

Reference protein coordinates used for Glide virtual screening were taken from the X-ray structure of PIM-1 kinase in complex with AMP-PNP (pdb entry: 1XR1). Water molecules were then removed and the missing bond order and geometries were edited. Hydrogen atoms were added and the combined complex structure was submitted for protein preparation calculation. The fully refined structure with bound AMP-PNP molecule was further submitted for Grid calculation to define the active site as the collection of amino acids enclosed within a 12 Å radius sphere centered on the bound ligand.

3. Virtual Screening of the QikProp filtered libraries using Glide

Typically each multi mae file molecules were submitted for QikProp calculations. The Tanimoto coefficient, as criteria for selection of similar compounds within the databases was implemented and this has led to the selection of final molecules of 9267, 26593, 16394, 29394, 13258 and 3964 from each database for virtual screening.

4. Postprocessing and Compound Selection Criteria

Compounds having desired Glide scores, hydrogen bond formation and hydrophobic interactions were estimated by interatomic distances for further analysis. The conformational stability of each candidate was also estimated by force field energy difference between the complexed conformation and freely minimized conformation, and the top-scoring candidates from this category were selected for further analysis. Compounds in each of the three categories were visually inspected to eliminate candidates without ideal hydrogen bond geometry, hydrophobic molecular surfaces, or torsion angles. The resulting 236 structures were further analyzed using QikPro to calculate log S, permeability, MW and Lipinski like criteria. This further reduced the number of compounds to 69. These candidates were pooled, and redundant entries with the same chemical structure were represented by a single entry. Six imidazo[1,2-b]pyridazine derivatives and 13 pyrazolo[1,5-a]pyrimidine derivatives were selected and evaluated for their ability to inhibit PIM-1 kinase activity in an in-vitro assay.

5. Results

Imidazo[1,2-b]pyridazines and pyrazolo[1,5-a]pyrimidines of the BioFocus library are summarized in Table I and Table III. The binding mode of these scaffolds from the docking predictions revealed that the imidazo[1,2-b]pyridazine moiety positioned similar to that of adenine and interacts with the hinge region residues Glu121, Arg122 and Pro123. The aromatic groups at the $R_1$ position with various substitutions at $3^{rd}$ position seems more favorable and exhibit more stable conformation with in the PIM-1 kinase pocket. The C-8 substitutions are more favorable than C-6 substitutions. Computational data for these two scaffolds suggested that R1 and R2 substitutions exhibit strong binding energy when compared to pyrazolo[1,5-a]pyrimidine. Based on these analyses, we have optimized the compounds identified in the BioFocus library and developed new compounds set forth in Tables II and IV.

TABLE I

Illustrative Imidazo[1,2-b]Pyridazine PIM-1 Kinase Inhibitors

| Compound No. | Structure |
|---|---|
| 1-1 | (structure) |

TABLE I-continued
Illustrative Imidazo[1,2-b]Pyridazine PIM-1 Kinase Inhibitors
| Compound No. | Structure |
|---|---|
| 1-2 | 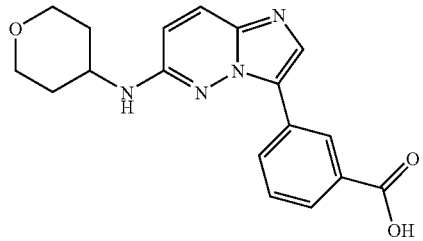 |
| 1-3 | 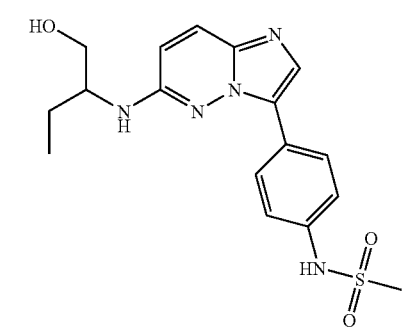 |
| 1-4 | 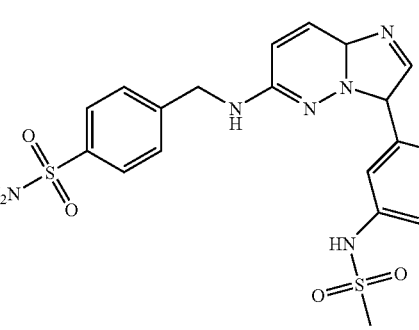 |
| 1-5 | 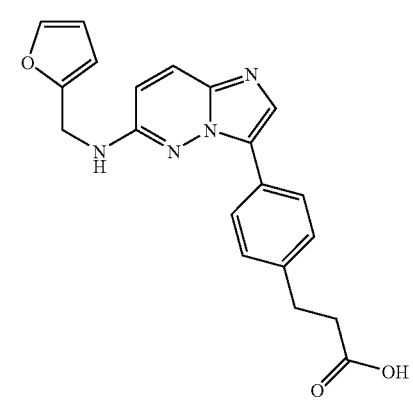 |
| 1-6 | 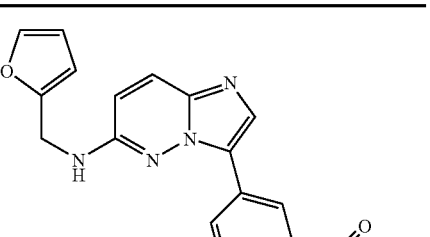 |
TABLE II
Illustrative Imidazo[1,2-b]Pyridazine Pim-1 Kinase Inhibitors.
| Compound No. | Structure |
|---|---|
| 2-1 | 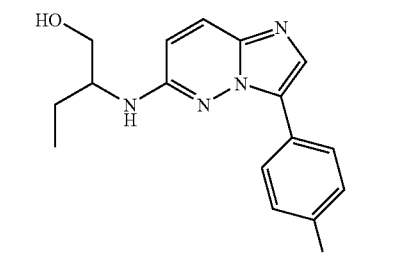 |
| 2-2 | 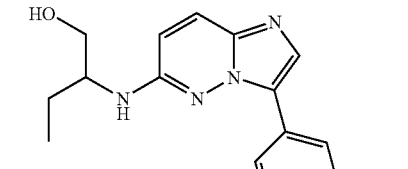 |
| 2-3 | 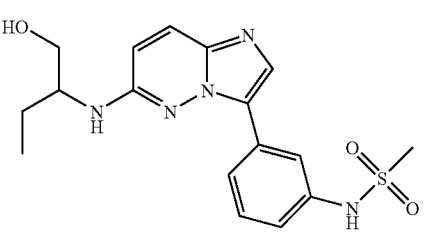 |

TABLE II-continued
Illustrative Imidazo[1,2-b]Pyridazine Pim-1 Kinase Inhibitors.
| Compound No. | Structure |
|---|---|
| 2-4 | 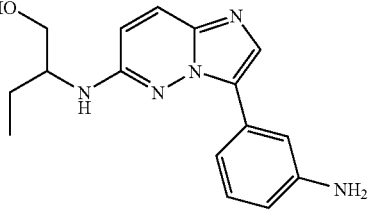 |
| 2-5 | 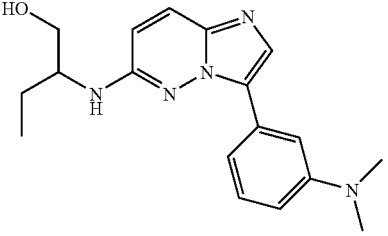 |
| 2-6 | 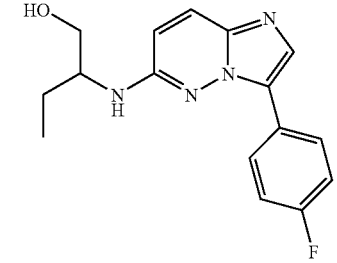 |
| 2-7 | 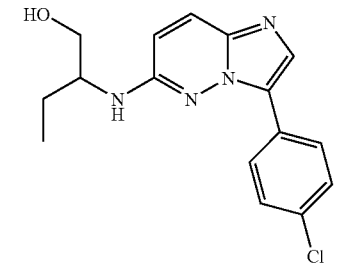 |
| 2-8 | 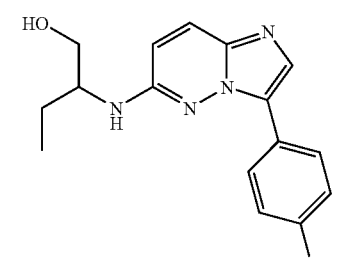 |
| 2-9 | 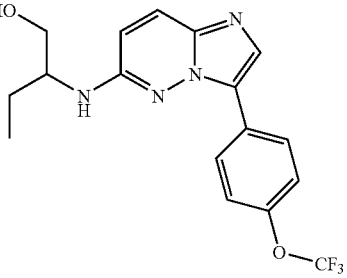 |
| 2-10 | 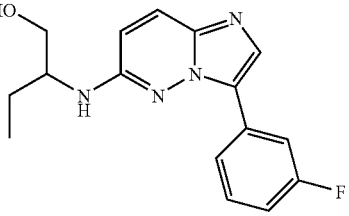 |
| 2-11 | 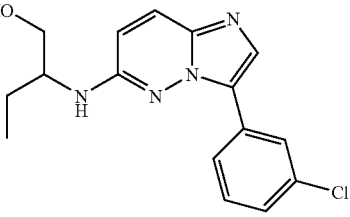 |
| 2-12 | 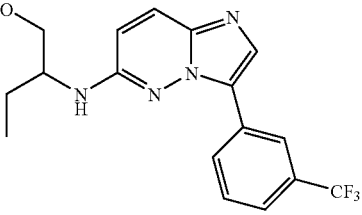 |
| 2-13 | 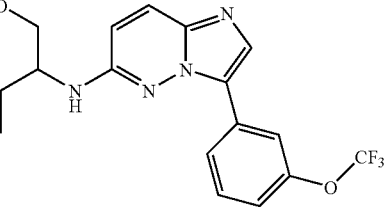 |
| 2-14 | 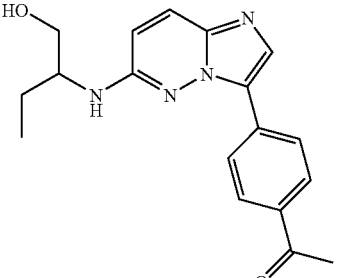 |

TABLE II-continued

Illustrative Imidazo[1,2-b]Pyridazine Pim-1 Kinase Inhibitors.

| Compound No. | Structure |
|---|---|
| 2-15 | 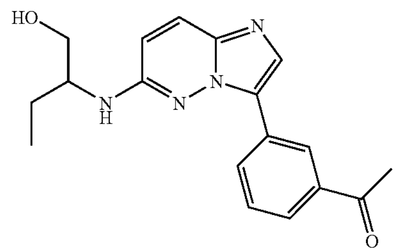 |
| 2-16 | 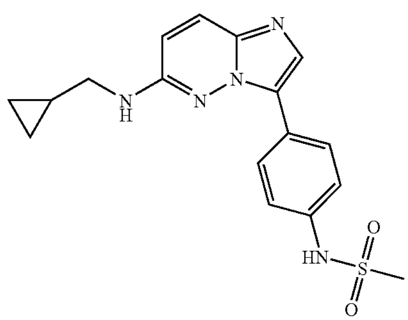 |
| 2-17 | 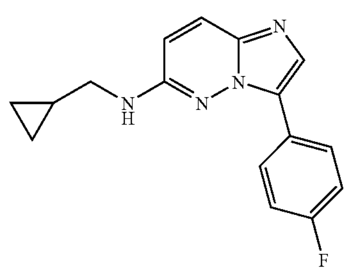 |
| 2-18 | 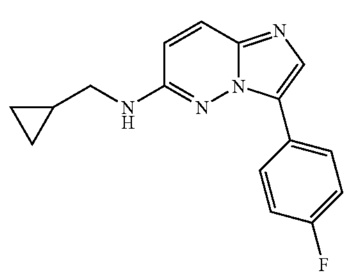 |
| 2-19 | 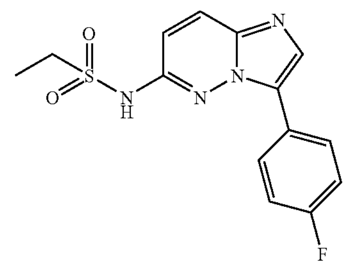 |
| 2-20 | 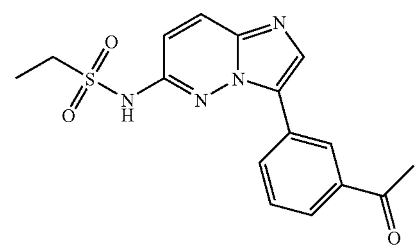 |
| 2-21 | 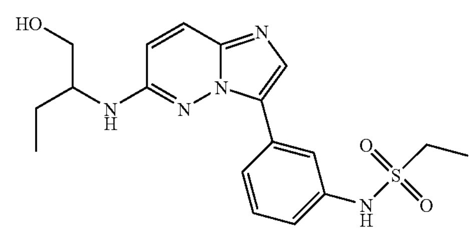 |
| 2-22 | 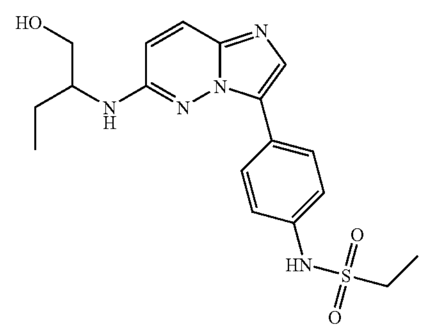 |

TABLE III

Illustrative Pyrazolo[1,5-a]Pyrimidine PIM-1 Kinase Inhibitors

| Compound No. | Structure |
|---|---|
| 3-1 | 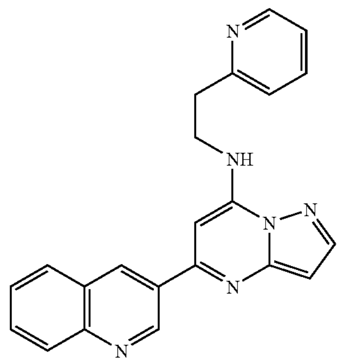 |
| 3-2 | 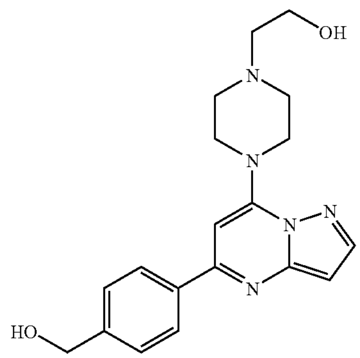 |
| 3-3 | 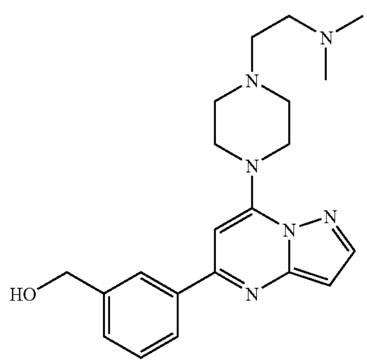 |
| 3-4 | 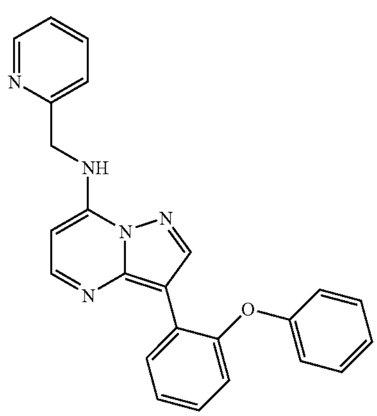 |

TABLE III-continued

Illustrative Pyrazolo[1,5-a]Pyrimidine PIM-1 Kinase Inhibitors

| Compound No. | Structure |
|---|---|
| 3-5 | 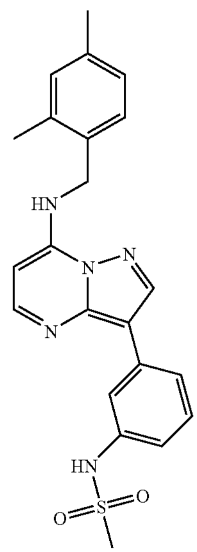 |
| 3-6 | 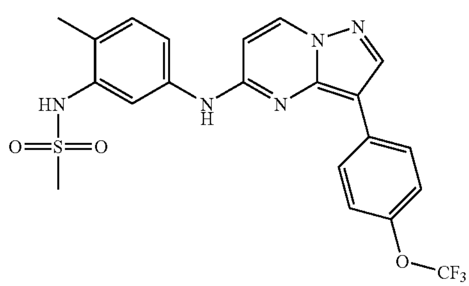 |
| 3-7 | 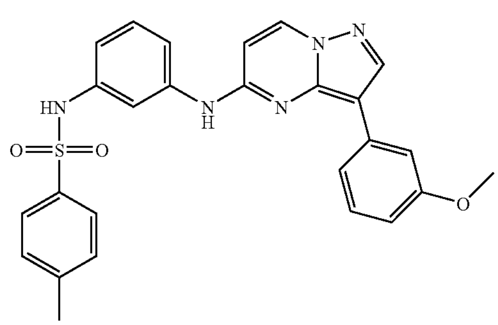 |
| 3-8 | 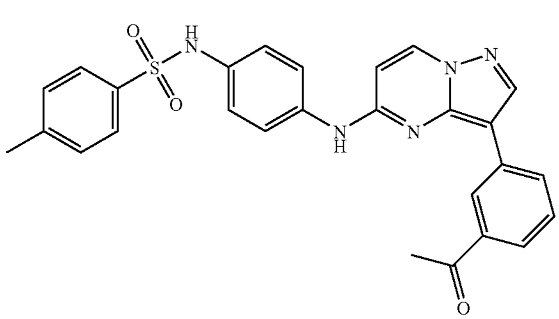 |

TABLE III-continued
Illustrative Pyrazolo[1,5-a]Pyrimidine PIM-1 Kinase Inhibitors
| Compound No. | Structure |
|---|---|
| 3-9 | 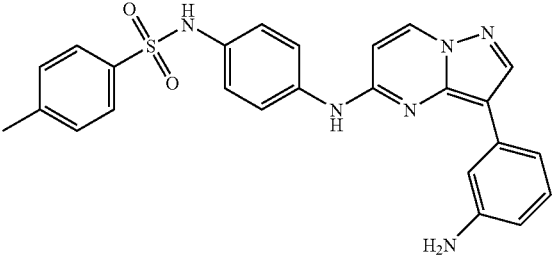 |
| 3-10 | 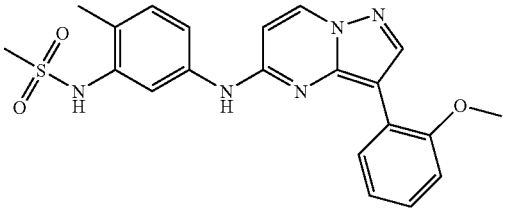 |
| 3-11 | 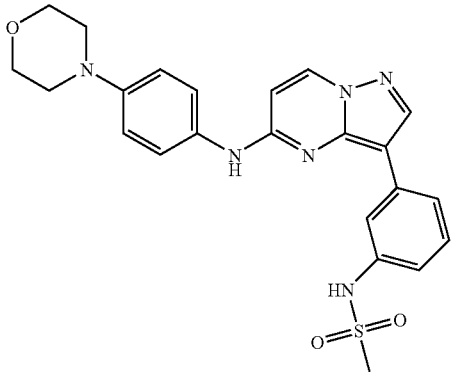 |
| 3-12 | 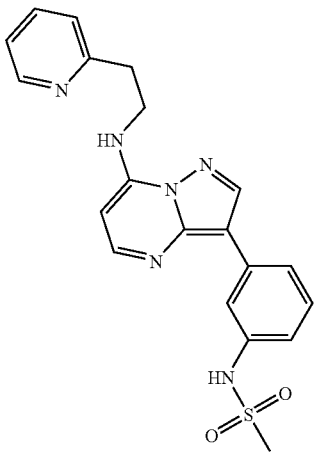 |

TABLE III-continued
Illustrative Pyrazolo[1,5-a]Pyrimidine PIM-1 Kinase Inhibitors
| Compound No. | Structure |
|---|---|
| 3-13 | 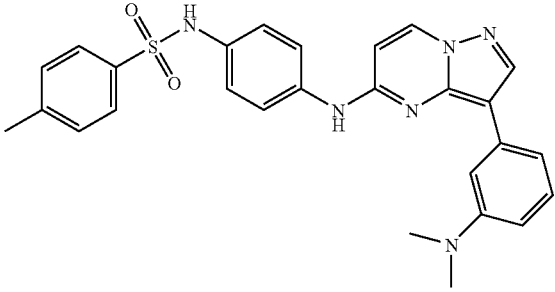 |
TABLE IV
Illustrative Pyrazolo[1,5-a]Pyrimidine Pim-1 Kinase Inhibitors
| Compound No. | Structure |
|---|---|
| 4-1 | 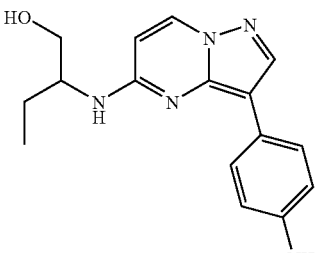 |
| 4-2 | 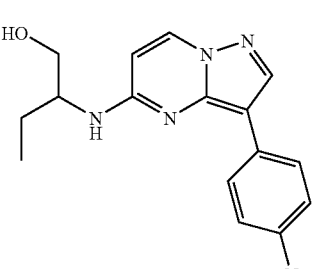 |
| 4-3 | 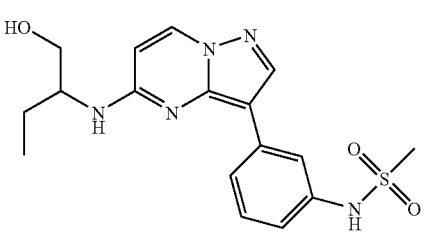 |
| 4-4 | 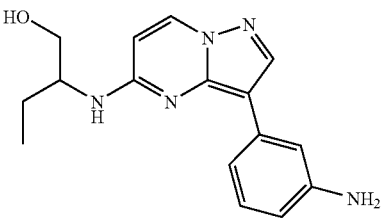 |
TABLE IV-continued
Illustrative Pyrazolo[1,5-a]Pyrimidine Pim-1 Kinase Inhibitors
| Compound No. | Structure |
|---|---|
| 4-5 | 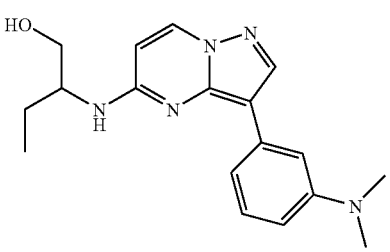 |
| 4-6 | 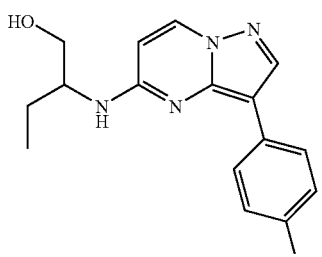 |
| 4-7 | 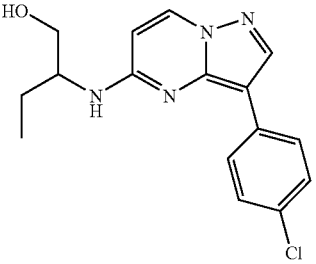 |

TABLE IV-continued

Illustrative Pyrazolo[1,5-a]Pyrimidine Pim-1 Kinase Inhibitors

| Compound No. | Structure |
|---|---|
| 4-8 | (structure) |
| 4-9 | (structure) |
| 4-10 | (structure) |
| 4-11 | (structure) |
| 4-12 | (structure) |
| 4-13 | (structure) |
| 4-14 | (structure) |
| 4-15 | (structure) |
| 4-16 | (structure) |
| 4-17 | (structure) |
| 4-18 | (structure) |

TABLE IV-continued

Illustrative Pyrazolo[1,5-a]Pyrimidine Pim-1 Kinase Inhibitors

| Compound No. | Structure |
|---|---|
| 4-19 | 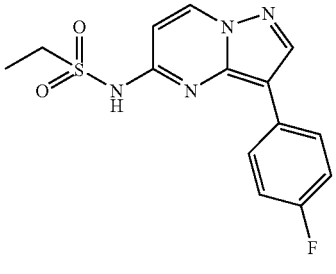 |
| 4-20 | 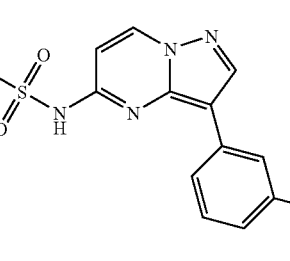 |
| 4-21 | 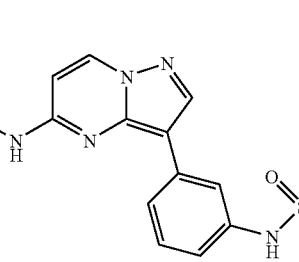 |
| 4-22 | 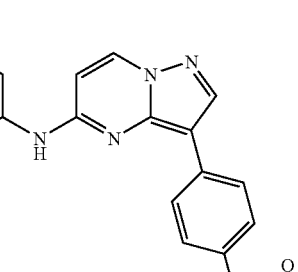 |

Example 2

Synthesis of Imidazo[1,2-B]pyridazine Compounds

Certain illustrative compounds of the invention were made as set forth in the following reaction schemes and detailed synthetic examples.

Scheme 1

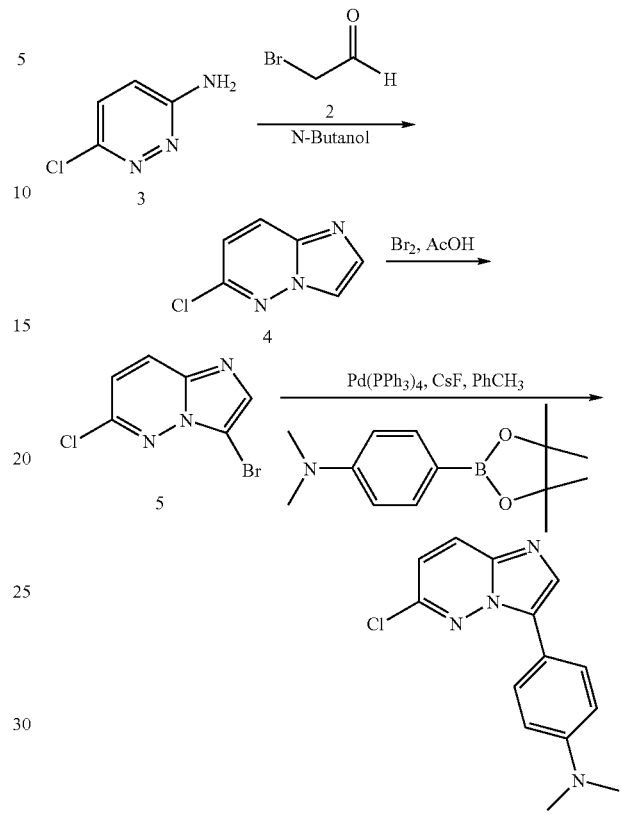

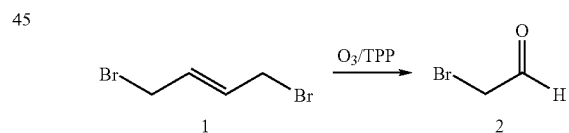

1. Preparation of Bromo acetaldehyde (2)

1,4-dibromo-trans-2-butene (1) (10 g, 0.046 mol) was dissolved in dry $CH_2Cl_2$ (100 ml) and cooled to −78° C. and ozone gas was bubbled until the blue color persisted (~30 min). A nitrogen stream was passed through the solution until the blue color disappeared, giving colorless solution. Triphenyl phosphine (12.9 g, 0.046 mol) was added portion wise over a period of 1 hr. The reaction mixture was brought to 0° C. and kept in the refrigerator for 15 hrs. The solvent ($CH_2Cl_2$) was removed from the reaction mixture (without applying vacuum) and the thick residue was distilled at 40° C. under vacuum (1 mm Hg), maintaining the temperature of the receiving flask at −78° C. (during distillation, special care was taken to maintain a cold water circulation (~0° C. to −5° C.)). The bromo acetaldehyde (2) (2.8 g, yield=50%) was obtained as a light yellow liquid, which was highly lachrymatory.

2. 6-Chloro-imidazo[1,2-b]pyridazine (4)

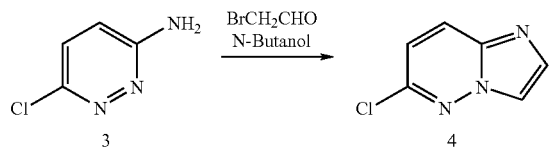

3-Amino-6-chloro pyridazine (1.5 g, 0.0116 mol) was dissolved in n-butanol (12 ml), cooled to 0° C. and bromoacetaldehyde (2.8 g, 0.023 mol) was added. The reaction was refluxed for 20 hrs and n-butanol was removed under reduced pressure. To the reaction mixture, water was added and extracted with EtOAc (5×20 ml). The combined organic layers were dried ($Na_2SO_4$), concentrated under reduced pressure and the residue was purified by column chromatography (EtOAc/hexane) to give 6-Chloro-imidazo[1,2-b]pyridazine (4) (690 mg, yield=40%).

3. 3-Bromo-6-chloro-imidazo[1,2-b]pyridazine (5)

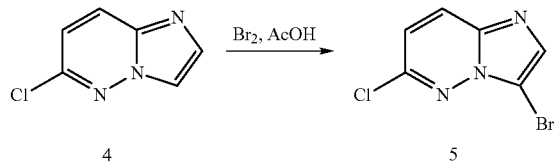

The 6-Chloro-imidazo[1,2-b]pyridazine (4) (500 mg, 0.0032 mol) was taken in glacial acetic acid (5 ml) and bromine (0.4 ml) was added slowly at room temperature. After 20 minutes, solid precipitated out and was filtered. The solid was washed with ether (3×15 ml) and dried under air to give 3-Bromo-6-chloro-imidazo[1,2-b]pyridazine (5) (400 mg, yield=60%).

4. 4-(6-chloro-imidazo[1,2-b]pyridazine-3-yl)-phenyl]-dimethylamine (6)

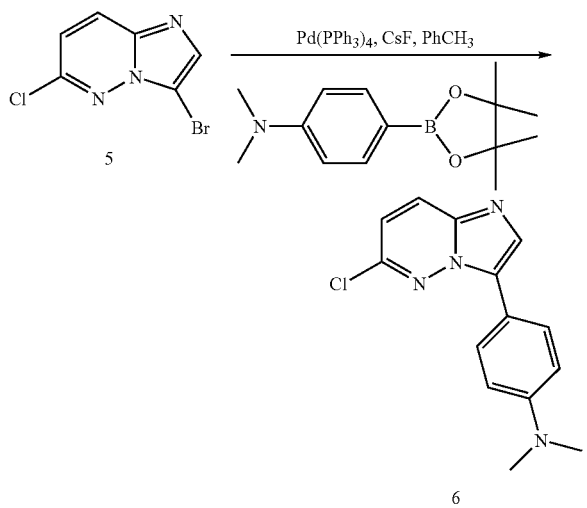

In a two necked round bottomed flask $Pd(PPh_3)_4$ (0.07 g, 0.068 mmol) and CsF (0.31 g, 0.0020 mol) was taken in anhydrous $PhCH_3$ (1.6 ml). Argon was bubbled through the reaction mixture for 10 minutes and then 3-Bromo-6-chloro-imidazo[1,2-b]pyridazine (5) followed by Boronic acid was added. The reaction mixture was refluxed for 20 hours. Solvent was removed from the reaction mixture under reduced pressure. The residue was taken in EtOAc (20 ml) and filtered through celite. The filtrate was concentrated under reduced pressure to obtain the residue which was purified by column chromatography (MeOH/$CH_2Cl_2$) to furnish [4-(6-chloro-imidazo[1,2-b]pyridazine-3-yl)-phenyl]-dimethylamine (6) (50 mg, yield=30%).

5. 2-[3-(4-Dimethylaminophenyl)-imidazo[1,2-b]pyridazine-6-yl(±)-2-amino]butan-1-ol (7)

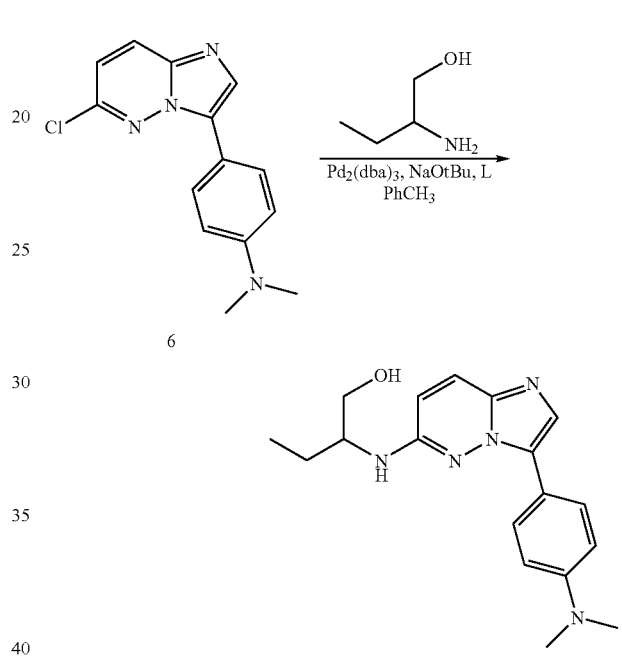

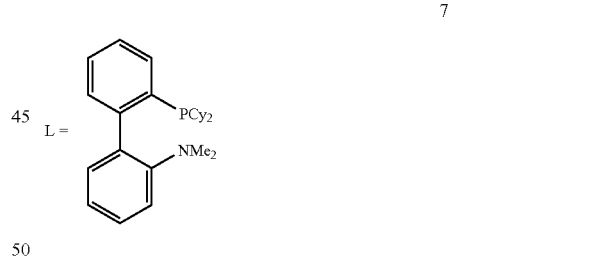

In a two necked round-bottomed flask, $Pd_2(dba)_3$ (0.001 g, 0.0009 mmol), sodium tert-butoxide (0.02 g, 0.256 mmol) and ligand (0.001 g, 0.0027 mmol) was taken in anhydrous $PhCH_3$. Argon was passed through the reaction mixture for 10 minutes and then [4-(6-chloro-imidazo[1,2-b]pyridazine-3-yl)-phenyl]-dimethylamine (6) (0.05 g, 0.18 mmol) and (±)-2-amino-1-butanol (0.02 g, 0.22 mmol) was added. The reaction was refluxed for 24 hrs. Toluene was removed from the reaction mixture under reduced pressure, and the residue was taken in EtOAc (25 ml), filtered through celite. The filtrate was concentrated under reduced pressure and the residue was purified by column chromatography (MeOH/$CH_2Cl_2$) to give 2-[3-(4-Dimethylaminophenyl)-imidazo[1,2-b]pyridazine-6-yl(±)-2-amino]butan-1-ol (7) (15 mg, yield=31%, HPLC purity=97%).

6. General Scheme and Procedures for the Synthesis of Compounds 9 and 10

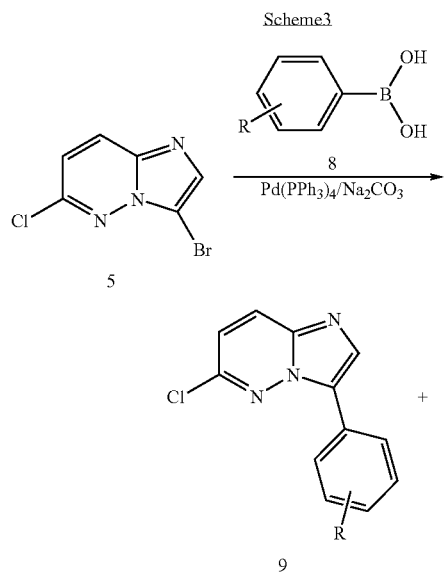

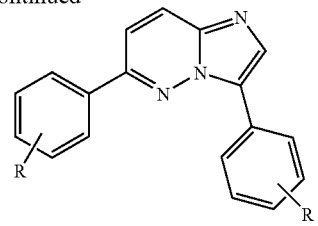

R = —N(CH$_3$)$_2$, 3-F, 4-F, 3-CF$_3$, 4-CF$_3$
3-OCF$_3$, 4-OCF$_3$, 3-NHSO$_2$CH$_3$
4-NHSO$_2$CH$_3$, 3-NO$_2$, 3-NO$_2$, 4-NO$_2$,
3-OCH$_3$, 4-OCH$_3$, 3-Cl 4-Cl

In a two necked round bottomed flask Pd(PPh$_3$)$_4$ (0.068 mmol) and CsF (0.0020 mol) was taken in anhydrous PhCH$_3$ (1.6 ml). Argon was bubbled through the reaction mixture for 10 minutes and then 3-Bromo-6-chloro-imidazo[1,2-b]pyridazine (5) followed by 3 or 4-substituted boronic acids was added. The reaction mixture was refluxed for 20 hours. Solvent was removed from the reaction mixture under reduced pressure. The residue was taken in EtOAc (20 ml) and filtered through celite. The filtrate was concentrated under reduced pressure to obtain the residue which was purified by column chromatography (MeOH/CH$_2$Cl$_2$) to yield 6:4 ratio [3 or 4-(substituted)-(6-chloro-imidazo[1,2-b]pyridazine-3-yl)-phenyl]-dimethylamine 9 and 10.

7. Scheme for the synthesis of 2-(3-(3-(trifluoromethoxy)phenyl)imidazo[1,2-b]pyridazin-6-yl(±)-2-amino)-butan-1-ol (Compound 7-17)

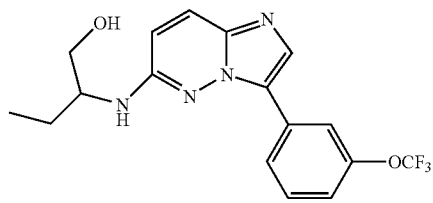

7-17 a. Synthesis of 6-chloro-3-(3-(trifluoromethoxy)phenyl)imidazo[1,2-b]pyridazine
(Compounds 7-12, 7-13))

To a degased MeOH/Toluene (1:4, 5 mL) solvent and 2M of $Na_2CO_3$ (0.215 mL, 0.430 mmol) under Argon was added 3-bromo-6-chloroimidazo[1,2-b]pyridazine (100 mg, 0.430 mmol), 3-fluoromethoxyphenyl boronic acid (98 mg, 0.430 mmol) and $Pd(PPh_3)_4$ (8.95 mg, 7.74 uM, 0.018 eq). The resulting reaction mixture was heated to reflux overnight (12 h). TLC (5% MeoH/DCM, Rf=0.2) showed the presence of starting material 3-bromo-6-chloroimidazo[1,2-b]pyridazine and an additional two new spots with strong fluoresense. The reaction mixture was concentration and the crude product was purified by CombiFlash Companion using 0% 70% EtOAc/Hexane 40 min, (4 g normal phase RediSep Flash column with flow 18 mL/min) solvent system provided the separation of two products as afforded the Compound 7-12 63 mg (46.7%), and Compound 7-13 13 mg (6.88%).

b. Synthesis of 2-(3-(3-(trifluoromethoxy)phenyl)imidazo[1,2-b]pyridazin-6-ylamino)-butan-1-ol
(Compound 7-17)

To the toluene solvent was added 7-12 (30 mg), 2-amino-1-butanol (18.08 uM, 2 eq), ligand (5.65 mg, 0.15 eq), $Pd_2(dba)_3$ (6.57, 0.05 eq) and NaOtBu (13.05 mg, 1.42 eq). The resulting reaction mixture was degassed for 10 min under argon and then was heated to reflux overnight (12 h). The crude product was concentration and preparative TLC was performed with 10% MeOH/DCM solvent system afforded 10 mg of racemic 7-17 (28.5%).

9. Scheme for the synthesis of Compounds 7-27 and 7-28

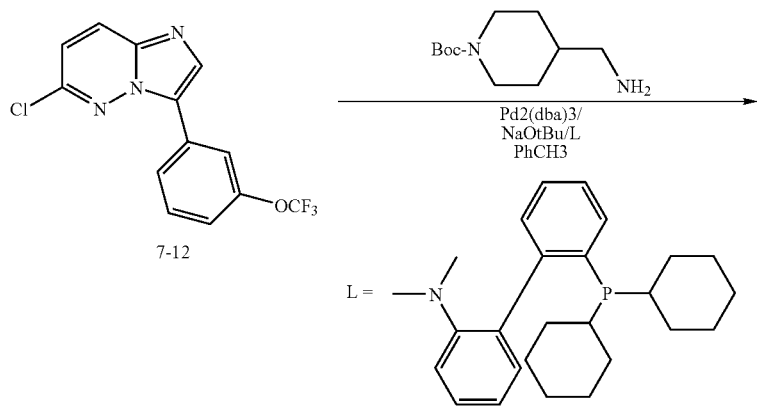

Scheme 5

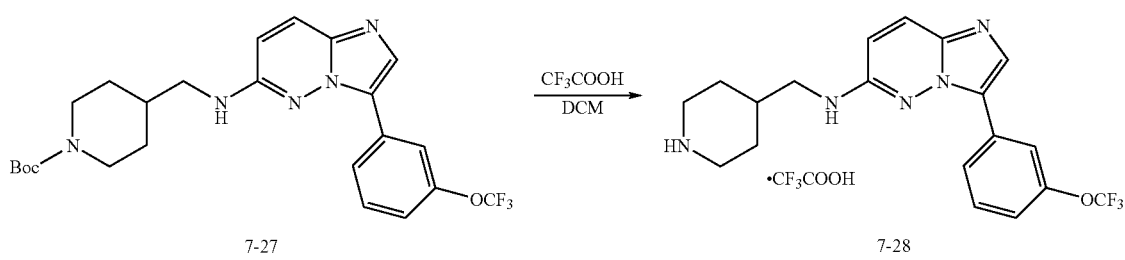

10. Synthesis of tert-butyl 4-((3-(3-(trifluoromethoxy)phenyl)imidazo[1,2-b]pyridazin-6-ylamino)methyl)piperidine-1-carboxylate (Compound 7-27)

To the toluene solvent was added 7-12 (100 mg, 0.319 mmol), 4-Aminomethyl-1-Boc-piperidine (68.3 mg, 0.319 mmol), ligand (18.8 mg, 0.048 mmol), $Pd_2(dba)_3$ (0.05 eq) and NaOtBu (1.5 eq). The resulting reaction mixture was degassed for 10 min under argon and then was heated to reflux overnight (12 h). The crude product was concentration and preparative TLC was performed with 10% MeOH/DCM solvent system afforded 84 mg of 7-27 (53.6%).

11. Synthesis of N-(piperidin-4-ylmethyl)-3-(3-(trifluoromethoxy)phenyl)imidazo[1,2-b]pyridazin-6-amine 2,2,2-trifluoroacetate (Compound 7-28)

1 mL of DCM and 1 mL of TFA (0.098 mmol) was added sequentially to 7-27 (48 mg, 0.0). The reaction completed in 1 h at rt. TLC (20% MeOH/DCM) Rf=0.1. The concentration to remove TFA completely provided the crude 7-28 TFA salt. Preparative TLC (20% MeOH/DCM) gave 48 mg (97%) of colorless solid.

12. Scheme for the Synthesis of 7-29

13. Synthesis of N-((1-methylpiperidin-4-yl)methyl)-3-(3-(trifluoromethoxy)phenyl imidazo[1,2-b]pyridazin-6-amine (Compound 7-29)

To the toluene (5 mL) solvent was added 7-12 (40 mg, 0.128 mmol), (1-methylpiperidin-4-yl)methanamine (24.53 0.191 mmol), ligand (7.53 mg, 0.019 mmol), $Pd_2(dba)_3$ (8.76, 9.56 mmol) and NaOtBu (17.40 mg, 0.181 mmol). The resulting reaction mixture was degassed for 10 min under argon and then was heated to reflux overnight (12 h). The crude product was concentration and preparative TLC was performed with 10% MeOH/DCM solvent system afforded 17.6 mg of 7-23 (50%).

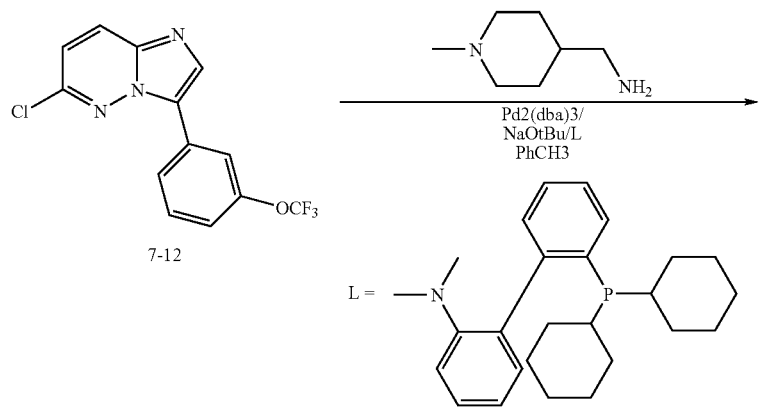

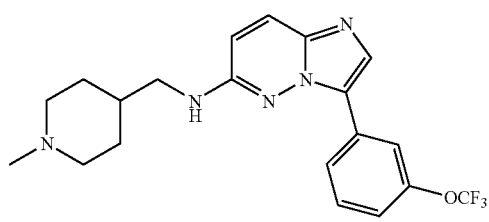

14. Scheme for the synthesis of Compound 7-31

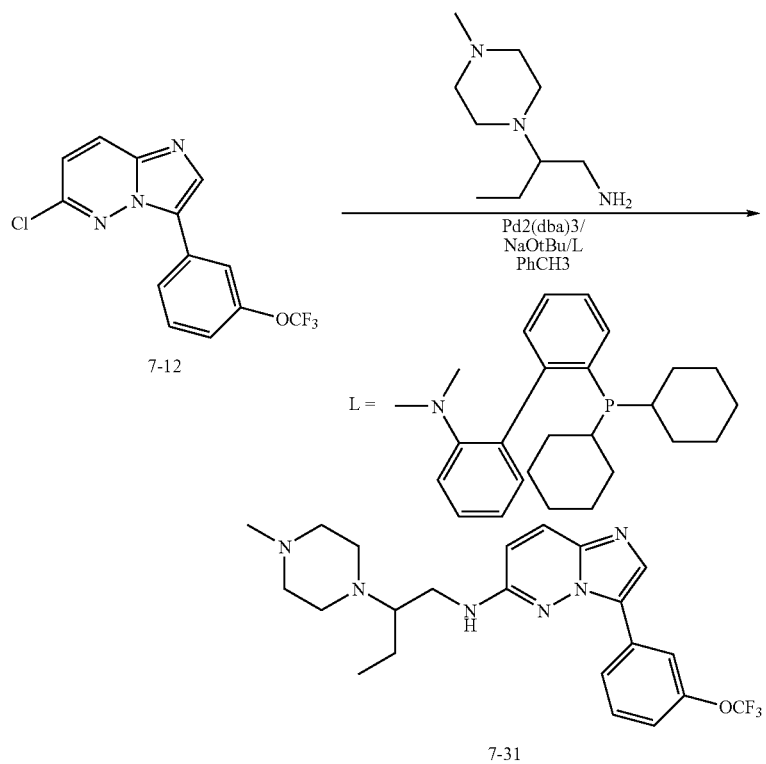

15. ±N-(2-(4-methylpiperazin-1-yl)butyl)-3-(3-(trifluoromethoxy)phenyl)imidazo[1,2-b]pyridazin-6-amine (Compound 7-31)

To the toluene (5 mL) solvent was added 7-12 (40 mg, 0.128 mmol), (O)$_2$-(4-methylpiperazin-1-yl)butan-1-amine (0.191 mmol), ligand (0.019 mmol), Pd$_2$(dba)$_3$ (9.56 mmol) and NaOtBu (0.181 mmol). The resulting reaction mixture was degassed for 10 min under argon and then was heated to reflux overnight (12 h). The crude product was concentration and preparative TLC was performed with 10% MeOH/DCM solvent system afforded 22 mg of 7-31.

Example 3

Pim-1 Kinase Activity Assays

A. Pim-1 Kinase Inhibition Assay

One illustrative manner in which Pim-1 kinase activity can be determined is by quantifying the amount of ATP remaining in solution after an in vitro Pim-1 kinase reaction. The Kinase-Glo Assay Kit (Promega, Inc., Madison, Wis.) allows this. The amount of ATP remaining in the solution after the kinase reaction serves as a substrate for the luciferase to catalyze luciferin to oxyluciferin plus one photon of light. Thus, the luminescent signal read by the Luminoskan Ascent Instrument (Thermo Electron Corp., Milford, Mass.) correlates with the amount of ATP present after the kinase reaction and inversely correlates with the amount of kinase activity. This assay is efficient at determining the IC$_{50}$ values of kinase inhibitors against the Pim-1 kinase. These assays are set up in duplicate 50 ul volumes in white, flat bottom 96 well plates. Inhibitors are added to the solution of 1× kinase buffer, 10 uM ATP, 100 uM Pim-1-specific substrate, 50 ng of active Pim-1 enzyme, and water in serial dilutions ranging from micromolar to nanomolar concentrations. This solution is incubated at 30 degrees Celsius at 360 rpm for two hours. Following the incubation, 50 ul of Kinase-Glo reagent is added to each well, including all positive and negative control wells, and incubated at room temperature for 15 minutes. The plate is then read by the Luminoskan Ascent instrument and the results displayed with the Ascent Software version 2.6. The IC$_{50}$ values can then be calculated for each inhibitor tested.

Alternatively, Pim-1 kinase activity can be determined by quantifying the phosphorylation of a known Pim-1 substrate in another in vitro assay. The Z-Lyte Protein Kinase Assay Kit (Invitrogen, Madison Wis.) allows this, using Fluorescent Resonance Energy Transfer (FRET) procedure. Briefly, a known Pim-1 substrate (Serine-Threonine Substrate 7 from Invitrogen), which bears two fluorophores at opposing ends (coumarin and fluorescein) is incubated with Pim-1 enzyme and a potential inhibitor. Following this, the kinase reaction is stopped, and a development reagent is added. This reagent, a protease, will cleave only unphosphorylated substrate, separating the two fluorophores and reducing the amount of FRET which can occur between them. FRET can then be measured using a spectrophotometer, such as the Gemini EM (Molecular Devices). A reduction in FRET is indicative of an active inhibitor.

B. Cell-Based Pim-1 Kinase Inhibitor Assays:

Cell culture-based assays can be used to evaluate the ability of compounds of the invention to inhibit one or more cellular activities, such as cancer cell growth and/or survival. Numerous cancer cell lines can be obtained from the American Type Culture Collection (ATCC) and other sources. Briefly, cells are seeded into 96-well, tissue-culture treated, opaque white plates (Thermo Electron, Vantaa, Finland), at between 5000 and 10000 cells per well, depending on the speed of cell proliferation, in 100 µl of appropriate growth medium (determined by the ATCC). Cells are then exposed to the appropriate concentration of drug or an equal amount of DMSO (drug diluent) and allowed to grow in its presence for 96 hours. Following this, 100 µl of Cell-Titer-Glo reagent (Promega, Inc., Madison, Wis.) is added to each well. Plates are then shaken for 2 minutes at room temperature to allow for cell lysis and incubated for 10 minutes at room temperature to stabilize the luminescent signal. Similar to the Kinase-Glo assay reagent from Promega, this reagent contains both luciferase enzyme and its substrate luciferin. Luciferase, activated by ATP in the cell lysate, catalyzes the conversion of luciferin to oxyluciferin, a reaction which produces light. The amount of light produced is proportionate to the amount of ATP in the cell lysate, which is itself proportional to cell number and gives an index of cellular proliferation.

In order to detect specific inhibition of Pim-1 enzyme in cell culture, a Western blot assay will also be performed. For this, cells which have been treated with a potential Pim-1 inhibitor are lysed with a buffer specific for the isolation and preservation of proteins (1% Nonidet P-40, 150 mM NaCl, 50 mM Tris pH 8.0, 5 mM EDTA, 1:500 Protease Inhibitor Cocktail III [Calbiochem], 100 mM NaF, 100 mM Sodium Orthovanadate). The protein concentration in these lysates is then quantified using the BCA Protein Assay Kit (Pierce). Known amounts of protein, e.g. 10 µg, are loaded onto 12% SDS-polyacrylamide gels and are subjected to reducing, denaturing SDS-PAGE. Electrophoresed proteins are transferred to a nitrocellulose membrane, which is then probed with antibodies to p-21 and phospho (Thr 145) p-21. As Threonine-145 of the p-21 protein is a substrate for Pim-1, measuring the amount of phosphorylation at this site in treated cells should provide a means by which to evaluate the efficacy of our Pim-1 inhibitors.

C. Pim-1 Kinase Specific Activity Data:

Using procedures essentially as described above, illustrative compounds were tested for inhibition of Pim-1 kinase activity. FIG. 1 shows the results for illustrative compounds screened at 10 µM using the Z-LYTE assay. Values are given as a percent of untreated controls. As shown in FIG. 1, the compounds were effective for inhibiting Pim-1 kinase activity by this assay.

In addition, $IC_{50}$ values were determined for illustrative compounds against Pim-1 kinase, using the Promega Kinase-Glo assay, the results for which are summarized in Table V below. Further still, illustrative compounds were evaluated for cell-based activity in cells expressing Pim-1. $IC_{50}$ values, representing the concentrations required to inhibit cell growth to 50% of untreated, are provide in µM in Table VI below. Thus, by multiple assays, the compounds represent active inhibitors of Pim-1 kinase and are capable of inhibiting cell growth.

TABLE V

Kinase inhibitory activity of novel compounds.

| Compound No. | $IC_{50}$ µM) |
|---|---|
| 1-1 | 4.47 |
| 1-3 | 5.35 |
| 3-13 | 52.07 |
| 7-1 | 3.99 |
| MP-392 | ND |

TABLE VI

Cell-based activity of illustrative compounds.

| Compound No. | K562 Cells | PC-3 Cells |
|---|---|---|
| 1-1 | >300 | >300 |
| 1-3 | 80.2 | 39.0 |
| 3-9 | 20.6 | 12.0 |
| 3-13 | 29.3 | 12.78 |
| 7-1 | 67.1 | 29.22 |

Example 4

Synthesis of imidazo[1,2-B]pyridazine Compounds

Other compounds of the invention, including illustrative compounds set forth in Table VII, were made according to the following synthetic examples.

1. Preparation of Bromo acetaldehyde (2)

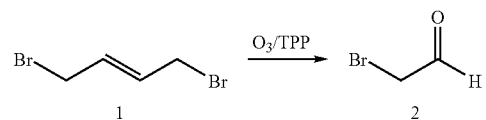

1,4-dibromo-trans-2-butene (1) (10 g, 0.046 mol) was dissolved in dry $CH_2Cl_2$ (100 ml) and cooled to −78° C. and ozone gas was bubbled till the blue color persisted (~30 mins). A nitrogen stream was passed through the solution until the blue color disappeared giving colorless solution. Triphenyl phosphine (12.9 g, 0.046 mol) was added portion wise over a period of 1 hr. The reaction mixture was brought to 0° C. and kept in the refrigerator for 15 hrs. The solvent ($CH_2Cl_2$) was removed from the reaction mixture (without applying vacuum) and the thick residue was distilled at 40° C. under vacuum (1 mm Hg) maintaining the temperature of the receiving flask at −78° C. [Note: During the distillation, special care was taken to maintain a cold water circulation (~0° C. to −5° C.)]. The bromo acetaldehyde (2) (2.8 g, yield=50%) was obtained as a light yellow liquid, which was highly lachrymatory.

2. 6-Chloro-imidazo[1,2-b]pyridazine (4)

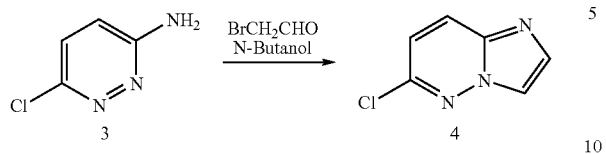

3-Amino-6-chloro pyridazine (1.5 g, 0.0116 mol) was dissolved in n-butanol (12 ml), cooled to 0° C. and bromoacetaldehyde (2.8 g, 0.023 mol) was added. The reaction was refluxed for 20 hrs and n-butanol was removed under reduced pressure. To the reaction mixture, water was added and extracted with EtOAc (5×20 ml). The combined organic layers were dried (Na$_2$SO$_4$), concentrated under reduced pressure and the residue was purified by column chromatography (EtOAc/hexane) to afford 6-Chloro-imidazo[1,2-b]pyridazine (4) (690 mg, yield=40%).

3. 3-Bromo-6-chloro-imidazo[1,2-b]pyridazine (5)

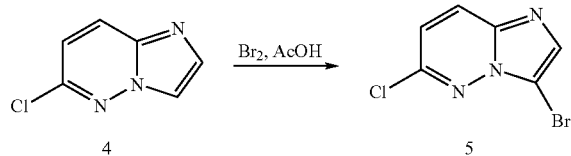

The 6-Chloro-imidazo[1,2-b]pyridazine (4) (500 mg, 0.0032 mol) was taken in glacial acetic acid (5 ml) and bromine (0.4 ml) was added slowly at room temperature. After 20 mins solid precipitated out which was filtered. The solid was washed with ether (3×15 ml) and dried under air to furnish 3-Bromo-6-chloro-imidazo[1,2-b]pyridazine (5) (400 mg, yield=60%).

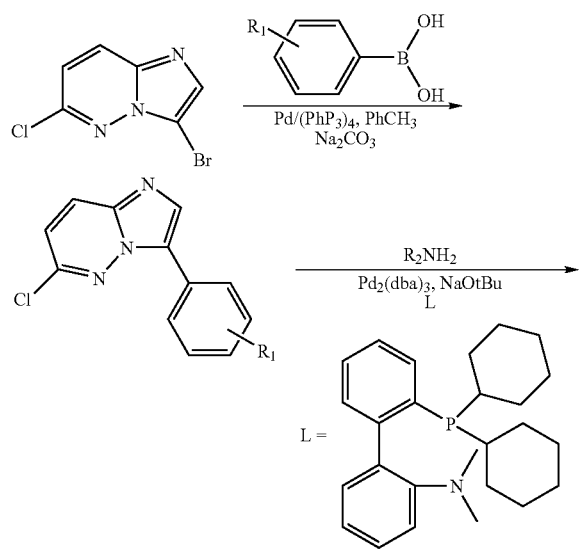

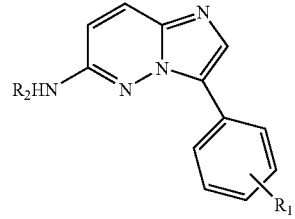

4. General procedure to make 6-chloro-3-substituted-imidazo[1,2-b]pyridazin

A reaction mixture containing 3-bromo-6-chloro-imidazo[1,2-b]pyridazine (0.43 mmol), Boronic acid (0.43 mmol), Pd(PhP3)$_4$ (7.74 umol, 0.018 eq) and NaCO3 (2M, 0.43 mmol) in 5 mL of toluene-MeOH (4:1) was degassed with Ar for 10 min. The reaction was refluxed overnight. The mixture was filtered through MgSO$_4$ and concentrated under vacuum. The residue was purified by combiflash (0% to 70 EtOAc/Hexane) to give desired products.

5. General procedure to make 3,6-disubstituted-imidazo[1,2-b]pyridazin

A reaction mixture containing 6-chloro-3-substituted-imidazo[1,2-b]pyridazin (0.096 mmol), amine (0.191 mmol), ligand (0.014 mmol, 0.15 eq), Pd2(dba)$_3$ (7.17 umol, 0.075 eq) and NaOtBu (0.136 mmol, 1.4 eq) in 5 mL of toluene was degassed with Ar for 10 min. The mixture was refluxed overnight. Concentration and preparative TLC purification afforded desired products.

12-(3-(3-(dimethylamino)phenyl)imidazo[1,2-b]pyridazin-6-ylamino)butan-1-ol (Compound 7-4)

$^1$H-NMR: (400 MHz, CD$_3$OD) 7.92 (m, 2H), 7.65 (s, 1H), 7.30 (m, 2H), 6.94 (d, J=10 Hz, 1H), 6.81 (m, 1H), 4.26 (m, 1H), 4.20 (m, 1H), 3.01 (s, 6H), 1.04 (t, J=7.6 Hz, 3H), MS m/z: 326.1, 255.2.

2-(3-(4-fluorophenyl)imidazo[1,2-b]pyridazin-6-ylamino)butan-1-ol (Compound 7-10)

$^1$H-NMR (400 MHz, CD$_3$OD) 8.09 (m, 2H), 7.92 (m, 2H), 7.25 (t, J=8.5 Hz, 2H), 6.97 (d, J=9.4 Hz, 1H), 4.45 (m, 1H), 4.21 (m, 1H), 3.17 (m, 1H), 1.68 (m, 1H), 1.52 (m, 1H), 1.06 (t, J=7.5 Hz, 3H).

2-(3-(3-fluorophenyl)imidazo[1,2-b]pyridazin-6-ylamino)butan-1-ol (Compound 7-11)

$^1$H-NMR (400 MHz, CD$_3$OD) 7.96 (m, 3H), 7.88 (d, J=7.8 Hz, 1H), 7.50 (m, 1H), 7.13 (m, 1H), 7.00 (d, J=8.6 Hz, 1H), 4.50 (m, 1H), 4.23 (m, 1H), 3.21 (m, 1H), 1.70 (m, 1H), 1.54 (m, 1H), 1.06 (t, J=7.6 Hz, 3H).

N-cyclopentyl-3-(3-fluorophenyl)imidazo[1,2-b]pyridazin-6-amine (Compound 7-15)

$^1$H-NMR (400 MHz, CD$_3$OD) 8.17 (d, J=11.3 Hz, 1H), 7.90 (d, J=6.8 Hz, 1H), 7.82 (s, 1H), 7.61 (d, J=8.5 Hz, 1H), 7.4 (m, 1H), 7.03 (m, 1H), 6.72 (d, J=9.5 Hz, 1H), 4.16 (m, 1H), 1.77 (m, 4H), 1.66 (m, 4H).

2-(3-(3-(trifluoromethoxy)phenyl)imidazo[1,2-b]pyridazin-6-ylamino)butan-1-ol (Compound 7-17)

$^1$H-NMR (400 MHz, CD$_3$OD) 8.24 (s, 1H), 8.04 (s, 1H), 7.97 (m, 2H), 7.57 (t, J=6.2 Hz, 1H), 7.27 (d, J=8.2 Hz, 1H), 7.02 (dd, J$_1$=1.4 Hz, J$_2$=9.6 Hz, 1H), 4.78 (d, J=10.9 Hz, 1H), 4.25 (t, J=8.9 Hz, 1H), 1.64 (m, 2H), 1.08 (t, J=7.6 Hz, 3H).

(R)-1-(3-(3-(trifluoromethoxy)phenyl)imidazo[1,2-b]pyridazin-6-yloxy)butan-2-amine (Compound 7-18)

$^1$H-NMR (400 MHz, CD$_3$OD) 8.24 (s, 1H), 8.02 (s, 1H), 7.98 (t, J=9.57 Hz, 2H), 7.58 (t, J=7.8 Hz, 1H), 7.27 (d, J=9.57 Hz, 1H), 7.02 (d, J=9.57 Hz, 1H), 4.48 (m, 1H), 4.25 (m, 1H), 1.71~1.56 (m, 2H), 1.08 (m, 3H).

(S)-1-(3-(3-(trifluoromethoxy)phenyl)imidazo[1,2-b]pyridazin-6-yloxy)butan-2-amine (Compound 7-19)

$^1$H-NMR (400 MHz, CD$_3$OD) 8.22 (s, 1H), 8.02 (s, 1H), 7.95 (m, 2H), 7.55 (t, J=8.2 Hz, 1H), 7.27 (m, 1H), 7.00 (dd, J1=9.9 Hz, 1H), 4.42 (m, 1H), 4.18 (m, 1H), 1.67~1.51 (m, 2H), 1.06 (m, 3H).

N-(cyclopropylmethyl)-3-(3-(trifluoromethoxy)phenyl)imidazo[1,2-b]pyridazin-6-amine (Compound 7-20)

$^1$H-NMR (400 MHz, CD$_3$OD) 8.43 (s, 1H), 7.97 (d, J=7.8 Hz, 1H), 7.85 (s, 1H), 7.62 (d, J=9.5 Hz, 1H), 7.52 (t, J=8.2 Hz, 1H), 7.20 (d, J=7.5 Hz, 1H), 6.75 (d, J=9.3 Hz, 1H), 3.21 (d, J=6.8 Hz, 2H), 1.2 (m, 1H), 0.55 (m, 2H), 0.28 (m, 2H).

N-(3-(6-(1-hydroxybutan-2-ylamino)imidazo[1,2-b]pyridazin-3-yl)phenyl)methanesulfonamide (Compound 7-23)

$^1$H-NMR (400 MHz, CD$_3$OD) 8.29 (s, 1H), 7.95 (s, 1H), 7.92 (m, 1H), 7.74 (d, J=7.8 Hz, 1H), 7.44 (t, J=7.8 Hz, 1H), 7.18 (m, 1H), 6.96 (m, 1H), 4.51 (m, 1H), 4.36 (m, 1H), 3.24 (m, 1H), 3.00 (s, 3H), 1.74 (m, 1H), 1.60 (m, 1H), 1.05 (t, J=7.5 Hz, 3H).

2-(3-(3-(trifluoromethyl)phenyl)imidazo[1,2-b]pyridazin-6-ylamino)butan-1-ol (Compound 7-24)

$^1$H-NMR (400 MHz, CD$_3$OD) 8.64 (s, 1H), 8.22 (s, 1H), 8.06 (s, 1H), 7.94 (m, 1H), 7.65 (s, 2H), 7.00 (d, J=9.9 Hz, 1H), 4.45 (m, 1H), 4.19 (t, J=8.2 Hz, 1H), 3.20 (m, 1H), 1.60 (m, 2H), 1.04 (t, J=8.5 Hz, 3H).

N-(cyclopropylmethyl)-3-(3-(trifluoromethyl)phenyl)imidazo[1,2-b]pyridazin-6-amine (Compound 7-25)

$^1$H-NMR (400 MHz, CD$_3$OD) 8.82 (s, 1H), 8.19 (s, 1H), 7.86 (s, 1H), 7.60 (m, 3H), 6.74 (m, 1H), 3.20 (m, 2H), 1.18 (m, 1H), 0.55 (m, 2H), 0.26 (m, 2H).

tert-butyl 4-((3-(3-(trifluoromethoxy)phenyl)imidazo[1,2-b]pyridazin-6-ylamino) methyl)piperidine-1-carboxylate Compound (7-27)

$^1$H-NMR (400 MHz, CD$_3$OD) 8.39 (s, 1H), 7.96 (d, J=8.2 Hz, 1H), 7.85 (s, 1H), 7.62 (dd, J1=2.0 Hz, J2=9.9 Hz, 1H), 7.49 (m, 1H), 7.21 (d, J=8.2 Hz, 1H), 6.71 (dd, J1=2.0 Hz, J2=9.57 Hz, 1H), 4.07 (m, 4H), 3.26 (m, 4H), 1.82 (d, J=12.7 Hz, 2H), 1.42 (s, 9H), 1.57 (m, 1H).

N-(piperidin-4-ylmethyl)-3-(3-(trifluoromethoxy)phenyl)imidazo[1,2-b]pyridazin-6-amine (Compound 7-28)

$^1$H-NMR (400 MHz, CD$_3$OD) 8.37 (s, 1H), 7.99 (d, J=8.2 Hz, 1H), 7.88 (s, 1H), 7.66 (d, J=9.2 Hz, 1H), 7.54 (t, J=8.2 Hz, 1H), 7.24 (d, J=7.24 Hz, 1H), 6.75 (d, J=9.5 Hz, 1H), 2.94 (m, 4H), 2.04 (m, 4H), 1.44 (m, 1H).

N-((1-methylpiperidin-4-yl)methyl)-3-(3-(trifluoromethoxy)phenyl)imidazo[1,2-b]pyridazin-6-amine (Compound 7-29)

$^1$H-NMR (400 MHz, CD$_3$OD) 8.38 (s, 1H), 8.00 (d, J=7.9 Hz, 1H), 7.86 (s, 1H), 7.64 (m, 1H), 7.53 (t, J=8.2H, 1H), 7.22 (d, J=7.5 Hz, 1H), 6.74 (d, J=9.9 Hz, 1H), 3.00 (d, J=12 Hz, 2H), 2.30 (s, 3H), 1.90 (d, J=12.6 Hz, 3H), 1.38 (m, 2H) 2.20 (t, J=11.6 Hz, 2H).

N-(2-(pyrrolidin-1-yl)ethyl)-3-(3-(trifluoromethoxy)phenyl)imidazo[1,2-b]pyridazin-6-amine Compound (7-30)

$^1$H-NMR (400 MHz, CD$_3$OD): 8.29 (s, 1H), 8.02 (d, J=7.6 Hz, 1H), 7.84 (s, 1H), 7.64 (d, J=9.6 Hz, 1H), 7.53 (t, J=8 hz, 1H), 7.31 (m, 1H), 7.22 (d, J=8.4 Hz, 1H), 6.74 (d, J=9.6 Hz, 1H), 3.56 (t, J=6.8 Hz, 2H), 2.81 (t, J=6.8 Hz, 2H), 2.63 (s, 4H), 1.81 (m, 4H).

Example 5

Synthesis of imidazo[1,2-B]pyridazine Compounds AND 7-methyl-imidazo[1,2-B]pyridazine Compounds Additional compounds of the invention, including illustrative compounds set forth in Table VII, were made according to the following synthetic examples. In these examples, Compound 7-12 was prepared as described above in Example 2, while compound 11 was prepared as follows:

6-chloro-5-methylpyridazin-3-amine 7

3,6-dichloro-4-methylpyridazine 6 (1 g) was dissolved in 5 mL of ethanol and was added ammonium hydroxide (10 mL). The resulting reaction mixture was sealed in a pressure bottle and heated to 100° C. for 48 hours. The reaction mixture is cooled and the solvents were evaporated and purified by CombiFlash Companion using Hexane/DCM 40:60 solvent system (4 g normal phase RediSep Flash column with run time min at flow 18 mL/min) gave 0.640 g (72.7%) of 7 as yellow solid).

$^1$H-NMR (300 MHz, CD$_3$OD) 7.08 (s, 1H), 4.72 (s, 2H), 2.27 (s, 3H), ESI-MS m/z 143.9 (M+H)$^+$.

6-chloro-7-methylimidazo[1,2-b]pyridazine 8

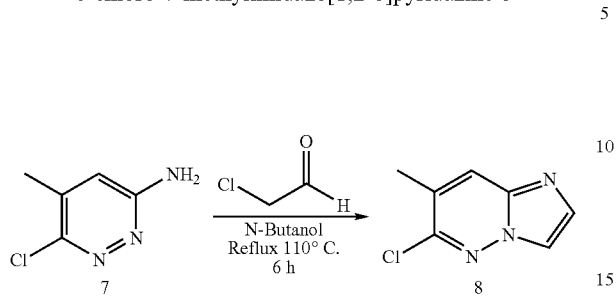

6-chloro-5-methylpyridazin-3-amine 7 (0.6 g, 4.18 mmol) was dissolved in n-butanol (10 ml) and chloroacetaldehyde (0.328 g, 4.18 mmol) was added. The reaction was refluxed for 6 hrs and n-butanol was removed under reduced pressure. The crude product was purified by column chromatography (DCM/hexane, 70:30) to afford compound 8 (0.234 g, yield=33.4%).

$^1$H-NMR (300 MHz, CD$_3$OD) 8.66 (s, 1H), 8.05 (d, J=1.7 Hz, 1H), 7.96 (d, J=8.2 Hz, 1H), 2.58 (s, 3H), ESI-MS m/z 167.8 (M+H)$^+$.

3-bromo-6-chloro-7-methylimidazo[1,2-b]pyridazine 9

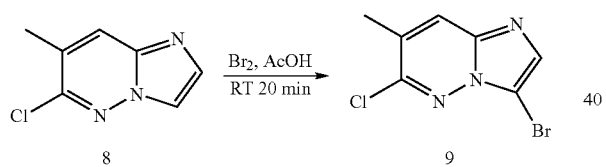

The 6-chloro-7-methylimidazo[1,2-b]pyridazine 8 (0.230 g, 1.372 mmol) was taken in glacial acetic acid (10 ml) and bromine (0.070 ml, 1.372 mmol) was added slowly at room temperature. After 20 mins the solvents were evaporated the obtained brown solid was washed with ether (3×15 ml) and dried under air to furnish compound 9 (0.236 g, yield 69.8%).

$^1$H-NMR (300 MHz, CD$_3$OD) 7.79 (d, J=7.32 Hz, 1H), 6.93 (s, 1H), 2.64 (s, 3H), ESI-MS m/z 247.9 (M+H)$^+$.

6-chloro-7-methyl-3-(3-(trifluoromethoxy)phenyl) imidazo[1,2-b]pyridazine 11

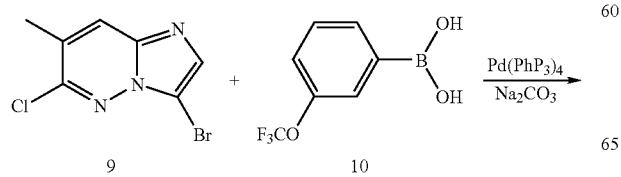

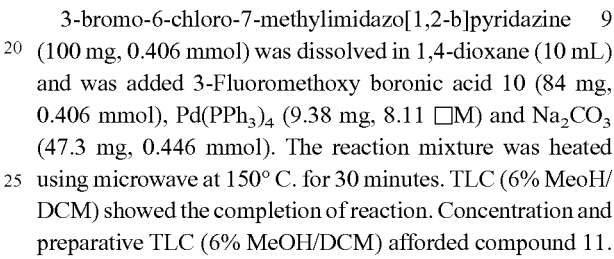

3-bromo-6-chloro-7-methylimidazo[1,2-b]pyridazine 9 (100 mg, 0.406 mmol) was dissolved in 1,4-dioxane (10 mL) and was added 3-Fluoromethoxy boronic acid 10 (84 mg, 0.406 mmol), Pd(PPh$_3$)$_4$ (9.38 mg, 8.11 μM) and Na$_2$CO$_3$ (47.3 mg, 0.446 mmol). The reaction mixture was heated using microwave at 150° C. for 30 minutes. TLC (6% MeOH/DCM) showed the completion of reaction. Concentration and preparative TLC (6% MeOH/DCM) afforded compound 11.

$^1$H-NMR (300 MHz, CDCl3) 8.01 (d, J=1.2 Hz, 1H), 7.95 (m, 2H), 7.51 (t, J=8.1 Hz, 1H), 7.21 (m, 1H), 6.96 (m, 1H), 2.69 (s, 3H). 1.54 (s, 3H). $^{19}$F-NMR (300 MHz, CDCl3)-59.08.

(S)-2-(3-(3-(trifluoromethoxy)phenyl)imidazo[1,2-b] pyridazin-6-ylamino)butan-1-ol (Compound 7-32)

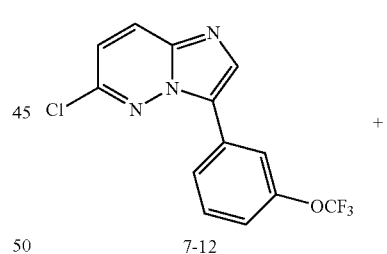

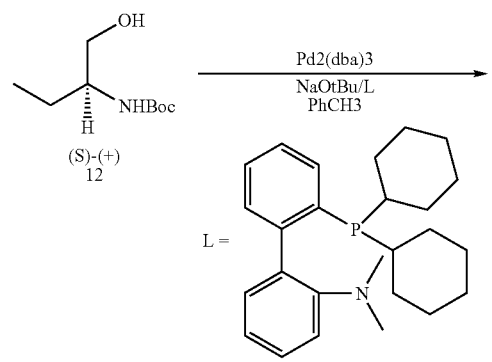

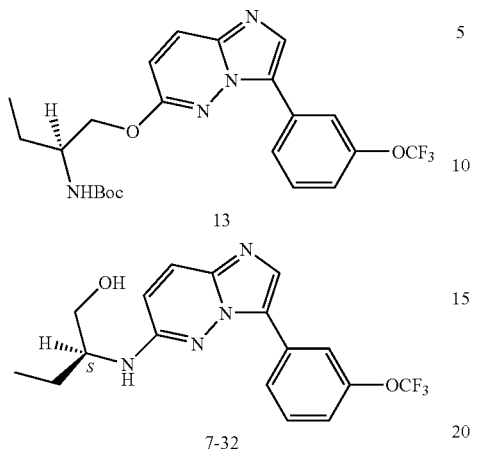

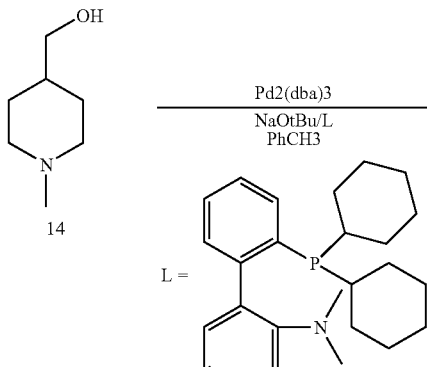

To the toluene (10 mL) solvent was added Compound 7-12 (100 mg, 0.319 mmol), N-Boc-(S)-(+)-2-amino-1-butanol 12 (121 mg, 0.638 mmol), ligand (18.82 mg, 0.048 mmol), NaOtBu (43.5 mg, 0.453 mmol) and Pd$_2$(dba)$_3$ (21.90, 0.024 mmol). The resulting reaction mixture was degassed for 10 min under argon and then was microwave for 1 h at 165° C. Concentration and preparative TLC (10% MeOH/DCM) afforded Compound 13 and Compound 7-32. NMR indicated that 7-32 is a product with Boc removed. The crude product was concentrated and preparative TLC was performed with 10% MeOH/DCM solvent system afforded 27 mg of 7-32 as a yellow solid (23.12%).

$^1$H-NMR (400 MHz, CD$_3$OD) 8.30 (s, 1H), 8.02 (d, J=7.8 Hz, 1H), 7.84 (s, 1H), 7.62 (d, J=9.6 Hz, 1H), 7.53 (t, J=8.2 Hz, 1H), 7.21 (d, J=8.5 Hz, 1H), 6.78 (d, J=9.6 Hz, 1H), 3.93 (t, J=5.8 Hz, 1H), 3.76 (m, 1H), 3.65 (m, 1H), 1.73 (m, 2H), 1.03 (t, J=7.5 Hz, 3H). ESI-MS m/z 367.13 (M+H)$^+$.

6-((1-methylpiperidin-4-yl)methoxy)-3-(3-(trifluoromethoxy)phenyl)imidazo[1,2-b]pyridazine (Compound 7-33)

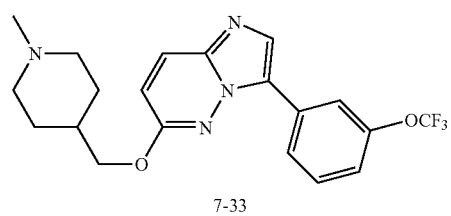

To the toluene (5 mL) solvent was added Compound 7-12 (50 mg, 0.159 mmol), (1-methylpiperidine-4-yl)methanol 14 (30.9 mg, 0.239 mmol), ligand (9.41 mg, 0.024 mmol), NaOtBu (21.75 mg, 0.226 mmol) and Pd$_2$(dba)$_3$ (10.95, 0.012 mmol). The resulting reaction mixture was degassed for 10 min under argon and then was heated to reflux for 12 h. Concentration and preparative TLC (10% MeOH/DCM) afforded 17.6 mg of Compound 7-33.

$^1$H-NMR (400 MHz, CD$^3$OD) 8.30 (s, 1H), 8.05 (s, 1H), 7.97 (m, 3H), 7.58 (t, J=8.2 Hz, 1H), 6.96 (d, J=9.9 Hz, 1H), 4.29 (d, J=6.5 Hz, 2H), 3.94 (d, J=6.15 Hz, 1H), 3.07 (t, J=12.64 Hz, 4H), 2.33 (t, J=12.30 Hz, 4H), 2.02 (s, 3H). ESI-MS m/z 407.18 (M+H)$^+$.

7-methyl-6-((1-methylpiperidin-4-yl)methoxy)-3-(3 (trifluoromethoxy)phenyl) imidazo[1,2-b]pyridazine (Compound 7-34)

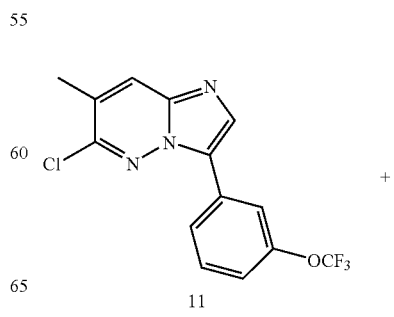

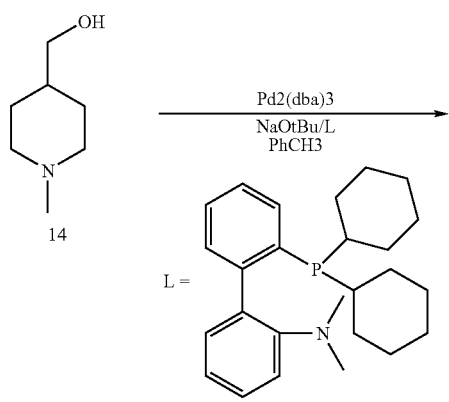

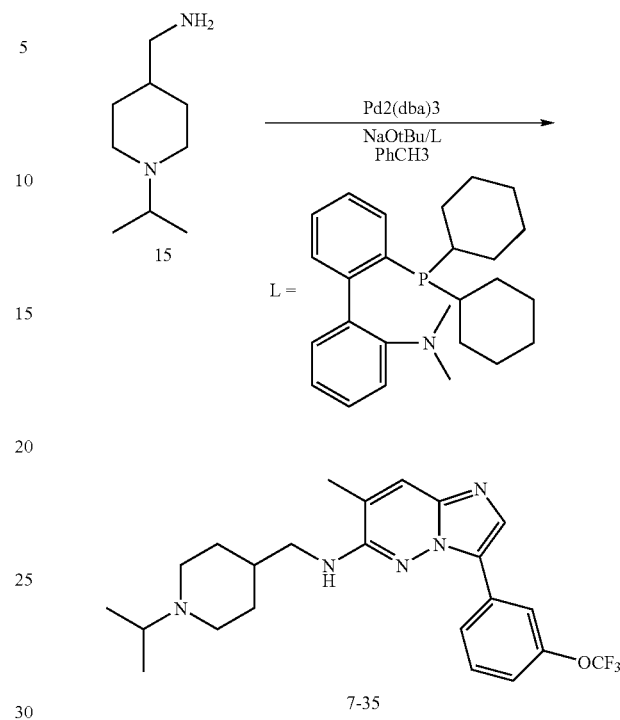

To the toluene (5 mL) solvent was added Compound 11 (80 mg, 0.224 mmol), (1-methylpiperidine-4-yl)methanol 14 (47.3 mg, 0.366 mmol), ligand (14.41 mg, 0.037 mmol), NaOtBu (33.3 mg, 0.347 mmol) and Pd$_2$(dba)$_3$ (16.77, 0.018 mmol). The resulting reaction mixture was degassed for 10 min under argon and then was heated with microwave at 165° C. Concentration and preparative TLC (10% MeOH/DCM) afforded 111.5 mg (11.2%) of Compound 7-34.

$^1$H-NMR (300 MHz, CD$_3$OD) 8.27 (s, 1H), 7.96 (m, 2H), 7.55 (m, 1H), 7.23 (d, J=8.1 Hz, 1H), 6.76 (s, 1H), 4.18 (s, 2H), 2.96 (d, J=11.7 Hz, 1H), 2.56 (s, 3H), 2.31 (s, 3H), 2.11 (t, J=12.3 Hz, 2H), 1.88 (d, J=12.3 Hz, 4H), 1.44 (d, J=12.6 Hz, 2H). ESI-MS m/z 421.18 (M+H)$^+$.

N-((1-isopropylpiperidin-4-yl)methyl)-3-(3(trifluoromethoxy)phenyl)imidazo[1,2b]pyridazin-6-amine (Compound 7-35)

To the toluene (10 mL) solvent was added Compound 7-12 (10 mg, 0.319 mmol), (1-isopropylpiperidine-4-yl)methanamine 15 (74.9 mg, 0.478 mmol), ligand (18.82 mg, 0.048 mmol), NaOH (43.5 mg, 0.453 mmol) and Pd$_2$(dba)$_3$ (21.90, 0.024 mmol). The resulting reaction mixture was degassed for 10 min under argon and then was heated to reflux for 12 h. Concentration and preparative TLC (10% MeOH/DCM) afforded 11 mg (7.96%) of Compound 7-35.

$^1$H-NMR (300 MHz, CD$_3$OD) 7.60 (s, 1H), 7.18 (d, J=9.3 Hz, 1H), 7.07 (s, 1H), 6.84 (d, J=9.3 Hz, 1H), 6.73 (t, J=8.1 Hz, 1H), 6.43 (d, J=6.3 Hz, 1H), 5.94 (d, J=9.9 Hz, 1H), 2.85 (s, 1H), 2.14 (m, 3H), 1.93 (m, 2H), 1.42 (m, 3H), 1.07 (m, 4H), 0.286 (2s, 2CH$_3$) ESI-MS m/z 434.23 (M+H)$^+$.

Cyclopropyl(4-((3-(3-(trifluoromethoxy)phenyl) imidazo[1,2-b]pyridazin-6-ylamino) methyl)piperidin-1-yl)methanone (Compound 7-36)

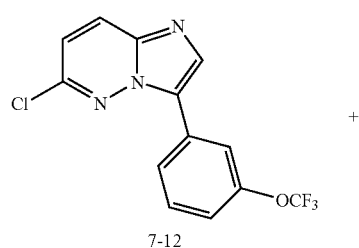

+

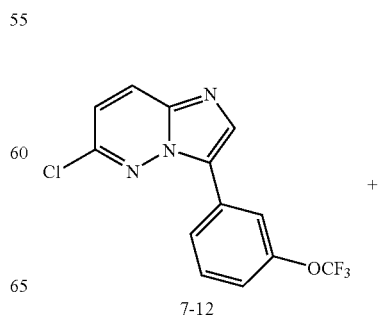

+

-continued

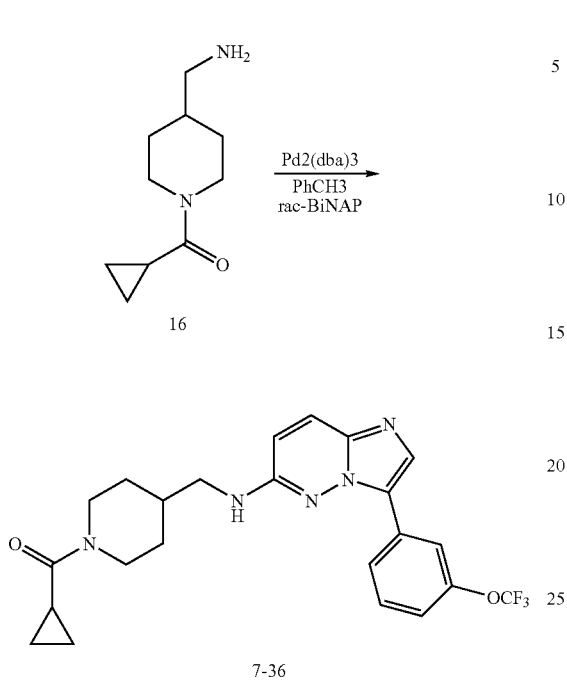

7-36

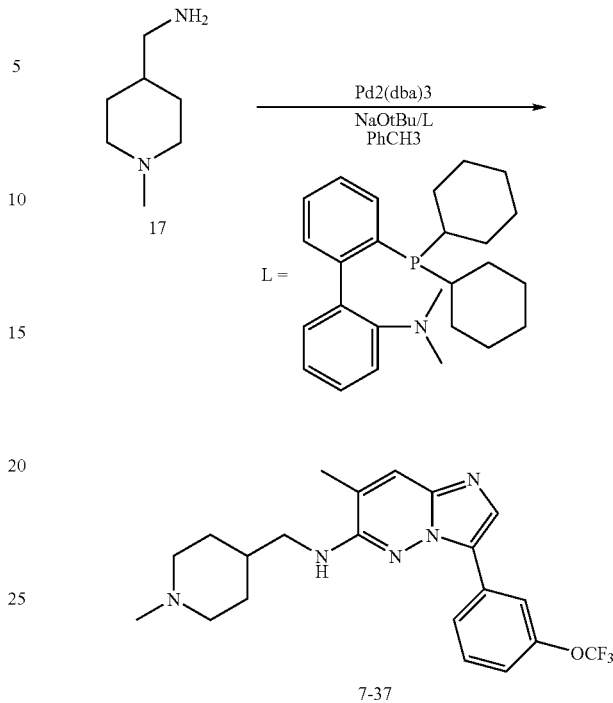

7-37

To the toluene (10 mL) solvent was added Compound 7-12 (10 mg, 0.319 mmol), (1-cyclopropylcarbonylpiperidine-4-yl)methanamine 16 (69.7 mg, 0.383 mmol), rac-BINAP (7.94 mg, 0.013 mmol) and Pd$_2$(dba)$_3$ (5.84, 6.38 □M). The resulting reaction mixture was degassed for 10 min under argon and then was heated to reflux for 12 h. Concentration and preparative TLC (10% MeOH/DCM) afforded 29 mg (19.8%) of Compound 7-36.

$^1$H-NMR (300 MHz, CD$_3$OD) 7.59 (s, 1H), 7.16 (d, J=7.2 Hz, 1H), 7.04 (d, J=6.3 Hz, 1H), 6.81 (m, 1H), 6.70 (m, 1H), 6.40 (d, J=6.3 Hz, 1H), 5.90 (m, 1H), 3.70 (m, 1H), 3.54 (m, 1H), 2.36 (m, 1H), 1.83 (m, 1H), 1.28 (m, 1H), 1.12 (m, 3H), 0.4 (m, 2H), 0.027 (m, 4H). ESI-MS m/z 460.20 (M+H)$^+$.

7-Methyl-N-((1-methylpiperidin-4-yl)methyl)-3-(3-(trifluoromethoxy)phenyl)-imidazo[1,2-b]pyridazin-6-amine (Compound 7-37)

To the toluene (5 mL) solvent was added Compound 11 (57 mg, 0.174 mmol), (1-methylpiperidine-4-yl)methanamine 17 (26.8 mg, 0.209 mmol), ligand (10.27 mg, 0.026 mmol), NaOtBu (23.40 mg, 0.244 mmol) and Pd$_2$(dba)$_3$ (11.95, 0.013 mmol). The resulting reaction mixture was degassed for 10 min under argon and then was heated with microwave at 150° C. for 1 h. Concentration and preparative TLC (10% MeOH/DCM) afforded 5.3 mg (7.26%) of Compound 7-37.

$^1$H-NMR (300 MHz, CD$_3$OD) 8.35 (s, 1H), 8.01 (d, J=8.4 Hz, 1H), 7.83 (s, 1H), 7.51 (t, J=7.8 Hz, 2H), 7.21 (d, J=8.1 Hz, 2H), 3.65 (m, 2H), 2.36 (m, 3H), 2.98 (d, J=11.4 Hz, 2H), 2.48 (m, 2H), 2.26 (d, J=0.9 Hz, 3H), 2.24 (s, 3H), 1.91 (m, 4H), 1.32 (m, 1H). $^{19}$F-NMR (300 Hz, CD$_3$OD)-56.456, FTMS+p MALDI: 420.20113 (M+H)$^+$, Theory Exact Mass: 420.20112.

N-((1-ethylpiperidin-4-yl)methyl)-7-methyl-3-((trifluoromethoxy)phenyl)imidazo[1,2-b]pyridazin-6-amine (Compound 7-38)

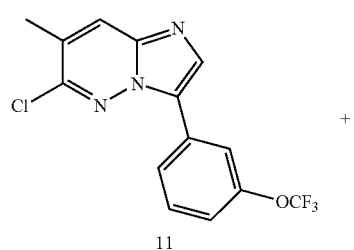

11

+

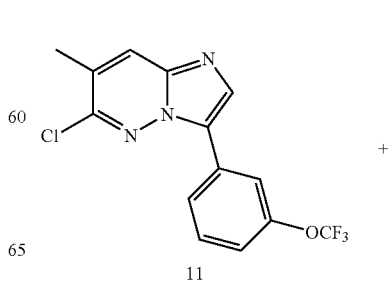

11

+

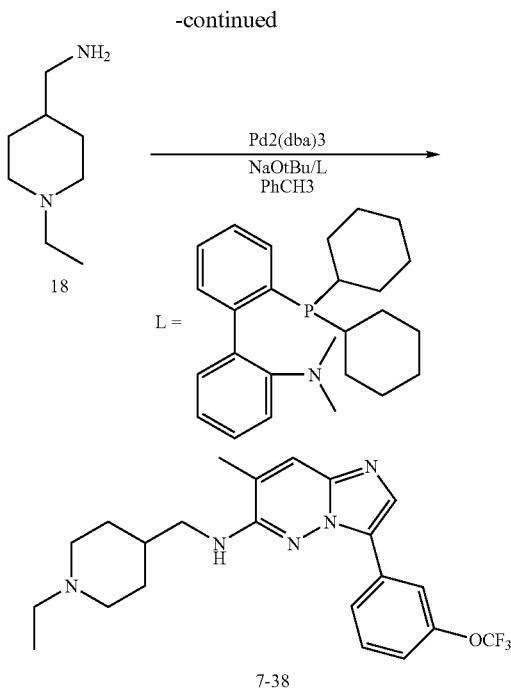

To the toluene (5 mL) solvent was added Compound 11 (50 mg, 0.153 mmol), (1-ethylpiperidine-4-yl)methanamine 18 (26 mg, 0.183 mmol), ligand 9.01 mg, 0.023 mmol), NaOtBu (20.53 mg, 0.214 mmol) and Pd$_2$(dba)$_3$ (10.48, 0.011 mmol). The resulting reaction mixture was degassed for 10 min under argon and then was heated with microwave at 150° C. for 1.5 h. Concentration and preparative TLC (10% MeOH/DCM) afforded 11.9 mg (17.99%) of Compound 7-38.

$^1$H-NMR (300 MHz, CD$_3$OD) 8.335 (s, 1H), 7.99 (d, J=7.8 Hz, 1H), 7.81 (s, 1H), 7.49 (t, J=7.8 Hz, 2H), 7.21 (m, 1H), 3.34 (m, 2H), 3.00 (d, J=11.1 Hz, 2H), 2.44 (m, 4H), 2.26 (s, 3H), 1.91 (m, 4H), 1.32 (m, 1H), 1.08 (t, J=6.9 Hz, 3H). $^{19}$F-NMR (300 Hz, CD$_3$OD)-56.423, FTMS+p MALDI: 434.36365 (M+H)$^+$, Theory Exact Mass: 433.20895.

N-((1-ethylpiperidin-4-yl)methyl)-3-(3-(trifluoromethoxy)phenyl)imidazo[1,2-b]pyridazin-6-amine (Compound 7-39)

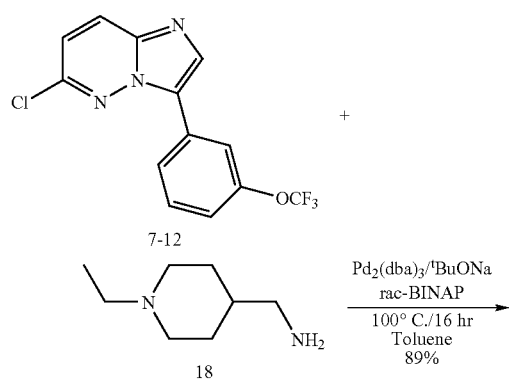

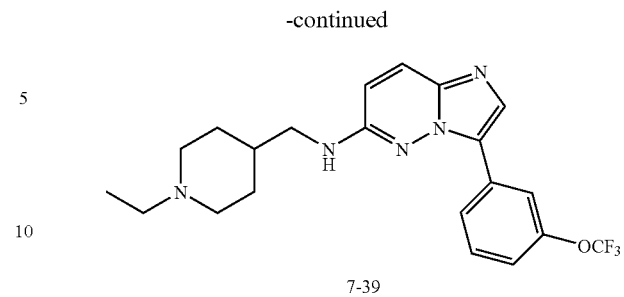

A solution of Compound 7-12 (0.250 g, 0.797 mmol) and (1-ethylpiperidin-4-yl)methanamine 18 (0.113 g, 0.797 mmol) in toluene (10 mL) was added sodium tertiary butoxide (0.138 g, 1.435 mmol), rac-BINAP (0.030 g, 0.048 mmol) and Pd2(dba)$_3$ (0.022 g, 0.024 mmol) and the mixture was heated at 100° C. for overnight. After 16 h, the resulting dark brown solution was cooled down and was concentrated under reduced pressure. The solid was further purified by using combiflash chromatography (6 g column), eluent: 5% TEA in ethyl acetate/hexane (10-100) removed the impurities and 5% TEA in ethyl acetate/CH$_3$OH (90:10) to obtain Compound 7-39 (89%).

$^1$H-NMR (DMSO-d6/300 MHz): 8.50 (s, 1H), 8.06 (d, J=13.2 Hz, 1H), 7.77 (d, J=9.9 Hz, 1H), 7.57 (t, J=7.8 Hz, 1H), 7.28 (m, 2H), 6.76 (d, J=9.9 Hz, 1H), 3.35 (m, 2H), 3.16 (m, 2H), 2.87 (d, J=9.9 Hz, 2H), 2.27 (m, 2H), 1.76 (m, 4H), 1.22 (m, 1H), 0.97 (t, J=6.9 Hz, 3H). ESI-MS m/z 420.2 (M+H)$^+$.

Compounds 7-40 through 7-51 were prepared according to the following general method:

To a solution of 6-Chloro-3-(2-methoxy-5-(trifluoromethoxy)-phenyl)imidazo[1,2-b]pyridazine or 6-Chloro-3-(2-methoxy-4-(trifluoromethoxy)-phenyl)imidazo[1,2-b]pyridazine (0.149 g, 0.434 mmol) and amine (0.434 mmol) in toluene (5 mL) was added sodium tertiary butoxide (0.075 g, 0.780 mmol), rac-BINAP (0.012 g, 0.013 mmol) and Pd$_2$(dba)$_3$ (0.016 g, 0.026 mmol) and the mixture was heated at 100° C. for overnight. After 16 h, the resulting dark brown solution was cooled down and was concentrated under reduced pressure. The solid was further purified by using combiflash chromatography (6 g column): eluent: 5% TEA in ethyl acetate/hexane (10-100) to remove the impurities and 5% TEA in ethyl acetate/CH$_3$OH (90:10) to elute the desired methoxy product.

The methoxy group was removed by dissolving the methoxy compound (0.222 mmol) in anhydrous dichloromethane (DCM) (3 mL) and adding BBr$_3$ (1.0 M in DCM, 0.667 mL) at −78° C., and stirring at room temperature overnight. After 16 h, the resulting dark brown solution was quenched with NaHCO$_3$. HPLC analysis indicated that the conversion was complete. After extracting with DCM and drying, the residue was purified by using combiflash chromatography, eluent: methanol/Ethyl Acetate (5% TEA), ratio 5-50%. R$_f$=0.23, 50% Ethyl acetate (5% TEA)/CH$_3$OH; The structure is confirmed by $^1$H-NMR and mass spectrometry (MS).

3-(2-methoxy-5-(trifluoromethyl)phenyl)-N-(4-(4-methylpiperazin-1-yl)phenyl)imidazo[1,2-b]pyridazin-6-amine (Compound 7-40)

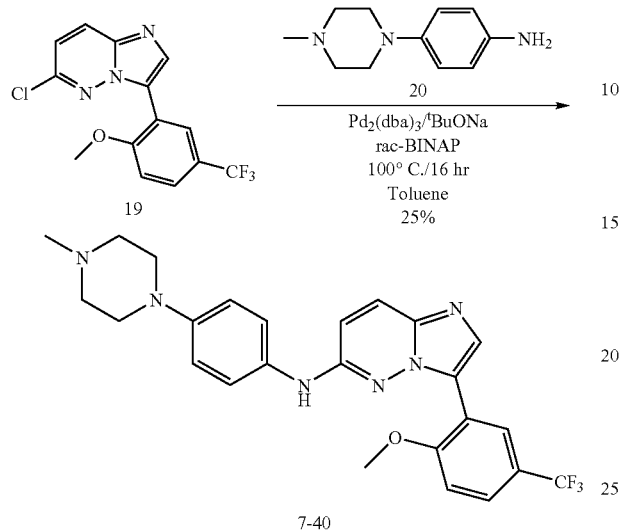

¹H-NMR (CD₃OD/400 MHz): 8.36 (d, J=2.1 Hz, 1H), 7.79 (s, 1H), 7.68 (s, 1H), 7.64 (s, 1H), 7.54 (dd, J=8.5, 1.7 Hz, 2H), 6.87 (m, 3H), 3.92 (s, 3H), 3.12 (t, J=18.3 Hz, 4H), 2.62 (t, J=18.3 Hz, 4H), 2.33 (s, 3H). ESI-MS (ES+, m/z): 483.2 (M⁺+1, 100.0).

3-(2-Hydroxy-5-(trifluoromethyl)phenyl)-N-(4-(4-methylpiperazin-1-yl)phenyl)-imidazo[1,2-b]pyridazin-6-amine (Compound 7-41)

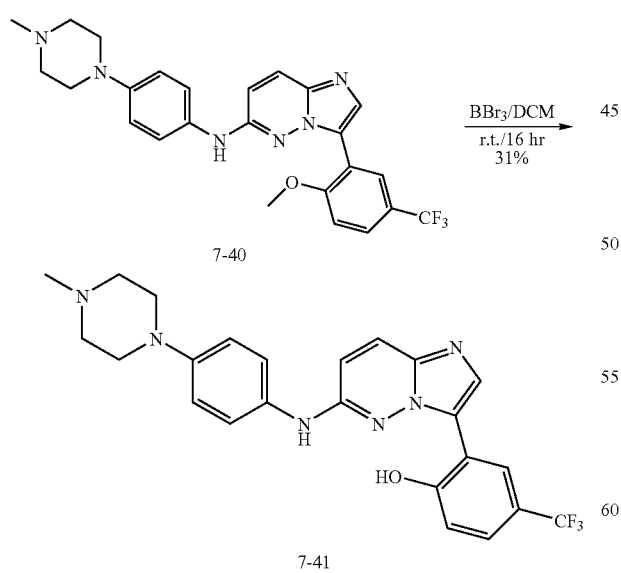

¹H-NMR (DMSO-d₆/400 MHz): 9.28 (s, 1H), 8.29 (d, J=2.1 Hz, 1H), 7.90 (d, J=9.9 Hz, 1H), 7.81 (s, 1H), 7.77 (dd, J=8.6, 2.1 Hz, 1H), 7.55 (d, J=8.9 Hz, 2H), 7.40 (d, J=8.6 Hz, 1H), 6.90 (t, J=9.9 Hz, 3H), 3.64 (d, J=12.3 Hz, 4H), 3.50 (d, J=13.3 Hz, 4H), 2.33 (s, 3H). ESI-MS (ES+, m/z): 469.3 (M⁺+1, 10.0).

3-(2-methoxy-5-(trifluoromethoxy)phenyl)-N-((1-methylpiperidin-4-yl)methyl)-imidazo[1,2-b]pyridazin-6-amine (Compound 7-42)

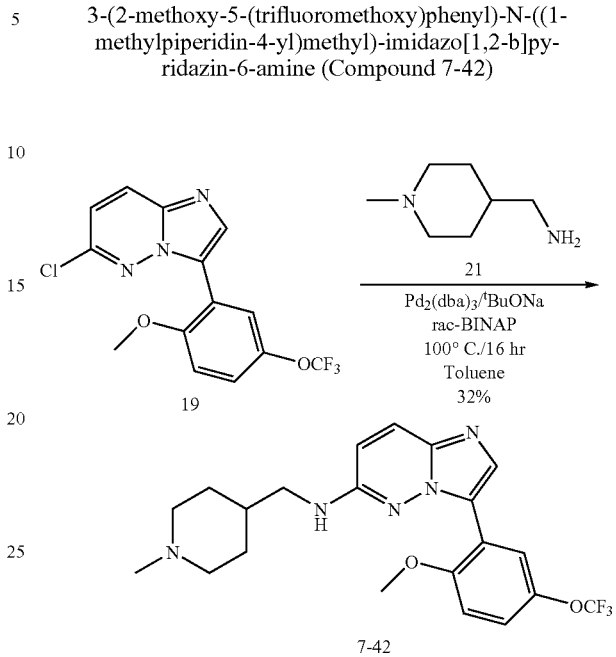

¹H-NMR (CD₃OD/400 MHz): 8.46 (d, J=2.4 Hz, 1H), 7.94 (s, 1H), 7.64 (d, J=9.6 Hz, 1H), 7.23 (dt, J=9.2, 2.0 Hz, 1H), 7.18 (d, J=9.3 Hz, 1H), 6.73 (d, J=9.6 Hz, 1H), 3.95 (s, 3H), 3.27 (m, J=18.3 Hz, 2H), 3.15 (m, J=18.3 Hz, 2H), 2.48 (s, 3H), 2.41 (t, J=18.3 Hz, 2H), 1.90 (m, J=18.3 Hz, 3H), 1.29 (m, J=18.3 Hz, 2H). ESI-MS (ES+, m/z): 436.2 (M⁺+1, 100.0).

3-(2-hydroxy-5-(trifluoromethoxy)phenyl)-N-((1-methylpiperidin-4-yl)methyl)-imidazo[1,2-b]pyridazin-6-amine (Compound 7-43)

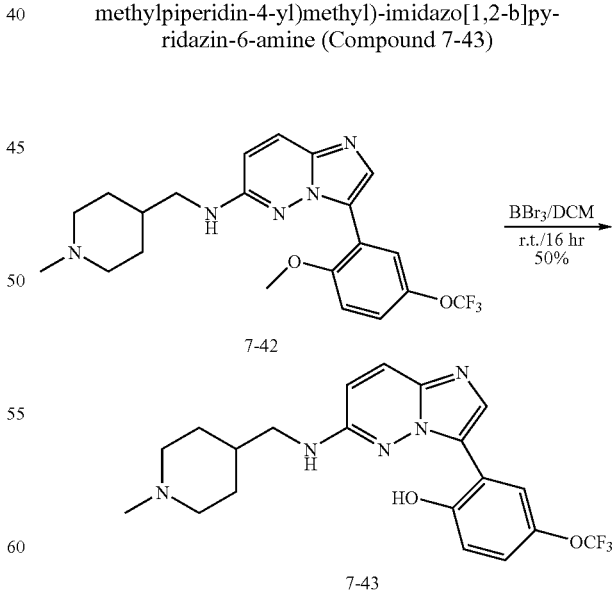

¹H-NMR (CD₃OD/400 MHz): 8.60 (d, J=2.4 Hz, 1H), 8.04 (s, 1H), 7.74 (d, J=9.9 Hz, 1H), 7.13 (m, J=9.2, 2.0 Hz, 2H), 7.04 (d, J=8.9 Hz, 1H), 6.72 (d, J=9.6 Hz, 1H), 3.13 (t, J=6.5 Hz, 4H), 2.75 (d, J=11.3 Hz, 2H), 2.48 (s, 3H), 1.81 (t, J=12.0

Hz, 2H), 1.72 (d, J=12.0 Hz, 2H), 1.60 (m, J=18.3 Hz, 1H). ESI-MS (ES+, m/z): 422.2 (M⁺+1, 100.0).

3-(2-methoxy-5-(trifluoromethoxy)phenyl)-N-(2-(1-methylpiperidin-4-yl)ethyl)-imidazo[1,2-b]pyridazin-6-amine (Compound 7-44)

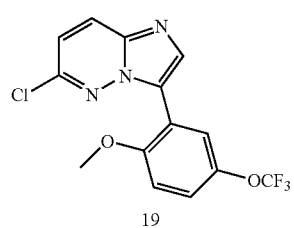 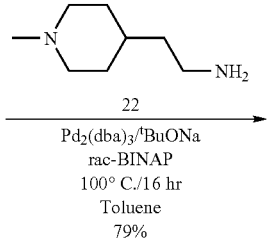

7-44

¹H-NMR (DMSO-d₆/300 MHz): 8.53 (d, J=2.7 Hz, 1H), 7.93 (s, 1H), 7.75 (d, J=9.6 Hz, 1H), 7.30 (dd, J=8.7, 3.0 Hz, 1H), 7.22 (d, J=9.3 Hz, 1H), 6.97 (t, J=5.1 Hz, 1H), 6.77 (d, J=9.3 Hz, 1H), 3.91 (s, 3H), 2.81 (d, J=11.7 Hz, 2H), 2.48 (s, 3H), 1.89 (t, J=11.7 Hz, 2H), 1.52 (d, J=12.3 Hz, 2H), 1.27 (m, 1H), 1.17 (m, 2H), 0.84 (m, 4H). ESI-MS (ES+, m/z): 450.2 (M⁺+1, 20.0).

3-(2-Hydroxyl-5-(trifluoromethoxy)phenyl)-N-(2-(1-methylpiperidin-4-yl)ethyl)-imidazo[1,2-b]pyridazin-6-amine (Compound 7-45)

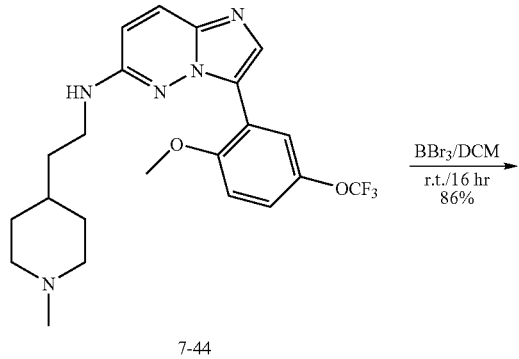

7-44

-continued

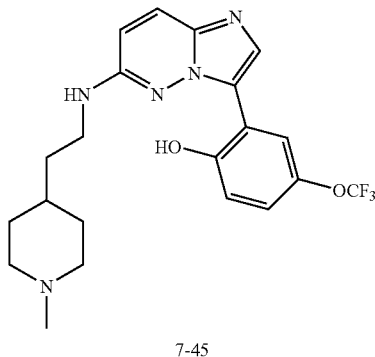

7-45

¹H-NMR (CD₃OD+CDCl₃/300 MHz): 8.01 (d, J=3.1 Hz, 1H), 7.88 (s, 1H), 7.63 (d, J=9.6 Hz, 1H), 7.07 (dd, J=8.9, 1.7 Hz, 1H), 6.97 (d, J=8.7 Hz, 1H), 6.70 (d, J=9.6 Hz, 1H), 3.34 (s, 3H), 2.90 (t, J=6.5 Hz, 2H), 2.37 (t, J=11.2 Hz, 2H), 1.69 (d, J=12.3 Hz, 2H), 1.45 (m, 1H), 1.28 (m, 2H), 0.93 (m, 4H). ESI-MS (ES+, m/z): 436.3 (M⁺+1, 20.0).

N-((1-ethylpiperidin-4-yl)methyl)-3-(2-methoxy-5-(trifluoromethoxy)phenyl)-imidazo[1,2-b]pyridazin-6-amine (Compound 7-46)

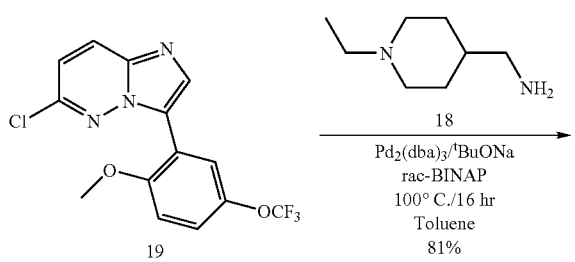

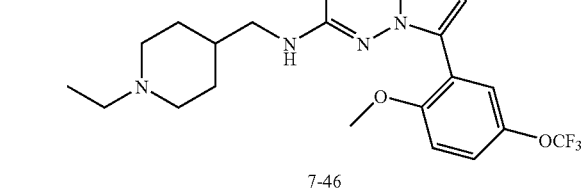

7-46

¹H-NMR (DMSO-d₆/400 MHz): 8.27 (s, 1H), 7.98 (s, 1H), 7.78 (d, J=9.9 Hz, 1H), 7.33 (d, J=8.9 Hz, 1H), 7.25 (d, J=9.2 Hz, 1H), 7.15 (t, J=5.2 Hz, 1H), 6.77 (d, J=9.6 Hz, 1H), 3.95 (s, 3H), 3.15 (t, J=5.8 Hz, 4H), 2.88 (d, J=11.3 Hz, 2H), 2.30 (q, J=7.2 Hz, 2H), 1.82 (t, J=10.9 Hz, 2H), 1.75 (d, J=13.3 Hz, 2H), 1.65 (m, 1H), 0.99 (t, J=7.2 Hz, 3H). ESI-MS (ES+, m/z): 450.2 (M⁺+1, 20.0).

79

N-((1-ethylpiperidin-4-yl)methyl)-3-(2-hydroxy-5-(trifluoromethoxy)phenyl)-imidazo[1,2-b]pyridazin-6-amine (Compound 7-47)

80

N-((1-isopropylpiperidin-4-yl)methyl)-3-(2-hydroxy-5-(trifluoromethoxy)phenyl)-imidazo[1,2-b]pyridazin-6-amine (Compound 7-49)

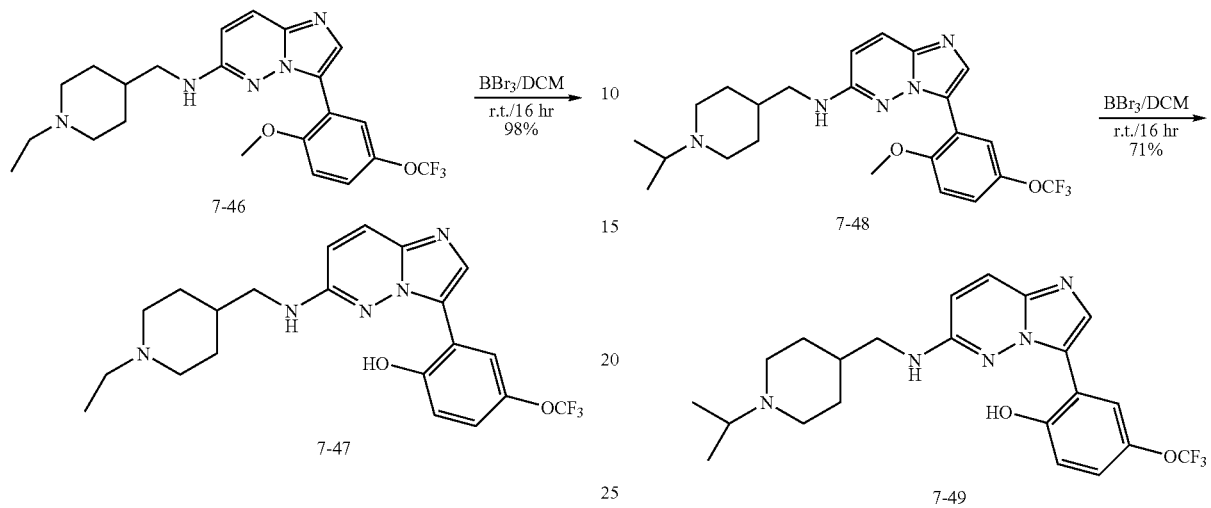

$^1$H-NMR (DMSO-d$_6$/300 MHz): 8.60 (s, 1H), 7.96 (d, J=3.6 Hz, 1H), 7.75 (dd, J=9.9, 3.6 Hz, 1H), 7.30 (d, J=8.7 Hz, 1H), 7.23 (d, J=9.0 Hz, 1H), 7.14 (s, 1H), 6.76 (d, J=9.9 Hz, 1H), 3.16 (m, 4H), 2.78 (m, 2H), 2.30 (q, J=7.2 Hz, 2H), 1.82 (m, 2H), 1.76 (m, 2H), 1.67 (m, 1H), 0.99 (t, J=7.2 Hz, 3H). ESI-MS (ES+, m/z): 436.2 (M$^+$+1, 100.0).

$^1$H-NMR (DMSO-d$_6$/300 MHz): 8.59 (s, 1H), 8.04 (d, J=2.4 Hz, 1H), 7.75 (dd, J=9.8, 2.0 Hz, 1H), 7.13 (d, J=8.3 Hz, 2H), 7.03 (d, J=6.8 Hz, 1H), 6.73 (d, J=7.8 Hz, 1H), 3.13 (m, 4H), 2.87 (m, 2H), 2.25 (m, 2H), 1.74 (m, 4H), 0.98 (d, J=6.8 Hz, 6H). ESI-MS (ES+, m/z): 450.2 (M$^+$+1, 40.0).

N-((1-isoproylpiperidin-4-yl)methyl)-3-(2-methoxy-5-(trifluoromethoxy)phenyl)-imidazo[1,2-b]pyridazin-6-amine (Compound 7-48)

N-(2-(1-ethylpiperidin-4-yl)ethyl)-3-(2-methoxy-5-(trifluoromethoxy)phenyl)-imidazo[1,2-b]pyridazin-6-amine (Compound 7-50)

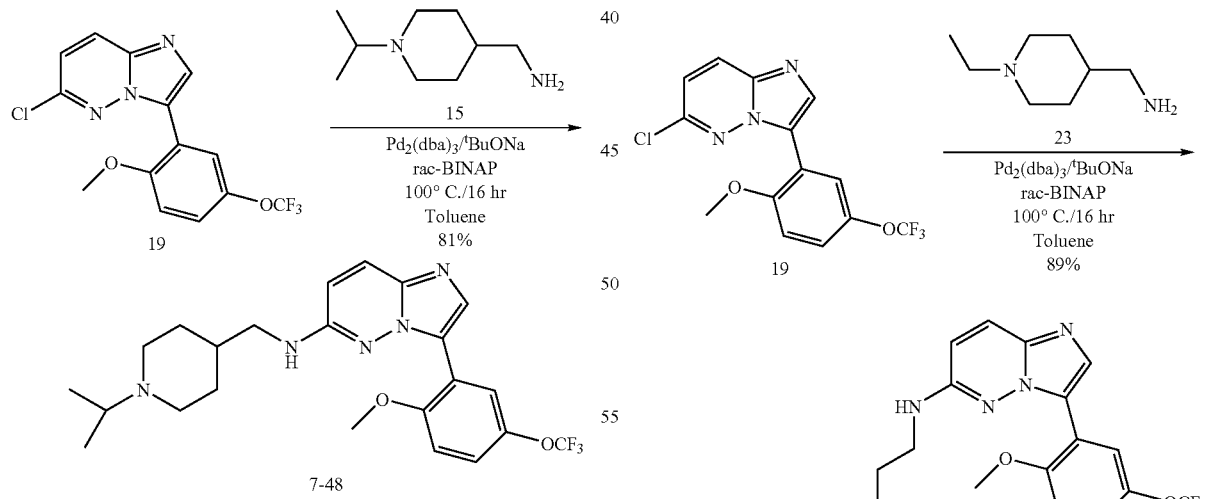

$^1$H-NMR (DMSO-d$_6$/300 MHz): 8.52 (d, J=2.1 Hz, 1H), 7.88 (s, 1H), 7.66 (d, J=10.7 Hz, 1H), 7.24 (d, J=9.0 Hz, 1H), 7.14 (d, J=13.7 Hz, 1H), 7.04 (t, J=5.2 Hz, 1H), 6.68 (d, J=9.4 Hz, 1H), 3.84 (s, 3H), 3.06 (t, J=5.9 Hz, 4H), 2.71 (d, J=8.9 Hz, 2H), 2.55 (t, J=6.5 Hz, 2H), 1.99 (t, J=9.2 Hz, 2H), 1.68 (d, J=13.3 Hz, 1H), 1.53 (m, 1H), 0.84 (d, J=7.2 Hz, 6H). ESI-MS (ES+, m/z): 464.2 (M$^+$+1, 50.0).

$^1$H-NMR (DMSO-d$_6$/300 MHz): 8.58 (d, J=2.7 Hz, 1H), 7.95 (s, 1H), 7.76 (d, J=9.7 Hz, 1H), 7.30 (dd, J=8.5, 2.0 Hz, 1H), 7.22 (d, J=9.3 Hz, 1H), 6.98 (t, J=5.2 Hz, 1H), 6.77 (d, J=9.3 Hz, 1H), 3.91 (s, 3H), 3.21 (m, 2H), 2.82 (m, 2H), 2.29 (t, J=7.4 Hz, 2H), 1.78 (m, 2H), 1.66 (m, 2H), 1.50 (m, 2H), 1.28 (m, 1H), 1.15 (m, 2H), 0.94 (t, J=7.2 Hz, 3H). ESI-MS (ES+, m/z): 464.2 (M$^+$+1, 20.0).

N-((1-isopropylpiperidin-4-yl)methyl)-3-(4-(trifluoromethoxy)phenyl)-imidazo[1,2-b]pyridazin-6-amine (Compound 7-51)

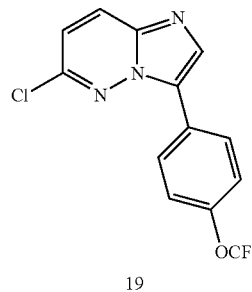

19

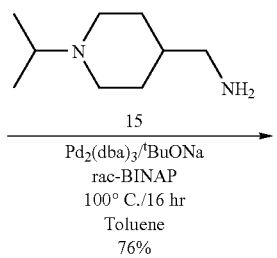

15

Pd$_2$(dba)$_3$/$^t$BuONa
rac-BINAP
100° C./16 hr
Toluene
76%

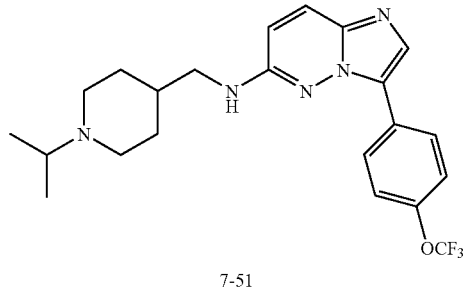

7-51

$^1$H-NMR (DMSO-d$_6$/300 MHz): 8.32 (dt, J=9.8, 2.4 Hz, 2H), 7.93 (s, 1H), 7.75 (d, J=9.3 Hz, 1H), 7.44 (d, J=8.3 Hz, 2H), 7.19 (t, J=5.4 Hz, 1H), 6.74 (d, J=9.8 Hz, 1H), 3.14 (t, J=4.9 Hz, 4H), 2.79 (d, J=11.2 Hz, 2H), 2.63 (m, 1H), 2.04 (t, J=10.3 Hz, 2H), 1.74 (m, 2H), 1.23 (m, 1H), 0.91 (d, J=6.3 Hz, 6H). ESI-MS (ES+, m/z): 434.3 (M$^+$+1, 40.0).

Example 6

Illustrative imidazo[1,2-B]pyridazine Pim-1 Kinase Inhibitors

The structures of additional Pim-1 kinase inhibitors identified according to the invention and synthesized according the synthetic procedures detailed herein are set forth in Table VII below.

TABLE VII

Illustrative Imidazo[1,2-b]Pyridazine Pim-1 Kinase Inhibitors

| Compound | Structure |
|---|---|
| 7-1 | (structure shown)<br>Chemical Formula: C$_{18}$H$_{23}$N$_5$O<br>Molecular Weight: 325.41 |
| 7-2 | 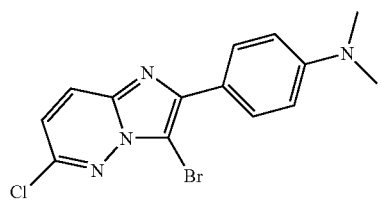<br>Chemical Formula: C$_{14}$H$_{12}$BrClN$_4$<br>Molecular Weight: 351.63 |

TABLE VII-continued

Illustrative Imidazo[1,2-b]Pyridazine Pim-1 Kinase Inhibitors

| Compound | Structure |
|---|---|
| 7-3 | Chemical Formula: $C_{14}H_{13}ClN_4$<br>Molecular Weight: 272.73 |
| 7-4 | Chemical Formula: $C_{18}H_{23}N_5O$<br>Molecular Weight: 325.41 |
| 7-5 | Chemical Formula: $C_{12}H_7ClN_4O_2$<br>Molecular Weight: 274.66 |
| 7-6 | Chemical Formula: $C_{12}H_7ClFN_3$<br>Molecular Weight: 247.66 |

TABLE VII-continued

Illustrative Imidazo[1,2-b]Pyridazine Pim-1 Kinase Inhibitors

| Compound | Structure |
|---|---|
| 7-7 | Chemical Formula: $C_{18}H_{11}F_2N_3$<br>Molecular Weight: 307.30 |
| 7-8 | Chemical Formula: $C_{12}H_7ClFN_3$<br>Molecular Weight: 247.66 |
| 7-9 | Chemical Formula: $C_{18}H_{11}F_2N_3$<br>Molecular Weight: 307.30 |
| 7-10 | Chemical Formula: $C_{16}H_{17}FN_4O$<br>Molecular Weight: 300.33 |
| 7-11 | Chemical Formula: $C_{16}H_{17}FN_4O$<br>Molecular Weight: 300.33 |

TABLE VII-continued

Illustrative Imidazo[1,2-b]Pyridazine Pim-1 Kinase Inhibitors

| Compound | Structure |
|---|---|
| 7-12 | 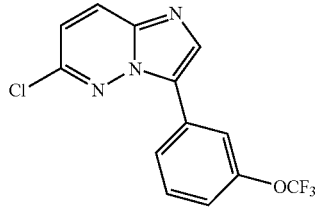<br>Chemical Formula: $C_{13}H_7ClF_3N_3O$<br>Molecular Weight: 313.66 |
| 7-13 | 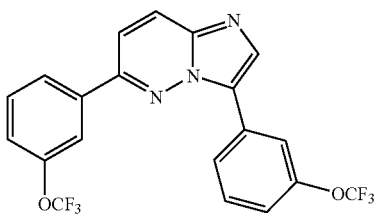<br>Chemical Formula: $C_{20}H_{11}F_6N_3O_2$<br>Molecular Weight: 439.31 |
| 7-14 | 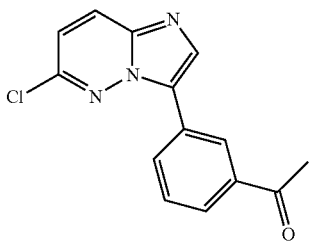<br>Chemical Formula: $C_{14}H_{10}ClN_3O$<br>Molecular Weight: 271.70 |
| 7-15 | 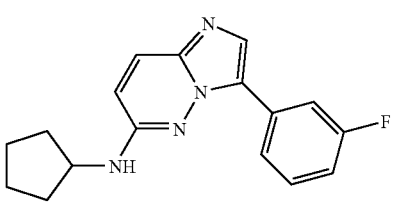<br>Chemical Formula: $C_{17}H_{17}FN_4$<br>Molecular Weight: 296.34 |
| 7-16 | 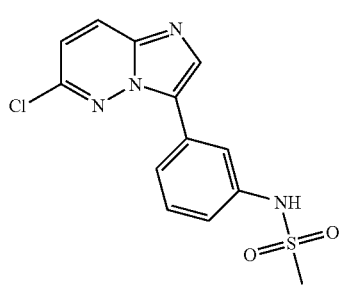<br>Chemical Formula: $C_{13}H_{11}ClN_4O_2S$<br>Molecular Weight: 322.77 |

TABLE VII-continued
Illustrative Imidazo[1,2-b]Pyridazine Pim-1 Kinase Inhibitors
| Compound | Structure |
|---|---|
| 7-17 | 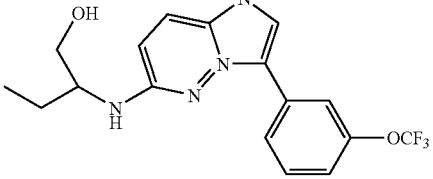<br>Chemical Formula: $C_{17}H_{17}F_3N_4O_2$<br>Molecular Weight: 366.34 |
| 7-18 | 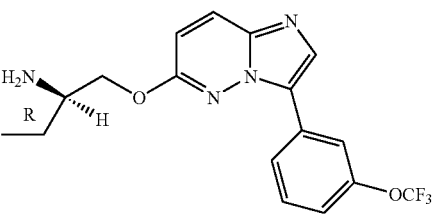 |
| 7-19 | 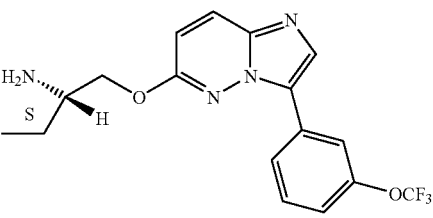 |
| 7-20 | 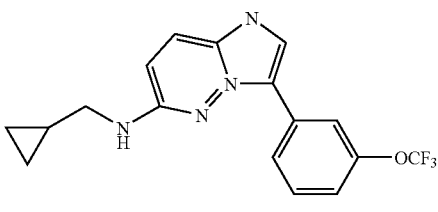<br>Chemical Formula: $C_{17}H_{15}F_3N_4O$<br>Molecular Weight: 348.32 |
| 7-21 | 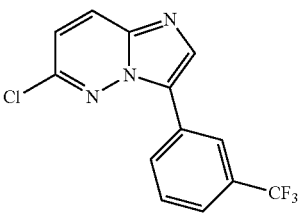<br>Chemical Formula: $C_{13}H_7ClF_3N_3$<br>Molecular Weight: 297.66 |
| 7-22 | 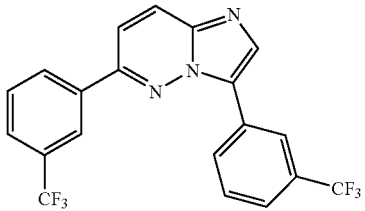<br>Chemical Formula: $C_{20}H_{11}F_6N_3$<br>Molecular Weight: 407.31 |

TABLE VII-continued

Illustrative Imidazo[1,2-b]Pyridazine Pim-1 Kinase Inhibitors

| Compound | Structure |
|---|---|
| 7-23 | Chemical Formula: $C_{17}H_{21}N_5O_3S$<br>Molecular Weight: 375.45 |
| 7-24 | Chemical Formula: $C_{17}H_{17}F_3N_4O$<br>Molecular Weight: 350.34 |
| 7-25 | Chemical Formula: $C_{17}H_{15}F_3N_4$<br>Molecular Weight: 332.32 |
| 7-26 | Chemical Formula: $C_{17}H_{19}N_5O_2S$<br>Molecular Weight: 357.43 |
| 7-27 | Chemical Formula: $C_{24}H_{28}F_3N_5O_3$<br>Molecular Weight: 491.51 |

TABLE VII-continued

Illustrative Imidazo[1,2-b]Pyridazine Pim-1 Kinase Inhibitors

| Compound | Structure |
|---|---|
| 7-28 | Chemical Formula: $C_{19}H_{20}F_3N_5O$<br>Molecular Weight: 391.39 |
| 7-29 | Chemical Formula: $C_{20}H_{22}F_3N_5O$<br>Molecular Weight: 405.42 |
| 7-30 | Chemical Formula: $C_{19}H_{20}F_3N_5O$<br>Molecular Weight: 391.39 |
| 7-31 | Chemical Formula: $C_{22}H_{27}F_3N_6O$<br>Molecular Weight: 448.48 |
| 7-32 | Chemical Formula: $C_{17}H_{17}F_3N_4O_2$<br>Molecular Weight: 366.34 |

TABLE VII-continued

Illustrative Imidazo[1,2-b]Pyridazine Pim-1 Kinase Inhibitors

| Compound | Structure |
|---|---|
| 7-33 | Chemical Formula: $C_{20}H_{21}F_3N_4O_2$<br>Molecular Weight: 406.4 |
| 7-34 | Chemical Formula: $C_{21}H_{23}F_3N_4O_2$<br>Molecular Weight: 420.43 |
| 7-35 | Chemical Formula: $C_{22}H_{26}F_3N_5O$<br>Molecular Weight: 433.47 |
| 7-36 | Chemical Formula: $C_{23}H_{24}F_3N_5O_2$<br>Molecular Weight: 459.46 |
| 7-37 | Chemical Formula: $C_{21}H_{24}F_3N_5O$<br>Molecular Weight: 419.44 |

TABLE VII-continued

Illustrative Imidazo[1,2-b]Pyridazine Pim-1 Kinase Inhibitors

| Compound | Structure |
|---|---|
| 7-38 | Chemical Formula: $C_{22}H_{26}F_3N_5O$<br>Molecular Weight: 433.47 |
| 7-39 | Chemical Formula: $C_{21}H_{24}F_3N_5O$<br>Molecular Weight: 419.44 |
| 7-40 | Chemical Formula: $C_{25}H_{25}F_3N_6O$<br>Molecular Weight: 482.5 |
| 7-41 | Chemical Formula: $C_{24}H_{23}F_3N_6O$<br>Molecular Weight: 468.47 |
| 7-42 | Chemical Formula: $C_{21}H_{24}F_3N_5O_2$<br>Molecular Weight: 435.44 |

TABLE VII-continued

Illustrative Imidazo[1,2-b]Pyridazine Pim-1 Kinase Inhibitors

| Compound | Structure |
| --- | --- |
| 7-43 | Chemical Formula: $C_{20}H_{22}F_3N_5O_2$<br>Molecular Weight: 421.42 |
| 7-44 | Chemical Formula: $C_{22}H_{26}F_3N_5O_2$<br>Molecular Weight: 449.47 |
| 7-45 | Chemical Formula: $C_{21}H_{24}F_3N_5O_2$<br>Molecular Weight: 435.44 |
| 7-46 | Chemical Formula: $C_{22}H_{26}F_3N_5O_2$<br>Molecular Weight: 449.47 |

TABLE VII-continued

Illustrative Imidazo[1,2-b]Pyridazine Pim-1 Kinase Inhibitors

| Compound | Structure |
| --- | --- |
| 7-47 | Chemical Formula: $C_{21}H_{24}F_3N_5O_2$<br>Molecular Weight: 435.44 |
| 7-48 | Chemical Formula: $C_{23}H_{28}F_3N_5O_2$<br>Molecular Weight: 463.5 |
| 7-49 | Chemical Formula: $C_{22}H_{26}F_3N_5O_2$<br>Molecular Weight: 449.47 |
| 7-50 | Chemical Formula: $C_{23}H_{28}F_3N_5O_2$<br>Molecular Weight: 463.5 |

TABLE VII-continued

Illustrative Imidazo[1,2-b]Pyridazine Pim-1 Kinase Inhibitors

| Compound | Structure |
|---|---|
| 7-51 | Chemical Formula: $C_{22}H_{26}F_3N_5O$ <br> Molecular Weight: 433.47 |

Example 7

Pim-1 Kinase Activity Assays $IC_{50}$ values were determined for illustrative compounds (e.g., from Table VII) using the Promega Kinase-Glo assay, the results for which are summarized in Table VIII below. In addition, illustrative compounds were evaluated for cell-based activity in cells expressing Pim-1. $IC_{50}$ values, representing the concentrations required to inhibit cell growth to 50% of untreated, are provide in μM in Table IX below. Thus, by multiple assays, these illustrative compounds represent active inhibitors of Pim-1 kinase and are capable of inhibiting tumor cell growth.

TABLE VIII

Kinase Inhibitory Activity of Representative Compounds

| Compound | IC50 (Kinase) |
|---|---|
| 7-1 | 3.99 uM |
| 7-4 | 1.81 uM |
| 7-7 | 9.76 uM |
| 7-9 | 86.60 uM |
| 7-10 | 3.96 uM |
| 7-11 | 3.05 uM |
| 7-15 | 5.35 uM |
| 7-17 | 418 nM |
| 7-18 | 481 nM |
| 7-19 | 293 nM |
| 7-20 | 2.68 uM |
| 7-23 | 8.23 uM |
| 7-24 | 519 nM |
| 7-25 | 798 nM |
| 7-27 | 7.49 uM |
| 7-28 | 127 nM |
| 7-29 | 7.4 nM/138.6 nM |
| 7-30 | 761 nM |
| 7-31 | 267 nM |
| 7-32 | 1.55 uM/95 nM |
| 7-33 | 405 nM/282 nM |
| 7-34 | 272 nM |
| 7-35 | 79 nM |
| 7-36 | 73 nM |
| 7-37 | 13 nM |
| 7-39 | 111 nM/18 nM |
| 7-43 | 1.10 uM |
| 7-47 | 310 nM |
| 7-49 | 310 nM |

TABLE IX

Cell-Based Activity of Representative Compounds.

| Compound Name | IC50 (K562) | IC50 (PC-3) |
|---|---|---|
| 7-1 | 67.1 uM | 29.22 uM |
| 7-4 | 13.55 uM | 54.59 uM |
| 7-7 | 270.84 uM | 87.25 uM |
| 7-9 | 6.76 uM | 21.18 uM |
| 7-10 | 37.48 uM/25.76 uM | 69.56 uM |
| 7-11 | 7.31 uM/8.05 uM | 18.41 uM |
| 7-13 | 19.07 uM | 63.25 uM |
| 7-15 | 20.83 uM | 70.20 uM |
| 7-17 | 5.38 uM | 9.37 uM |
| 7-18 | 5.82 uM | — |
| 7-19 | 5.84 uM | — |
| 7-20 | 7.79 uM | 20.75 uM |
| 7-23 | 23.19 uM | 24.55 uM |
| 7-24 | 4.26 uM | 7.27 uM |
| 7-25 | 4.64 uM | 8.15 uM |
| 7-26 | NS | NS |
| 7-27 | 10.30 uM | — |
| 7-28 | 1.95 uM | — |
| 7-29 | 2.29 uM | 4.83 uM |
| 7-30 | 9.14 uM | 9.26 uM |
| 7-32 | 25.32/19.99 uM | 29.0 uM |
| 7-33 | 5.99 uM | 14.37 uM |
| 7-34 | 1.73 uM | 7.21 uM |
| 7-35 | 2.92 uM | 12.77 uM |
| 7-36 | 6.91 uM | 33.32 uM |
| 7-37 | 3.89 uM | 8.95 uM |
| 7-38 | 1.41 uM | 5.68 uM |
| 7-39 | 1.66 uM | 5.82 uM |
| 7-42 | 9.6 uM | 8.96 uM |
| 7-43 | 4.9 uM | N/A |
| 7-44 | 5.7 uM | 17.7 uM |
| 7-45 | 14.9 uM | 52.0 uM |
| 7-46 | 5.3 uM | 10.6 uM |
| 7-47 | 11.3 uM | 57.4 uM |
| 7-48 | 5.7 uM | 17.7 uM |

Example 8

Selectivity of Compound 7-29 for Particular Protein Kinases

Compound 7-29 (Table VII) was evaluated for selectivity against a panel of Ser/Thr and Tyrosine kinases in the radiometric assay at 1 mM. The results are summarized in FIG. 2. Against the Ser/Thr kinases tested, compound 7-29 exhibited Pim1 kinase selectivity >100-fold over other kinases tested. Compound 7-29, however, was also exhibited selectivity against Flt3, Mek1 and TrkA. This compound showed no significant activity against a panel of other Ser/Thr kinase including Aurora-A, CDK1, CDK2, Plk3 and Nek2 and Tyrosine kinase including Able, c-Kit, EGFR and Jak2.

Example 9

This example demonstrates Pim-1 kinase inhibitory activity for the HCl salts of illustrative Compounds 7-19, 7-29 and 7-31.

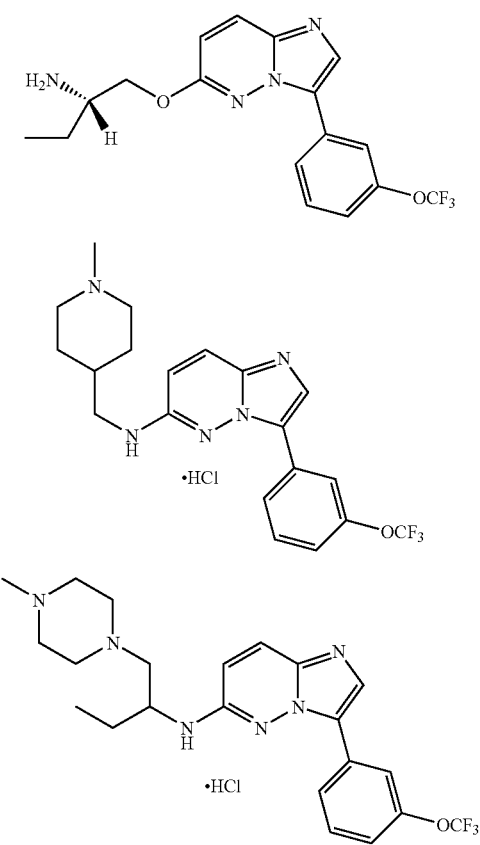

One illustrative manner to determine the effect of Pim-1 inhibitors on the activity of the Pim-1 kinase is to measure the phosphorylation levels of the protein Bad at serine residue 112 (S112) (phospho-Bad or pBad). Pim-1 is known to cause the phosphorylation of Bad at S112 in order to inactivate the protein and inhibit its association with anti-apoptotic Bcl-2 family members, thereby allowing these Bcl-2 family members to further inhibit apoptotic signals.

Briefly, MV-4-11 (biphenotypic B myelomonocytic leukemia) cells were plated into T25 flasks in serum free media (SFM) at $1.5 \times 10^5$ cells/ml and allowed to grow for 24 hrs. After 24 hrs Pim-1 inhibitors at 10, 5, 1, 0.5, 0.1, or 0.01 μM concentrations were added to individual flasks. Treatment with the Pim-1 inhibitors continued for a duration of 1 hr. Cells were harvested after the 1 hr treatment and cell lysates were made from each sample. Equal amounts of total protein from the lysates were loaded onto a 10% Tris-glycine gel (Invitrogen) for SDS-PAGE analysis. After the proteins had been separated by SDS-PAGE they were transferred to nitrocellulose membranes (Invitrogen) for Western blotting. The primary antibody for phospho-Bad (S112) (Cell Signaling Technologies) was used to probe for the levels of phospho-Bad (S112). In order to calculate the $EC_{50}$ of inhibitors on phosphorylation of Bad (S112), the levels of total Bad protein were determined. To accomplish this, the original Western blot was stripped of antibodies and re-probed using antibodies that recognize the Bad protein (Cell Signaling Technologies), indiscriminate of the phosphorylation state of the protein. Densitometry was used to quantitate the levels of each band on the Western blots and used to determine the $EC_{50}$ of the Pim-1 inhibitors to alter the phospho-Bad protein levels.

FIGS. 3-5 show the results for the phospho-Bad staining on MV-4-11 cells treated with Compounds 7-19, 7-29, and 7-31, respectively. After the 1 hr treatment with the Pim-1 inhibitors, the levels of pBad decreased in a dose-dependent manner, showing a near complete absence of pBad at the highest levels. Levels of total Bad were similar across the treatment groups. The $EC_{50}$ values for Compounds 7-19, 7-29 and 7-31 were determined to be 635 nM, 7.9 nM, and 57.4 nM, respectively.

We claim:
1. A compound having a structure according to structure (I) below:

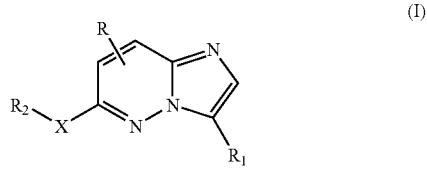

or a stereoisomer, prodrug or pharmaceutically acceptable salt thereof,
wherein:
X is NH;
R is H, —OH, halo, alkyl, haloalkyl, alkoxy or haloalkoxy;
$R_1$ is phenyl or substituted phenyl; and
$R_2$ is —$(CH_2)_{1,2}$-piperid-4-yl, substituted —$(CH_2)_{1,2}$-piperid-4-yl, —$(CH_2)_{1,2}$-piperazin-1-yl, or substituted —$(CH_2)_{1,2}$-piperazin-1-yl.

2. The compound of claim 1 wherein R is hydrogen.
3. The compound of claim 1 wherein R is methyl.
4. The compound of claim 1 wherein $R_1$ is substituted phenyl having at least one p, o or m substituent selected from —$OCF_3$, —$OCHF_2$, —$CF_3$, —$OCH_3$, and —OH.
5. The compound of claim 1 wherein $R_1$ is selected from:

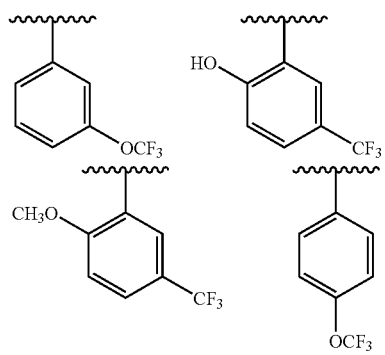

-continued

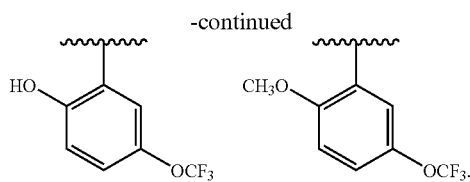

6. The compound of claim 1 wherein R₂ is substituted —(CH₂)₁,₂-piperid-4-yl or substituted —(CH₂)₁,₂-piperazin-1-yl having one or two substituents selected from alkyl.

7. The compound of claim 6 wherein R₂ is selected from:

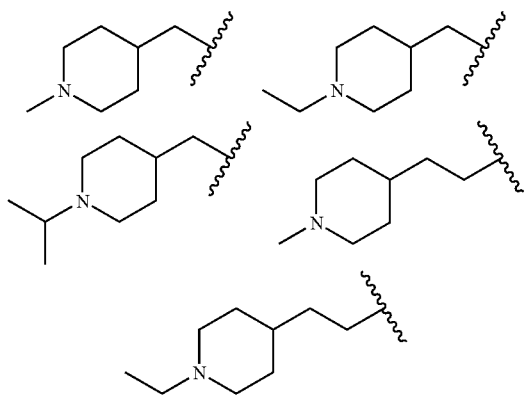

-continued

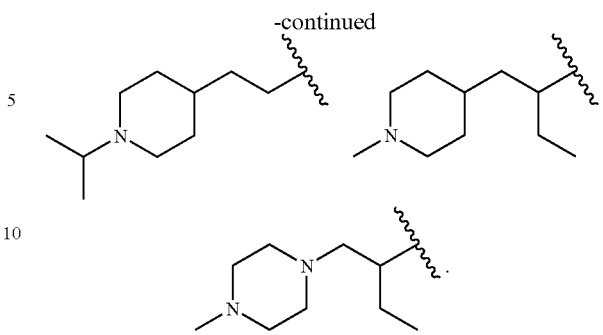

8. The compound of claim 1, wherein the compound is:
N-((1-methylpiperidin-4-yl)methyl)-3-(3-(trifluoromethoxy)-phenyl)imidazo[1,2-b]pyridazin-6-amine (Compound 7-29);
N-(2-(4-methylpiperazin-1-yl)butyl)-3-(3-(trifluoromethoxy)-phenyl)imidazo[1,2-b]pyridazin-6-amine (Compound 7-31);
7-methyl-N-((1-methylpiperidin-4-yl)methyl)-3-(3-trifluoromethoxy)-phenyl)imidazo[1,2-b]pyridazin-6-amine (Compound 7-37); or
N-((1-ethylpiperidin-4-yl)methyl)-3-(3-(trifluoromethoxy)-phenyl)imidazo[1,2-b]pyridazin-6-amine (Compound 7-39).

9. A composition comprising a compound of claim 1 in combination with a pharmaceutically acceptable excipient.

* * * * *